(12) United States Patent
Trovitch et al.

(10) Patent No.: US 9,708,355 B2
(45) Date of Patent: Jul. 18, 2017

(54) FIRST-ROW TRANSITION METAL HYDROGENATION AND HYDROSILYLATION CATALYSTS

(71) Applicant: ARIZONA BOARD OF REGENTS ON BEHALF OF ARIZONA STATE UNIVERSITY, Scottsdale, AZ (US)

(72) Inventors: Ryan J. Trovitch, Phoenix, AZ (US); Tufan K. Mukhopadhyay, Tempe, AZ (US); Raja Pal, Tempe, AZ (US); Hagit Ben-Daat Levin, Scottsdale, AZ (US); Tyler M. Porter, Cave Creek, AZ (US); Chandrani Ghosh, Wolkata (IN)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/896,813

(22) PCT Filed: Jun. 11, 2014

(86) PCT No.: PCT/US2014/041845
§ 371 (c)(1),
(2) Date: Dec. 8, 2015

(87) PCT Pub. No.: WO2014/201082
PCT Pub. Date: Dec. 18, 2014

(65) Prior Publication Data
US 2016/0176908 A1 Jun. 23, 2016

Related U.S. Application Data

(60) Provisional application No. 61/834,220, filed on Jun. 11, 2013, provisional application No. 61/916,448, filed on Dec. 16, 2013.

(51) Int. Cl.
| | | |
|---|---|---|
| *C07F 13/00* | (2006.01) | |
| *B01J 31/12* | (2006.01) | |
| *C07F 15/06* | (2006.01) | |
| *C07F 9/50* | (2006.01) | |
| *C07F 15/02* | (2006.01) | |
| *C07F 15/04* | (2006.01) | |
| *C07F 7/08* | (2006.01) | |
| *C07F 7/18* | (2006.01) | |
| *B01J 31/00* | (2006.01) | |
| *B01J 31/18* | (2006.01) | |
| *B01J 31/24* | (2006.01) | |

(52) U.S. Cl.
CPC .......... *C07F 15/065* (2013.01); *B01J 31/00* (2013.01); *B01J 31/1815* (2013.01); *B01J 31/24* (2013.01); *C07F 7/0809* (2013.01); *C07F 7/0896* (2013.01); *C07F 7/1836* (2013.01); *C07F 7/1868* (2013.01); *C07F 9/5045* (2013.01); *C07F 13/005* (2013.01); *C07F 15/025* (2013.01); *C07F 15/045* (2013.01); *B01J 2231/323* (2013.01); *B01J 2531/72* (2013.01); *B01J 2531/842* (2013.01); *B01J 2531/845* (2013.01); *B01J 2531/847* (2013.01)

(58) Field of Classification Search
CPC ............ C07F 13/00; C07F 15/00; B01J 31/12
USPC ............................................. 546/10; 502/167
See application file for complete search history.

(56) References Cited

U.S. PATENT DOCUMENTS

| | | | |
|---|---|---|---|
| 3,159,601 A | 12/1964 | Ashby | |
| 3,220,972 A | 11/1965 | Lamoreaux | |
| 3,592,870 A * | 7/1971 | Dunn | B01J 31/1805 502/117 |
| 3,775,432 A | 11/1973 | Siddall et al. | |
| 4,005,127 A | 1/1977 | Knowles et al. | |
| 5,272,056 A * | 12/1993 | Burrows | C12Q 1/68 435/6.16 |
| 8,236,915 B2 | 8/2012 | Delis et al. | |
| 8,415,443 B2 | 4/2013 | Delis et al. | |
| 2011/0009565 A1 | 1/2011 | Delis et al. | |
| 2011/0009573 A1 | 1/2011 | Delis et al. | |
| 2012/0130021 A1 | 5/2012 | Tondreau et al. | |
| 2012/0130106 A1 | 5/2012 | Chirik et al. | |
| 2013/0079567 A1 | 3/2013 | Chirik et al. | |

FOREIGN PATENT DOCUMENTS

| | | |
|---|---|---|
| WO | 03/042131 A1 | 5/2003 |
| WO | 2013/043783 A2 | 3/2013 |
| WO | 2013/043785 A2 | 3/2013 |
| WO | 2013/043846 A1 | 3/2013 |
| WO | 2013/043874 A2 | 3/2013 |
| WO | 2013/043912 A2 | 3/2013 |

OTHER PUBLICATIONS

Mukhopadhyay, T.K. et al.: A highly active manganese precatalyst for the hydrosilation of ketones and esters. J. Am. Chem. Soc., vol. 136, pp. 882-885, 2014.*

Inagaki, T. et al., "Iron- and Cobalt-Catalyzed Asymmetric Hydrosilylation of Ketones and Enones with Bis(oxazolinylphenyl)amine Ligands", Chem. Eur. J., 16, pp. 3090-3096 (2010).

Yu, F. et al., "Cobalt(II)-catalyzed asymmetric hydrosilylation of simple ketones using dipyridylphosphine ligands in air", Org. Biomol. Chem., 9, pp. 5652-5654 (2011).

(Continued)

*Primary Examiner* — Charanjit Aulakh
(74) *Attorney, Agent, or Firm* — Quarles & Brady LLP

(57) ABSTRACT

Transition metal compounds, and specifically transition metal compounds having a tetradentate and/or pentadentate supporting ligand are described, together with methods for the preparation thereof and the use of such compounds as hydrogenation and/or hydrosilylation catalysts.

12 Claims, 21 Drawing Sheets

(56) References Cited

OTHER PUBLICATIONS

Mao, Z. et al., "Catalytic Hydrosilation of Organic Esters Using manganse Carbonyl Acetyl Complexes, (L)(CO)4MnC(O)CH3 (L=CO, PPh3)", J. Am. Chem. Soc., 117, pp. 10139-10140 (1995).
International Search Report and Written Opinion under date of mailing of Sep. 30, 2014 in connection with PCT/US2014/041845.
Du Bois, Four- and Five-Coordinate Nickel(II) Complexes of 2,3-Butanedionebis(2-diphenyl phosphinoethylimine), Inorganic Chemistry, vol. 11, No. 4, 1972, pp. 718-722.

* cited by examiner

FIRST-ROW TRANSITION METAL HYDROGENATION AND HYDROSILYLATION CATALYSTS

CROSS-REFERENCE TO RELATED APPLICATIONS

This application claims the benefit of U.S. Provisional Application No. 61/834,220 filed on Jun. 12, 2013 and U.S. Provisional Application No. 61/916,448 filed on Dec. 16, 2013. Each of these applications is incorporated by reference herein in its entirety.

STATEMENT REGARDING FEDERALLY SPONSORED RESEARCH OR DEVELOPMENT

This invention was made with government support under DE-SC0001016 awarded by the Department of Energy. The government has certain rights in the invention.

BACKGROUND

Technical Field

The present disclosure relates to transition metal compounds and the preparation thereof, and more specifically to first-row transition metal complexes having a tetradentate and/or pentadentate supporting ligand and the use of such complexes as hydrogenation and/or hydrosilylation catalysts.

Technical Background

In recent years, 2,6-bis(imino)pyridine (or pyridine diimine, PDI) ligands have become an increasingly utilized ligand class due to their ease of synthesis, steric and electronic modularity, and ability to coordinate to a wide range of transition and alkali metal ions. Furthermore, the capacity of these chelates to accept one or more electrons from a metal center has been well documented and metrics to differentiate varying degrees of PDI reduction have been established. This redox non-innocence has proven invaluable for the advancement of base-metal hydrogenation, hydrosilylation, and cyclization catalysts whose activity rival traditionally employed precious metal complexes.

While impressive, these achievements have overwhelmingly depended on the use of sterically demanding aryl imine substituents ($^{Ar}$PDI). For example, the initial preparation of an ($^{Ar}$PDI)Fe hydrogenation catalyst depended on the incorporation of two 2,6-diisopropylphenyl imine substituents while preliminary efforts to prepare analogues with less bulky imine substituents resulted in the formation of bis(ligand) complexes rather than catalytically relevant dinitrogen complexes.

Although reduction of the respective ($^{Ar}$PDI)FeBr$_2$ starting complexes using sodium naphthalenide rather than sodium amalgam has since afforded highly active hydrogenation catalysts with smaller aryl groups, the success of this approach has remained limited to 2,6-diethylphenyl or 2,6-dimethylphenyl imine substituents.

While alkyl imine PDI substituents have allowed the preparation of asymmetric Co(I) hydrogenation catalysts, their use has not yet enabled the isolation of an ($^R$PDI)Fe (R=alkyl) hydrogenation catalyst. Similar observations have been made for related α-diimine (DI) supported first row metal catalysts.

Two of the most popular and well-studied catalytic transformations that homogeneous transition metal complexes are known to mediate are the hydrogenation and hydrosilylation of unsaturated compounds. Hydrogenation catalysts have been heavily utilized by the chemical industry and have played a large role in the synthesis of pharmaceutical precursors and products. On the other hand, homogeneous hydrosilylation catalysts are often employed to prepare silicone-based fluids, surfactants, adhesives, sealants, and coatings.

Hydrogenation, which relies upon the transfer of two hydrogen atoms from a sacrificial substrate to, or the direct addition of dihydrogen across, a C=C, C=O, or C=N bond, has traditionally been conducted in the presence of a homogenous or heterogeneous precious metal catalyst (mainly Ru, Rh, or Pt). One well-known example of this application remains the preparation of L-DOPA following the asymmetric hydrogenation of a substituted, prochiral acetamidocinnamic acid with [Rh(COD)$_2$]$^+$ in the presence of a chiral phosphine, as disclosed in U.S. Pat. No. 4,005,127. Asymmetric hydrogenation has also been utilized in the preparation of other chemicals, including aspartame, N-acetylcysteine, and flamprop-isopropyl.

Hydrosilylation, which typically involves the addition of a silyl hydride across a C=C, C=O, C—O, or C=N bond, has also traditionally been conducted in the presence of a homogenous or heterogeneous precious metal catalyst (mainly Rh or Pt). For example, a variety of silicone polymers have been prepared using platinum-based complexes, such as Karstedt's catalyst (U.S. Pat. No. 3,775,452), Ashby's catalyst (U.S. Pat. No. 3,159,601), Lamoreaux's catalyst (U.S. Pat. No. 3,220,972), and Speier's catalyst (J. Am. Chem. Soc. 1957, 79, 974.).

Although widely accepted precious metal complexes are efficient at catalyzing hydrogenation and hydrosilylation reactions, several drawbacks tied to their use remain. The precious metals themselves (Ru, Os, Rh, Ir, Pd, and Pt) are orders of magnitude more expensive than their first row transition metal congeners (Fe, Co, and Ni), which are found in abundance within the Earth's crust. Likewise, manganese is a low-cost and widely available first-row transition metal.

In addition to the cost advantage associated with developing efficient first-row metal catalysts, precious metals are highly toxic and must often be scrupulously removed from the hydrogenated or hydrosilylated product before it can be released to the public, a complication that also increases the overall cost basis of the transformation. Additionally, precious metal hydrosilylation catalysts are known to catalyze the formation of undesired by-products when reacted with substrates such as allyl ethers and are often susceptible to poisoning upon reaction with trace amine or phosphine impurities.

Although well-defined Mn complexes are not widely known for their ability to hydrogenate unsaturated substrates, there has been recent interest in developing Mn hydrosilylation catalysts. Several recent disclosures describe Mn hydrosilylation catalysts that are supported by kappa3-terpyridine (U.S. Pat. Pub. No. 2011/0009565), kappa3-pyridine diimine (U.S. Pat. Pub. No. 2011/0009573), and kappa3-bis(imino)quinolone ligands (U.S. Pat. Pub. No. 2012/0130021). Related disclosures describing the in situ activation of Mn complexes bearing these ligands (U.S. Pat. Pub. No. 2012/0130106), as well as a variety of other common supporting scaffolds (Int. Pat. Pub. No. WO2013/043874), have also been filed.

U.S. Patent Pub. Nos. 2011/0009565, 2011/0009573, and 2012/0130021 also cover the Fe, Co, and Ni mediated hydrosilylation of unsaturated substrates supported by kappa3-terpyridine, kappa3-pyridine diimine, and kappa3-bis(imino)quinolone ligands, respectively while U.S. Pat.

Pub. No. 2012/0130106 describes the in situ activation of Fe, Co, and Ni precatalysts in the presence of the same ligand frameworks.

In a similar disclosure, the in situ activation of Fe, Co, and Ni precursors in the presence of a range of ligands has recently been filed as Int. Pat. Pub. No. WO2013/043912 and individually for Fe (Int. Pat. Pub. No. WO2013/043912), Co (Int. Pat. No. WO2013/043783), and Ni (Int. Pat. Pub. No. WO2013/043875) precursors.

There has also been recent interest in the development of well-defined Fe, Co, and Ni catalysts for the hydrogenation of olefins and alkynes. In U.S. Pat. Pub. No. 2013/0079567, tridentate ligands with chiral carbon-containing imine substituents (that may or may not be cyclometallated) have been reported to mediate the asymmetric hydrogenation of prochiral olefins. U.S. Pat. Pub. No. 2013/0079567 also covers non-asymmetric Fe, Co, and Ni hydrogenation catalysts bearing a kappa3-bis(imino)pyridine (or related) ligand.

There is a continuing need in the art for improved first-row transition metal complex catalysts that can mediate the hydrogenation or hydrosilylation of unsaturated substrates with high efficiency under mild conditions.

BRIEF SUMMARY

The present disclosure relates to transition metal compounds and the preparation thereof, and more specifically to transition metal compounds having a tetradentate and/or pentadentate supporting ligand and the use of such compounds as hydrogenation and/or hydrosilylation catalysts.

Specifically, the disclosure relies upon the use of kappa4- and kappa5-chelating ligands that are conceptually different than those discussed in the aforementioned disclosures to prepare well-defined hydrosilylation and hydrogenation catalysts that are ready for direct application, obviating the requirement for in situ activation. Importantly, the capacity of the supporting ligand to engage in kappa4- or kappa5-binding throughout the course of the transformation may provide extra stability to the transition metal when high-energy, low-electron count transition states or intermediates are encountered and help to prevent catalyst poisoning.

In some embodiments, the complexes optionally contain a hydride ligand or have been prepared following hydride transfer to the chelate imine carbon atom. The added hydride moiety can result in increased catalytic activity for mediating hydrosilylation and hydrogenation reactions.

Accordingly, in a first aspect, the disclosure encompasses a metal complex including a first-row transition metal and a kappa4- or kappa5-chelating ligand. The metal complex has one of the following chemical structures, or is a salt thereof:

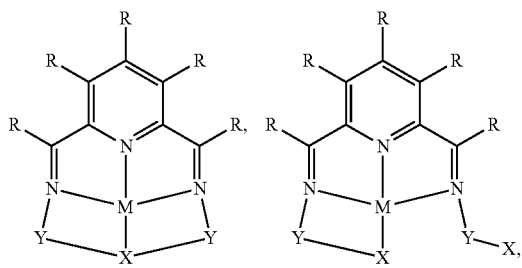

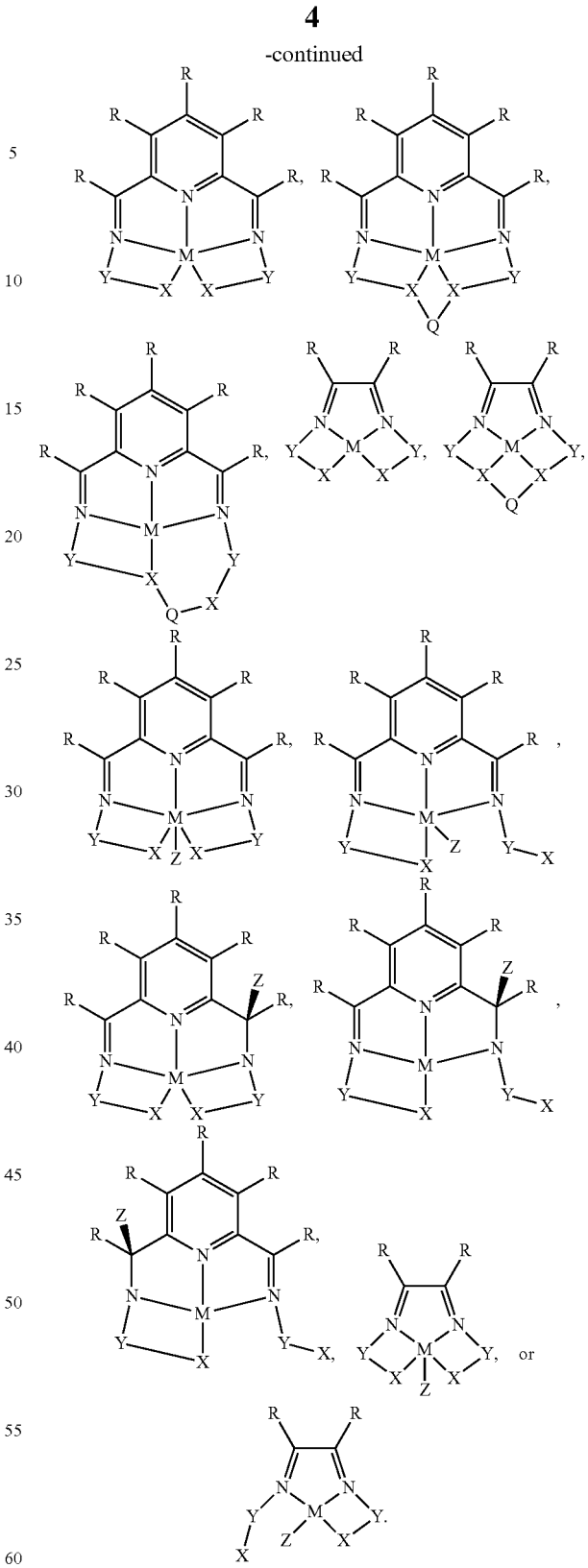

Each X is independently selected from $PR_n$, $NR_n$, $AsR_n$, $SbR_n$, $BiR_n$, $OR_n$, $SR_n$, $SeR_n$, $TeR_n$, and any other donor group, where n=2, 1, or 0, a heterocycle containing one of these donor atoms, and any combination thereof.

Each R is independently selected from hydrogen, an inert functional group, a substituted, unsubstituted, or cyclic $C_{1-24}$ alkyl group optionally having one or more heteroatoms, an aryl or substituted aryl group that optionally contains one or more heteroatoms, a moiety where two R groups taken together form a ring that is a substituted or unsubstituted, saturated or unsaturated cylic structure that optionally contains one or more heteroatoms, a halogen, an alkoxide, an amide, a silyl, a boryl, and combinations thereof.

Each Y is independently selected from a substituted or unsubstituted $C_{1-24}$ alkylene linking group optionally having one or more heteroatoms but not an aryl functionality directly attached to N.

Q is a substituted, unsubstituted, or cyclic $C_{1-24}$ alkylene linking group optionally having one or more heteroatoms, or an aryl or substituted aryl linking group that optionally contains one or more heteroatoms.

Z is a hydride, an alkyl, an aryl, an alkoxide, an amide, a silyl, or a boryl.

In certain embodiments, M is Mn, Fe, Co, or Ni.

In certain embodiments, each X is independently selected from $PR_2$, $NR_2$, and any other donor group.

In certain embodiments, Z is hydride.

In a second aspect, the disclosure encompasses a catalytic composition comprising any of the metal complexes described above.

In a third aspect, the disclosure encompasses a method for reducing one or more organic substrates. The methods include the step of contacting a composition comprising one or more organic substrates with a catalytic composition comprising a metal complex as described above in the presence of a reductant, whereby the one or more organic substrates are reduced.

In some embodiments, the reductant is a silane, a substituted silane, an alkoxysilane, hydrogen, a substituted borane, a substituted alane, or a mixture thereof.

In some embodiments, the one or more organic substrates contain a ketone, an ester, or mixtures thereof.

In some embodiments, the one or more organic substrates include an unsaturated organic compound. In some such embodiments, the unsaturated organic compound contains an olefin or an alkyne.

In a fourth aspect, the disclosure encompasses a method of facilitating a hydrosilylation reaction. The method includes the step of reacting a compound comprising a Si—H bond with an unsaturated organic compound in the presence of one or more of the metal complexes described above. In some such embodiments, the Si and H atoms in the Si—H bond are added across an unsaturated bond in the unsaturated organic compound to form an organosilicon compound.

In a fifth aspect, the disclosure encompasses a method of facilitating a hydrogenation reaction. The method includes the step of reacting $H_2$ with an unsaturated organic compound in the presence of one or more of the metal complexes as described above. In some such embodiments, the H atoms in the $H_2$ are added across an unsaturated bond in the unsaturated organic compound to reduce the unsaturated bond.

In a sixth aspect, the disclosure encompasses a method of preparing a catalytic composition as described herein.

BRIEF DESCRIPTION OF THE FIGURES

The accompanying figures, which are incorporated in and constitute a part of this specification, illustrate several aspects and together with the description serve to explain the principles of the invention.

Figure 1:
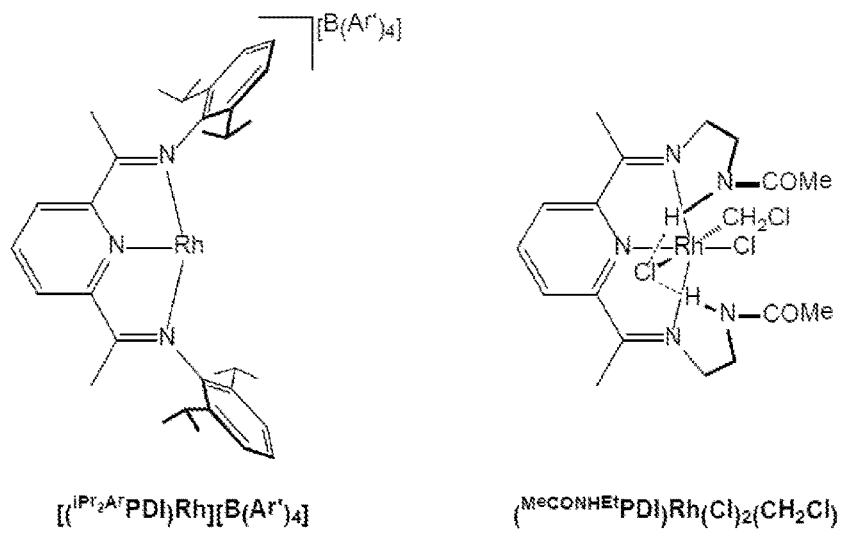
FIG. 1 illustrates a persistent, 3-coordinate cationic Rh complex supported by a sterically demanding PDI ligand (left), and an octahedral (PDI)Rh complex featuring hydrogen bonding interactions between an apical chloride ligand and two amide arms, in accordance with various aspects of the present disclosure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

The present invention can be understood more readily by reference to the following detailed description of the invention and the Examples included therein.

Before the present compounds, devices, and/or methods are disclosed and described, it is to be understood that they are not limited to specific synthetic methods or temperatures unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

The terms "amine" or "amino" as used herein are represented by the formula NA$^1$A$^2$A$^3$, where A$^1$, A$^2$, and A$^3$ can be, independently, hydrogen or optionally substituted alkyl, cycloalkyl, alkenyl, cycloalkenyl, alkynyl, cycloalkynyl, aryl, or heteroaryl group as described herein.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "nitrile" as used herein is represented by the formula —CN.

The term "thiol" as used herein is represented by the formula —SH.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein.

For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed.

This concept applies to all aspects of this application including, but not limited to, steps in methods of making and using the compositions of the invention. Thus, if there are a variety of additional steps that can be performed, it is understood that each of these additional steps can be performed with any specific embodiment or combination of embodiments of the methods of the invention.

As briefly described above, the present disclosure is directed to transition metal compounds and the preparation thereof, and more specifically to transition metal compounds having a tetradentate and/or pentadentate supporting ligand and the use of such compounds as hydrogenation and/or hydrosilylation catalysts. In one aspect, the transition metal compounds are complexes comprising manganese, iron, cobalt, nickel, or a combination thereof.

In various aspects, the catalyst materials of the present invention comprise one or more of the following structures:

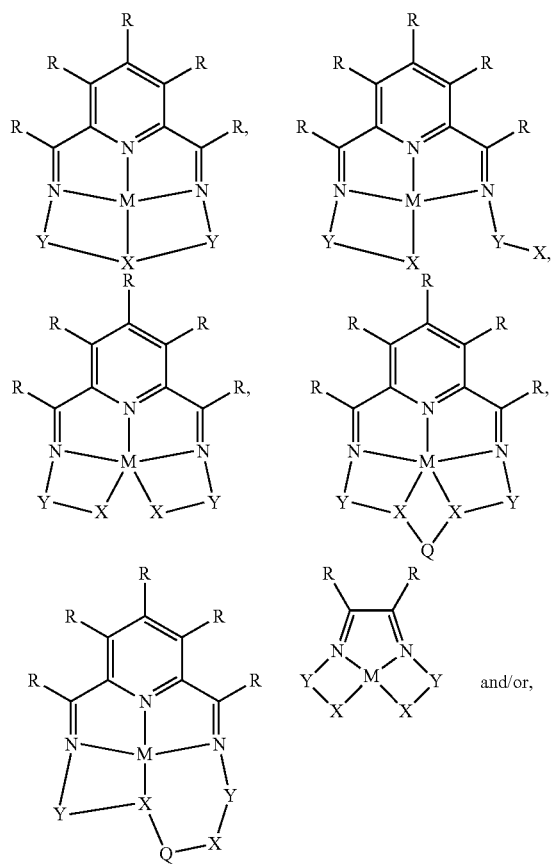

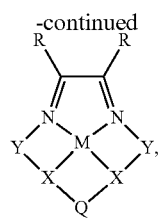

wherein M can comprise Mn, Fe, Co, Ni, or a combination thereof; wherein X can comprise $PR_n$, $NR_n$, and/or any donor group including $AsR_n$, $SbR_n$, $BiR_n$, $OR_n$, $SR_n$, $SeR_n$, $TeR_n$, where n=2, 1, or 0, or a heterocycle containing one of these donor atoms, or any combination thereof; wherein each R independently represents hydrogen, an inert functional group, a substituted, unsubstituted, or cyclic $C_{1-24}$ alkyl group optionally having one or more heteroatoms, an aryl or substituted aryl group that optionally contains one or more heteroatoms, or where two R groups taken together form a ring that is a substituted or unsubstituted, saturated or unsaturated cylic structure that optionally contains one or more heteroatoms, or a combination thereof; and wherein Y comprises a substituted or unsubstituted $C_{1-24}$ alkylene linking group optionally having one or more heteroatoms but not an aryl functionality directly attached to N, or any combination thereof; and wherein Q comprises a substituted, unsubstituted, or cyclic $C_{1-24}$ alkylene linking group optionally having one or more heteroatoms, or an aryl or substituted aryl linking group that optionally contains one or more heteroatoms. Complexes with this composition may be neutral or charged such that they form a salt with an outersphere counterion.

In one aspect, the transition metal compounds are complexes comprising manganese, iron, cobalt, nickel, or a combination thereof.

In one embodiment, the composition comprises

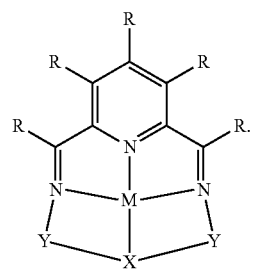

In another embodiment, the composition comprises

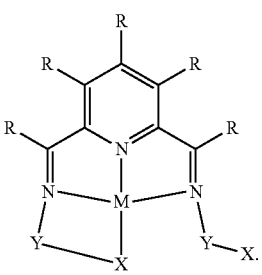

In yet another embodiment, the composition comprises

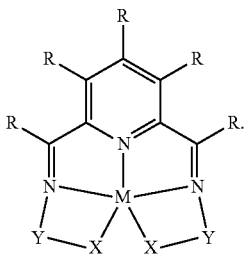

In yet another embodiment, the composition comprises

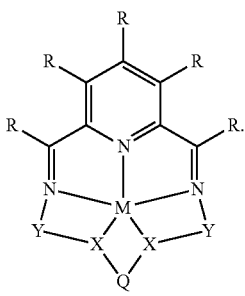

In yet another embodiment, the composition comprises

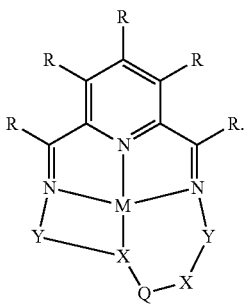

In yet another embodiment, the composition comprises

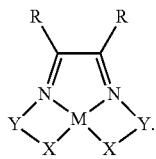

In still another embodiment, the composition comprises

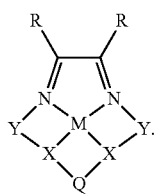

In some embodiments, the metal (M) of the inventive composition comprises manganese. In another aspect, the metal (M) of the inventive composition comprises iron. In yet another aspect, the metal (M) of the inventive composition comprises cobalt. In still another aspect, the metal (M) of the inventive composition comprises nickel.

In one aspect, the disclosure provides $\kappa^4$- and $\kappa^5$-chelating ligands that are conceptually different than those known and used in the art to prepare hydrogenation and hydrogenation catalysts. Importantly, the capacity of a supporting ligand to engage in $\kappa^4$- and $\kappa^5$-binding throughout the course of the transformation can provide extra stability to the transition metal when high energy transition states or intermediates are encountered and help to prevent catalyst poisoning. In one aspect, the compositions of the present invention can mediate the hydrogenation and/or hydrosilylation of, for example, unsaturated substrates with high efficiency under mild conditions.

In certain embodiments, the hydrosilylation of ketones can be catalyzed using ($\kappa^5$-N,N,N,P,P-$^{Ph}_2{}^{PPr}$PDI)Mn, ($\kappa^5$-N,N,N,N,N-$^{PyEt}$PDI)Fe, ($\kappa^4$-N,N,N,P-$^{Ph}_2{}^{PPr}$PDI)Ni, and/or ($\kappa^4$-N,N,P,P-$^{Ph}_2{}^{PPr}$DI)Ni. In some embodiments, the Ni complexes described herein can be hydrosilylate acetophenone. When ($\kappa^4$-N,N,N,P-$^{Ph}_2{}^{PPr}$PDI)Ni was reacted with 10 equivalents of phenylsilane and 10 equivalents of acetophenone, the acetophenone was completely transformed after about 17 hours. When ($\kappa^4$-N,N,P,P-$^{Ph}_2{}^{PPr}$DI)Ni was reacted with 20 equivalents of phenylsilane and 20 equivalents of acetophenone, about 65% of the acetophenone was transformed after 24 hours. In another aspect, ($\kappa^5$-N,N,N,P,P-$^{Ph}_2{}^{PPr}$PDI)Mn exhibits exceptional turnover frequencies for ketone hydrosilylation at ambient temperature. When reacted with 1000 equivalents of phenylsilane and 1000 equivalents of acetophenone, acetophenone was completely transformed before analysis could be conducted (after 4 minutes/TOF>15,000 hr$^{-1}$). When reacted with 100 equivalents of phenylsilane and 300 equivalents of acetophenone, the acetophenone was completely consumed after 6 hrs (TOF≈50 hr$^{-1}$ with respect to acetophenone). When reacted with 100 equivalents of phenylsilane and 100 equivalents of diisopropylketone, the ketone was completely transformed before analysis could be conducted. When reacted with 100 equivalents of phenylsilane and 200 equivalents of diisopropylketone, the ketone was completely transformed after 30 minutes (TOF≈200 hr$^{-1}$ with respect to ketone). When reacted with 1000 equivalents of phenylsilane and 1000 equivalents of cyclohexanone, the ketone was completely transformed before analysis could be conducted (after 4 minutes/TOF>15,000 hr$^{-1}$). When reacted with 100 equivalents of phenylsilane and 300 equivalents of cyclohexanone, the cyclohexanone was completely consumed after 4 hrs (TOF≈75 hr$^{-1}$ with respect to cyclohexanone). When reacted with 100 equivalents of phenylsilane and 100 equivalents of 2-hexanone, the 2-hexanone was completely consumed after 10 min (TOF≈600 hr$^{-1}$ with respect to 2-hexanone). When reacted with 10 equivalents of phenylsilane and 10 equivalents of benzophenone, about 90% of the benzophenone was transformed after 24 hours.

In some embodiments, ($\kappa^5$-N,N,N,N,N-$^{PyEt}$PDI)Fe was found to mediate the hydrosilylation of ketones. When reacted with 10 equivalents of phenylsilane and 10 equivalents of acetophenone at ambient temperature, the acetophenone was completely transformed after 1 hour. When reacted with 10 equivalents of phenylsilane and 10 equivalents of cyclohexanone at ambient temperature, the cyclohexanone was completely transformed after 1 hour. When reacted with 10 equivalents of phenylsilane and 10 equivalents of diisopropylketone at 80° C., about 45% of the diisopropylketone was transformed after 13 hours.

In some embodiments, $(\kappa^5\text{-N,N,N,P,P-}{}^{Ph}{}_2{}^{PPr}\text{PDI})\text{Mn}$ was found to catalyze both the hydrosilylation and reductive cleavage of ethyl acetate. When reacted with 20 equivalents of ethyl acetate in the presence of 20 equivalents of phenylsilane, the ethyl acetate was completely transformed after 5.5 hours and the only organic product observed by NMR spectroscopy was $\text{PhSi(OEt)}_3$.

In some embodiments, $[(\kappa^5\text{-N,N,N,P,P-}{}^{Ph}{}_2{}^{PPr}\text{PDI})\text{Co}][\text{Cl}]$, $(\kappa^5\text{-N,N,N,N,N-}{}^{PyEt}\text{PDI})\text{Fe}$ and/or $(\kappa^4\text{-N,N,N,P-}{}^{Ph}{}_2{}^{PPr}\text{PDI})\text{Ni}$ can be used to catalyze the hydrosilylation of alkynes. When $[(\kappa^5\text{-N,N,N,P,P-}{}^{Ph}{}_2{}^{PPr}\text{PDI})\text{Co}][\text{Cl}]$ was reacted with 200 equivalents of phenylsilane and 200 equivalents of phenylacetylene at ambient temperature, the phenylacetylene was completely transformed into a mixture of alkene containing products after 24 hours (TOF≈8 hr$^{-1}$). When $(\kappa^5\text{-N,N,N,N,N-}{}^{PyEt}\text{PDI})\text{Fe}$ was reacted with 10 equivalents of phenylsilane and 10 equivalents of phenylacetylene at 65° C., the phenylacetylene was completely transformed into a mixture of alkene containing products after 25 minutes (TOF≈20 hr$^{-1}$). When reacted with 10 equivalents of phenylsilane and 10 equivalents of trimethylsilylacetylene at 65° C., about 91% of the trimethylsilylacetylene was transformed after 10 hours. When reacted with 10 equivalents of phenylsilane and 10 equivalents of 3-hexyne at 85° C., about 44% of the 3-hexyne was transformed after 5 hours. In summary, $(\kappa^4\text{-N,N,N,P-}{}^{Ph}{}_2{}^{PPr}\text{PDI})\text{Ni}$ was found to catalyze the hydrosilylation of phenylacetylene at ambient temperature. When reacted with 20 equivalents of phenylsilane and 20 equivalents of phenylacetylene, the phenylacetylene was completely transformed after 26 hours.

In some embodiments, the materials described herein rely on one or more supporting ligands that are coordinated in a $\kappa^4$- or $\kappa^5$-fashion, so as to allow for the development of catalysts having lower activation barriers. In other embodiments, the chelating arms of such materials can stabilize intermediates produced during a reaction process.

In some embodiments, the present disclosure provides a redox non-innocent PDI ligand that is capable of coordinating to a metal center beyond the historically investigated $\kappa^3\text{-N,N,N-PDI}$ core. In some embodiments, such a chelate would be less susceptible to dissociation (due to the chelate effect) and could circumvent the need for steric bulk in catalyst design.

In some embodiments, the catalyst materials described herein can provide equal and/or improved performance as compared to more expensive precious metal catalysts currently used. In some embodiments, the inventive materials can exhibit minimal or negligible toxicity, as compared to conventional platinum containing catalysts.

In some embodiments, the properties of the Mn, Fe, Co, and Ni complexes of the invention accurately mirror those of rhodium, which is easier to study since it has a tendency to form diamagnetic complexes.

As with Mn, Fe, Co, and Ni, bulky aryl imine substituents have been the current focus of (PDI)Rh chemistry. While steric protection has allowed for the isolation of an unusual 14-electron $(\kappa^3\text{-N,N,N-PDI})\text{Rh}$ cation (FIG. 1, left) following the addition of $\text{NaB(Ar')}_4$ [Ar'=3,5-bis(trifluoromethyl)phenyl] to the respective monochloride complex, the reactivity observed for $(^{Ar}\text{PDI})\text{RhCl}$ complexes has remained relatively undistinguished from the prior art on $(^R\text{PDI})\text{RhCl}$ complexes bearing non-coordinating alkyl-substituted arms.

Given the complexes illustrated in FIG. 1, PDI imine substituents can, in various aspects, be fitted with σ-donor atoms and tailored such that they can coordinate to rhodium beyond the ligand's terdentate redox-active core, potentially forcing reduction of the chelate.

In some embodiments, $^R$PDI ligands with imine substituents that have an ethyl or propyl bridge to a remote tertiary amine donor were synthesized. In another aspect, the amine substituents were varied to include either methyl or isopropyl groups. As illustrated in Eq. 1, the condensation of 2,6-diacetylpyridine with 2 eq. of either N,N-diisopropyl-1,2-ethanediamine or N,N-dimethyl-1,3-propanediamine allowed the preparation of 2,6-((($\text{CH}_3)_2\text{CH})_2\text{NCH}_2\text{CH}_2\text{N}=\text{C}(\text{CH}_2))_2\text{C}_5\text{H}_3\text{N}$ [$^{iPr}{}_2{}^{NEt}\text{PDI}$] and 2,6-(($\text{CH}_3)_2\text{NCH}_2\text{CH}_2\text{CH}_2\text{N}=\text{C}(\text{CH}_3))_2\text{C}_5\text{H}_3\text{N}$ [$^{Me}{}_2{}^{NPr}\text{PDI}$], respectively.

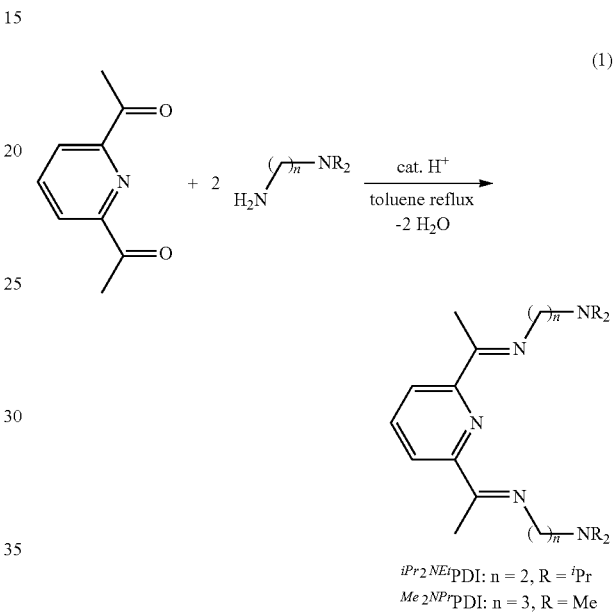

$^{iPr2NEt}$PDI: n = 2, R = $^i$Pr
$^{Me2NPr}$PDI: n = 3, R = Me

Several 4-coordinate (PDI)RhCl complexes have been prepared following PDI ligand addition to a commercially available [(olefin)$_2$RhCl]$_2$ starting material. Although square planar d$^8$ complexes of this type are energetically opposed to maintaining coordination to a fifth ligand, a sufficiently donating imine substituent functionality can, in one aspect, allow $\kappa^5$-PDI coordination. Additionally, since the redox-active core of PDI ligands is capable of accepting two electrons from a metal center, accessing a formally 20-electron ($\kappa^5$-PDI)RhCl complex featuring a chelate dianion can be possible. Adding either $^{iPr}{}_2{}^{NEt}$PDI or $^{Me}{}_2{}^{NPr}$PDI to 0.5 eq. of [(COD)RhCl]$_2$ in toluene solution at ambient temperature afforded a dark green solution, indicative of 4-coordinate (PDI)RhCl complex formation. After stirring for 24 hours, evacuation of the solvent followed by washing of the solid with pentane allowed the isolation of ($^{iPr}{}_2{}^{NEt}$PDI)RhCl (1-Cl) and ($^{Me}{}_2{}^{NPr}$PDI)RhCl (2-Cl), respectively (Eq. 2).

Figure 7:
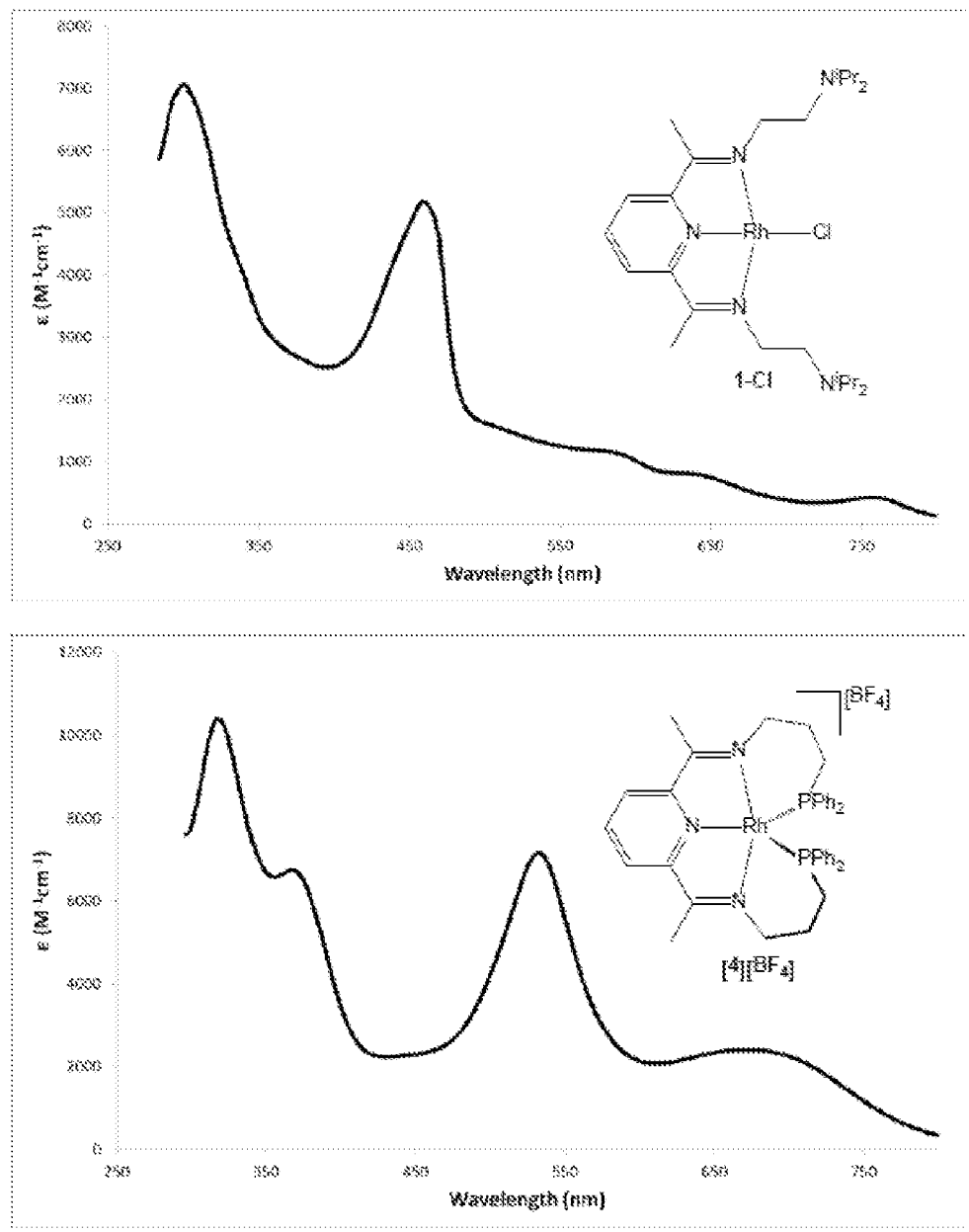
FIG. 7 illustrates UV-Vis spectra of 1-Cl (top, in toluene) and [4][$BF_4$] (bottom, in DMSO), in accordance with various aspects of the present disclosure.

No evidence for ligand asymmetry resulting from the coordination of one chelate arm was observed by $^1$H and $^{13}$C NMR spectroscopy, further supporting the square planar formulation of these complexes. In the electronic spectrum of 1-Cl (see FIG. 7), two pronounced charge transfer bands were observed at 302 nm (ϵ=7200 M$^{-1}$ cm$^{-1}$) and 452 nm (ϵ=4800 M$^{-1}$ cm$^{-1}$) that are likely due to backbonding into the PDI chelate.

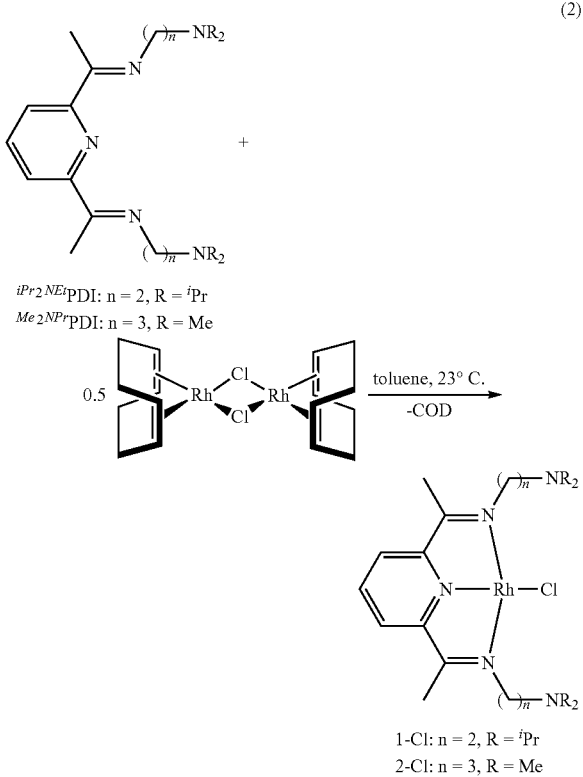

*iPr2NEt*PDI: n = 2, R = *i*Pr
*Me2NPr*PDI: n = 3, R = Me

1-Cl: n = 2, R = *i*Pr
2-Cl: n = 3, R = Me

Figure 2:
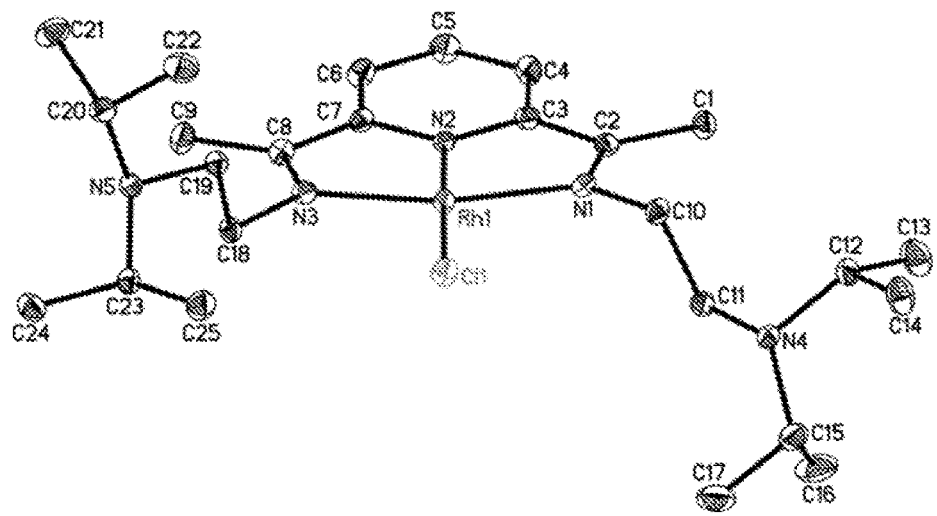
FIG. 2 illustrates the solid state structure of 1-Cl with 30% probability ellipsoids (hydrogen atoms omitted for clarity), in accordance with various aspects of the present disclosure.

Compounds were subjected to analysis by single crystal X-ray diffraction to verify that the PDI ligand amine arms were non-coordinating. Single crystals of 1-Cl suitable for X-ray diffraction were grown from a concentrated solution of the complex in toluene/pentane at −35° C. As expected, solving the solid state structure of 1-Cl (FIG. 2) confirmed that the diisopropylaminoethyl arms of the PDI chelate were not coordinated to the rhodium center. The metrical parameters determined for 1-Cl (Table 1) indicate that the geometry about the metal is distorted from idealized square planar with an N(1)-Rh(1)-N(3) angle of 159.19(11)°.

TABLE 1

Selected bond lengths (Å) and angles (°) for 1-Cl and 2-Cl

|  | 1-Cl | 2-Cl |
| --- | --- | --- |
| Rh(1)—N(1) | 2.030(3) | 2.030(3) |
| Rh(1)—N(2) | 1.884(3) | 1.889(3) |
| Rh(1)—N(3) | 2.030(3) | 2.032(3) |
| Rh(1)—Cl(1) | 2.3476(9) | 2.3621(9) |
| N(1)—C(2) | 1.316(4) | 1.316(5) |
| N(3)—C(8) | 1.303(4) | 1.303(5) |
| C(2)—C(3) | 1.452(5) | 1.462(5) |
| C(7)—C(8) | 1.467(4) | 1.475(5) |
| N(1)—Rh(1)—N(2) | 79.76(11) | 79.27(13) |
| N(1)—Rh(1)—N(3) | 159.19(11) | 159.13(12) |
| N(2)—Rh(1)—N(3) | 79.44(11) | 79.86(13) |
| N(2)—Rh(1)—Cl(1) | 178.68(8) | 176.92(9) |

Evidence for imine bond elongation was observed with N(1)-C(2) and N(3)-C(8) distances of 1.316(4) Å and 1.303(4) Å, respectively. Shortening of the $C_{imine}$-$C_{pyridine}$ bonds relative to the distances expected for a neutral chelate is also apparent with C(2)-C(3) and C(7)-C(8) distances of 1.452(5) Å and 1.467(4) Å, respectively. It is important to note that the Rh(1)-N(1), Rh(1)-N(2), and Rh(1)-N(3) distances of 2.030(3) Å, 1.884(3) Å, and 2.030(3) Å, respectively, are shorter than expected for a Rh(I) complex [in associated Rh(I) (imino)pyridine complexes, Rh-$N_{imine}$=2.248(4)-2.283(3) Å; Rh-$N_{pyridine}$=2.255(5)-2.267(3) Å] and are remarkably undistinguished from the same distances reported for related trivalent (PDI)Rh(Cl)$_2$(CH$_2$Cl) complexes.

Figure 3:
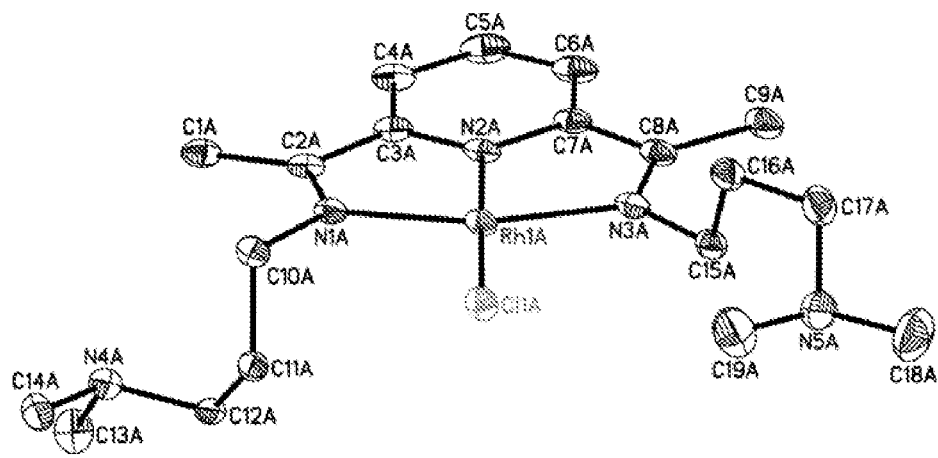
FIG. 3 illustrates the solid state structure of 2-Cl with 30% probability ellipsoids (one of two complexes in the asymmetric unit shown with hydrogen atoms omitted for clarity), in accordance with various aspects of the present disclosure.

The solid state structure of 2-Cl (FIG. 3) was also determined by single crystal X-ray diffraction. Similar to the molecular structure of 1-Cl, a pseudo square planar geometry about the metal center was observed with the chelate dimethylaminopropyl imine substituents clearly lying outside the bonding range of rhodium.

Importantly, this suggests that neither the isopropyl substituents nor the ethylene bridge in 1-Cl were responsible for the lack of pendent tertiary amine coordination. As shown in Table 1, the metrical parameters found for 2-Cl, including the Rh—N, $N_{imine}$-$C_{imine}$, and $C_{imine}$-$C_{pyridine}$ distances, are analogous to those determined for 2-Cl.

While the PDI chelate $N_{imine}$-$C_{imine}$ and $C_{imine}$-$C_{pyridine}$ distances determined for both 1-Cl and 2-Cl suggest an electronic structure consistent with a PDI radical monoanion that is antiferromagnetically coupled to a Rh(II) metal center, this possibility was first discarded for related ($^{Ar}$PDI) RhX (X=H, Me, Cl) complexes on the basis that they possess relatively normal $^1$H NMR spectra (minimal shift versus free ligand reference values) when compared to their cobalt congeners. In a more recent report by Burger and co-workers, a comprehensive and thorough investigation into the electronic structure of complexes of the general type (PDI)MX (M=Rh, Ir; X=NCO, N$_3$, Cl, Me, OMe, OH, NH$_2$) revealed significant metal-to-ligand backbonding into the symmetric rather than the asymmetric PDI π* orbital, as judged by DFT.

For (PDI)IrCl, Mulliken population analysis revealed that the electron density of the HOMO is nearly evenly distributed between the PDI ligand (45%) and the metal center (37%, $d_{xz}$), with the balance of charge localized on the chloride ligand. Extrapolating this knowledge to the solid state structures of 1-Cl and 2-Cl, we believe the electronic structure of these complexes is consistent with having significant π-backbonding from a Rh(I) center into a neutral PDI ligand rather than a Rh(III) center supported by a PDI dianion. This assessment is supported by the fact that second row transition metals have lower pairing energies and d-orbitals that more efficiently overlap with ligand-based π-orbitals than their first row congeners (due to radial expansion), decreasing the likelihood of populating a destabilized orbital comprising the antibonding combination of π-PDI and Rh 4d orbitals.

Since repulsion of the amine donors by the filled $d_{z^2}$ orbital of rhodium could prevent coordination of a fifth or sixth ligand, the preparation of formal Rh(I) complexes featuring an outer-sphere anion was targeted. It was also anticipated that this approach would enable amine-functionalized PDI ligand arm coordination because [($^{iPr_2Ar}$PDI)Rh] [B(Ar')$_4$] (FIG. 1, left) is known to bind σ-donors including acetophenone and p-tolualdehyde.

Figure 8:
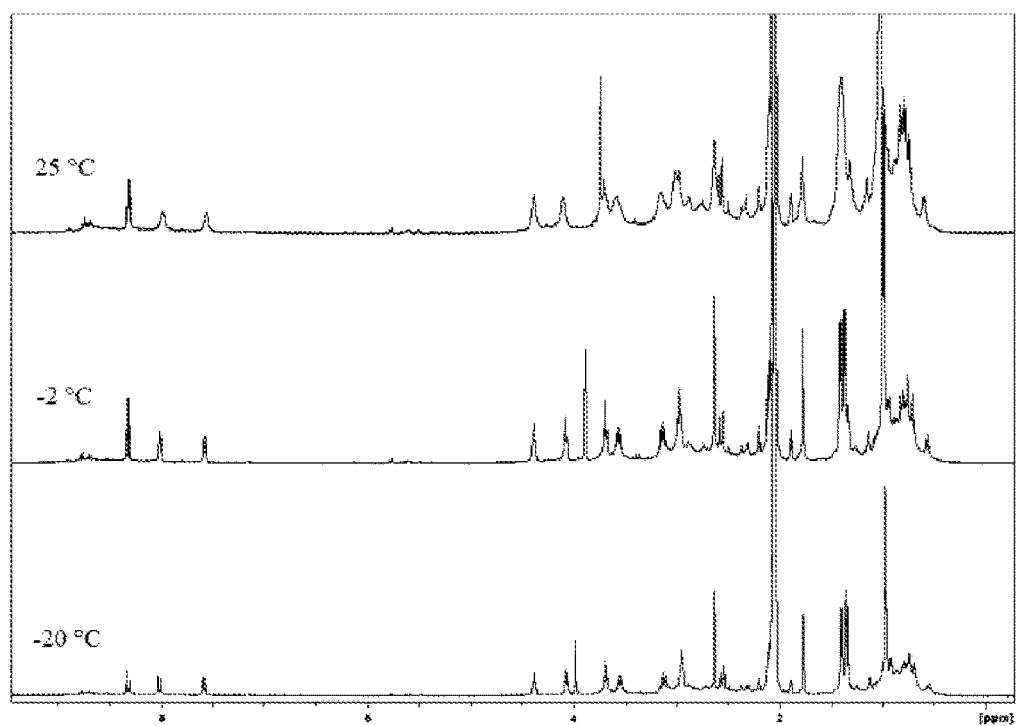
FIG. 8 illustrates the $^1$H NMR spectrum of [1][$BF_4$] in acetone-$d_6$ at 25° C., −2° C., and −20° C., in accordance with various aspects of the present disclosure.

Four-coordinate complexes of the type [($^{Ar}$PDI)Rh(THF)] [X] (where the outer-sphere anion X=OTf or Al(OC$_4$F$_9$)$_4$) have also been well-investigated. Adding a slight excess of AgBF$_4$ to a solution of 1-Cl in acetone-d$_6$ allowed the observation of a low-symmetry complex featuring broadened $^1$H NMR resonances at ambient temperature (Eq. 3, left arrow). Cooling this solution to −20° C. (see FIG. 8) allowed observation of the slow exchange limit and verification of PDI ligand arm inequivalence by $^1$H and $^{13}$C NMR spectroscopy. These observations suggested that the resulting product, [($^{iPr}_2{}^{NEt}$PDI)Rh][BF$_4$] ([1][BF$_4$]), contains a tetradentate PDI chelate whereby diisopropylaminoethyl ligand arm exchange occurs in solution at ambient temperature. The preparation of [1][BF$_4$] was also achieved upon adding AgBF$_4$ directly to 0.5 eq. of [(COD)RhCl]$_2$, followed by the addition of $^{iPr}_2{}^{NEt}$PDI in THF solution (Eq. 3, right arrow).

these spectroscopic observations do not differentiate the roles of imine substituent arm length and steric bulk in substitution, it appears that functionalized PDI arms featuring either an ethyl- or propyl-bridge are capable of coordinating to a central rhodium atom.

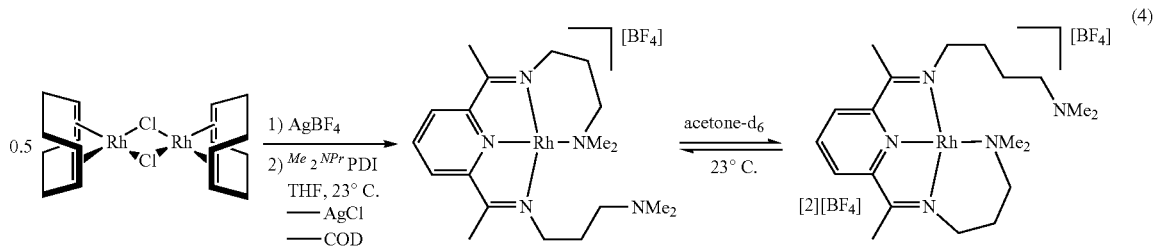

(4)

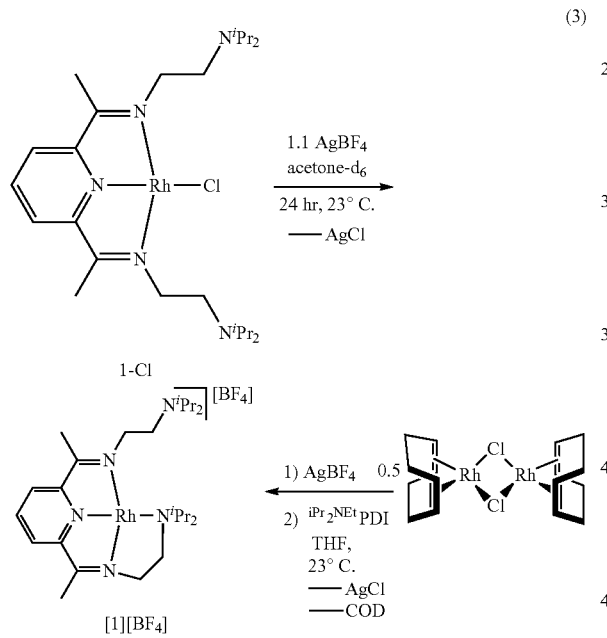

(3)

To determine if the sterically demanding isopropyl substituents in [1][BF$_4$] play a role in discouraging pentadentate $^N$PDI coordination, studies involving the related dimethylamino-substituted PDI ligand became warranted. Expectedly, the addition of $^{Me}_2{}^{NPr}$PDI following the reaction between AgBF$_4$ and 0.5 eq. of [(COD)RhCl]$_2$ resulted in the preparation of [($^{Me}_2{}^{NPr}$PDI)Rh][BF$_4$] ([2][BF$_4$]) (Eq. 4). Surprisingly, the ambient temperature $^1$H NMR spectrum of [2][BF$_4$] suggested that this complex was C$_{2v}$-symmetric, as only three methylene arm resonances were detected.

Figure 4:
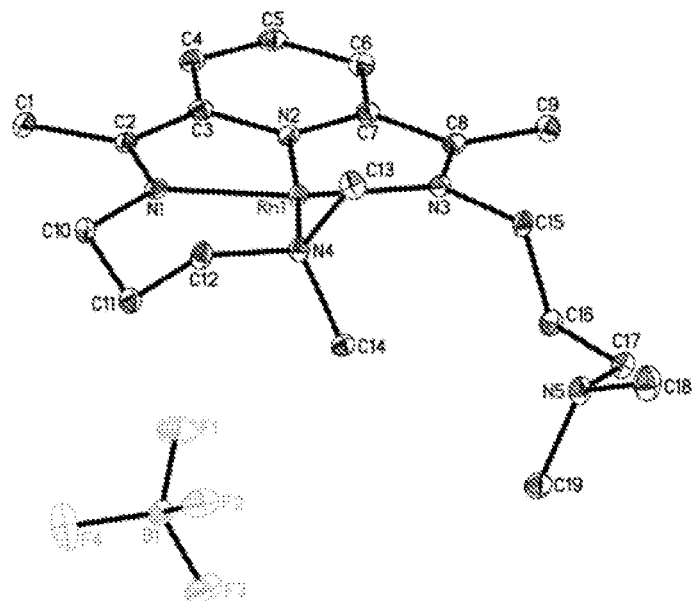
FIG. 4 illustrates the solid state structure of [2][$BF_4$] with 30% probability ellipsoids (hydrogen atoms omitted for clarity), in accordance with various aspects of the present disclosure.
Figure 9:
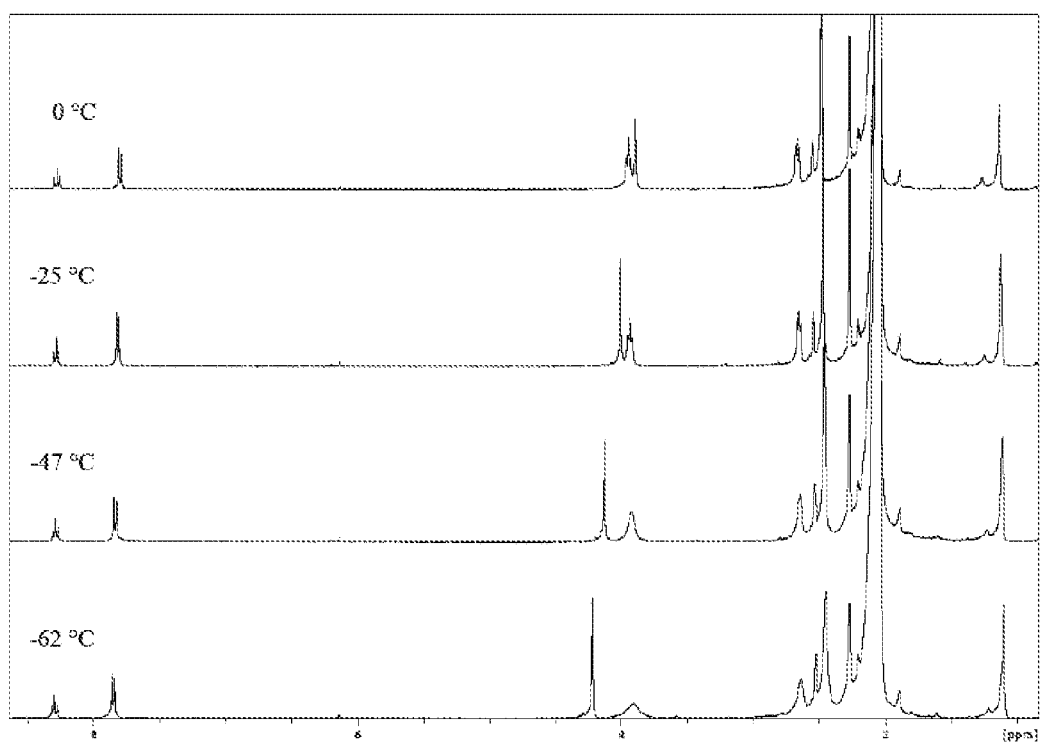
FIG. 9 illustrates the variable temperature $^1$H NMR spectrum of [2][$BF_4$] in acetone-$d_6$, in accordance with various aspects of the present disclosure.

Upon closer inspection, it was realized that if persistent $\kappa^5$-N,N,N,N,N-PDI coordination had been achieved, twice as many chelate arm resonances would be observed. Cooling an acetone-d$_6$ solution of [2][BF$_4$] to −62° C. resulted in broadening of the imine substituent resonances (FIG. 9), and although the slow exchange limit was not reached, it is clear that this complex undergoes chelate arm exchange at a faster rate than [1][BF$_4$] in solution at ambient temperature. While To substantiate these claims, [2][BF$_4$] was recrystallized from an acetone/pentane mixture at −35° C. and single crystals suitable for X-ray diffraction were obtained. As anticipated, the molecular structure determination of [2][BF$_4$] uncovered a $\kappa^4$-PDI chelate, with an overall coordination geometry that is best described as pseudo square planar (FIG. 4). The metrical parameters found for this complex (Table 2) expose a deviation from linearity between the central rhodium atom and chelate imine nitrogen atoms with an N(1)-Rh(1)-N(3) angle of 157.74(9)°. Although less pronounced, a deviation from linearity along the pyridine-Rh-amine axis can also be seen with an N(2)-Rh(1)-N(4) angle of 173.11(9)°. Notably, the tertiary amine nitrogen atom is located further from the Rh center than the PDI chelate donors due to its lack of π-acidity. As with 1-Cl and 2-Cl, slightly elongated N$_{imine}$-C$_{imine}$ distances of 1.309(3) Å and 1.305(3) Å with shortened C$_{imine}$-C$_{pyridine}$ distances of 1.460(4) Å and 1.475(4) Å are observed in the solid state structure of [2][BF$_4$].

TABLE 2

Selected bond lengths (Å) and angles (°) for [2][BF$_4$]

| Rh(1)—N(1) | 2.016(2) | N(1)—Rh(1)—N(2) | 79.52(9) |
|---|---|---|---|
| Rh(1)—N(2) | 1.902(2) | N(1)—Rh(1)—N(3) | 157.74(9) |
| Rh(1)—N(3) | 2.084(2) | N(1)—Rh(1)—N(4) | 96.96(9) |
| Rh(1)—N(4) | 2.143(2) | N(2)—Rh(1)—N(3) | 78.49(9) |
| N(1)—C(2) | 1.309(3) | N(2)—Rh(1)—N(4) | 173.11(9) |
| N(3)—C(8) | 1.305(3) | | |
| C(2)—C(3) | 1.460(4) | | |
| C(7)—C(8) | 1.475(4) | | |

At this stage, it was theorized that replacing the pendent amine donors with stronger σ-donating functionalities might allow for pentadentate PDI ligand coordination to a central rhodium chloride moiety, affording pseudo octahedral ($\kappa^5$-PDI)RhCl complexes. Isolating formal 20-electron complexes of this type was of particular interest from the outset of the study, as they would likely feature a Rh(III) center supported by a true PDI dianion. Keeping in mind that ethyl-([1][BF$_4$]) and propyl-bridged ([2][BF$_4$]) amine arms are capable of coordinating to rhodium, bis(imino)pyridine ligands featuring alkylphosphine imine substituents were designed. In contrast to the alkylamine-substituted PDI ligands, the condensation of 2,6-diacetylpyridine with 2 equivalents of either 2-(diphenylphosphino)-1-ethylamine or 3-(diphenylphosphino)-1-propylamine to synthesize ((C$_6$H$_5$)$_2$PCH$_2$CH$_2$N═C(CH$_3$))$_2$C$_5$H$_3$N [$^{Ph}_2{}^{PEt}$PDI] and 2,6-((C$_6$H$_5$)$_2$PCH$_2$CH$_2$CH$_2$N═C(CH$_3$))$_2$C$_5$H$_3$N

[$^{Ph}_2{}^{PPr}$PDI], respectively, was conducted in a thick-walled glass bomb in the presence of 4 Å molecular sieves (Eq. 5).

Following filtration and solvent removal, recrystallization of either ligand from a concentrated ether solution at −35° C. afforded analytically pure yellow crystals as judged by elemental analysis and multinuclear NMR spectroscopy. While $^{Ph2PPr}$PDI coordination to copper has been explored, the successful isolation of $^{Ph2PEt}$PDI and $^{Ph2PPr}$PDI had not been previously achieved.

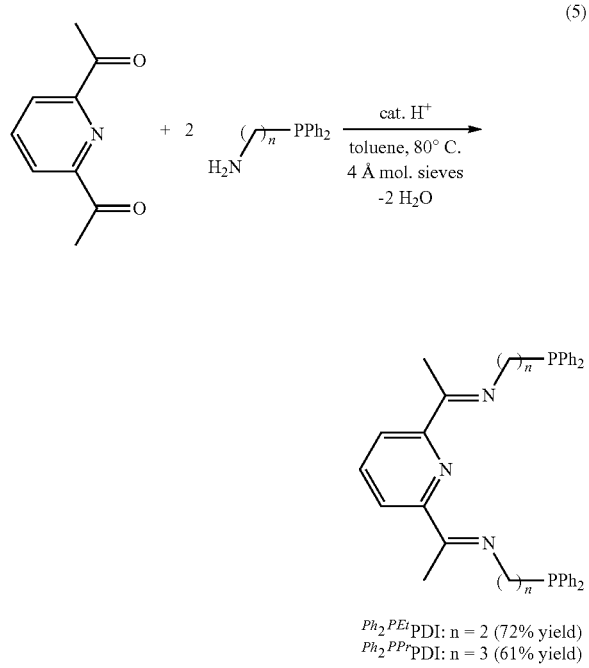

$^{Ph_2PEt}$PDI: n = 2 (72% yield)
$^{Ph_2PPr}$PDI: n = 3 (61% yield)

With the desired phosphinoalkyl-substituted PDI chelates in hand, their metallation onto rhodium was investigated. Notably, the addition of $^{Ph}_2{}^{PEt}$PDI to 0.5 equivalents of [(COD)RhCl]$_2$ in toluene (Eq. 6) resulted in an immediate color change from the initial orange solution to dark purple. As the reaction progressed at ambient temperature, purple precipitate began to form which was collected after stirring for two days. After washing the solid with several pentane fractions to remove any residual COD ligand, analysis of the precipitate by $^1$H NMR spectroscopy revealed four chelate arm resonances, suggesting that at least one phosphinoethyl arm was coordinated to the rhodium center. Surprisingly, the $^1$H NMR spectrum of this complex uncovered $^{31}$P-coupling to the PDI backbone methyl (t, 6H) and p-pyridine (m, 1H) resonances in addition to the ethyl-bridged chelate arms, a feature not observed for the free chelates. Close investigation of this complex by $^{13}$C NMR spectroscopy revealed only two methylene resonances, confirming that both PDI arms were bound to rhodium. As anticipated, the $^{31}$P NMR spectrum of this complex in DMSO-d$_6$ features only a doublet at 43.64 ppm with J$_{RhP}$ coupling of 135.4 Hz, consistent with κ$^5$-N,N,N,P,P-PDI coordination.

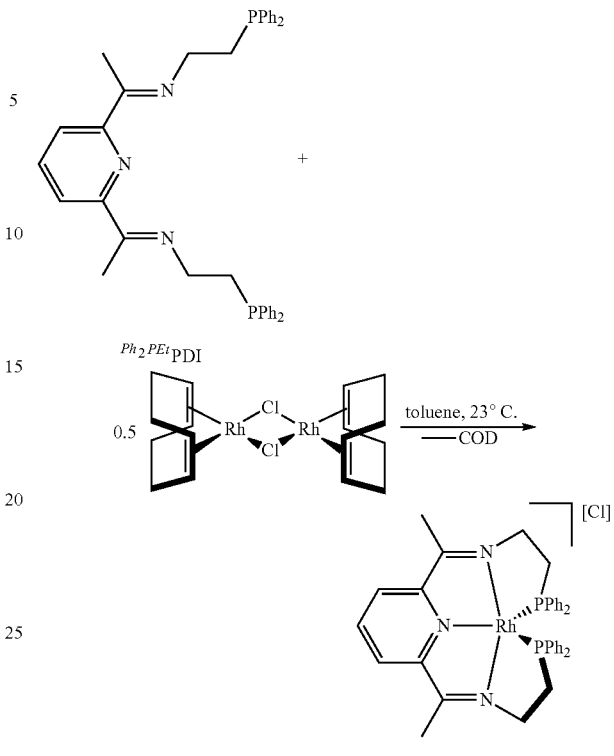

Figure 5:
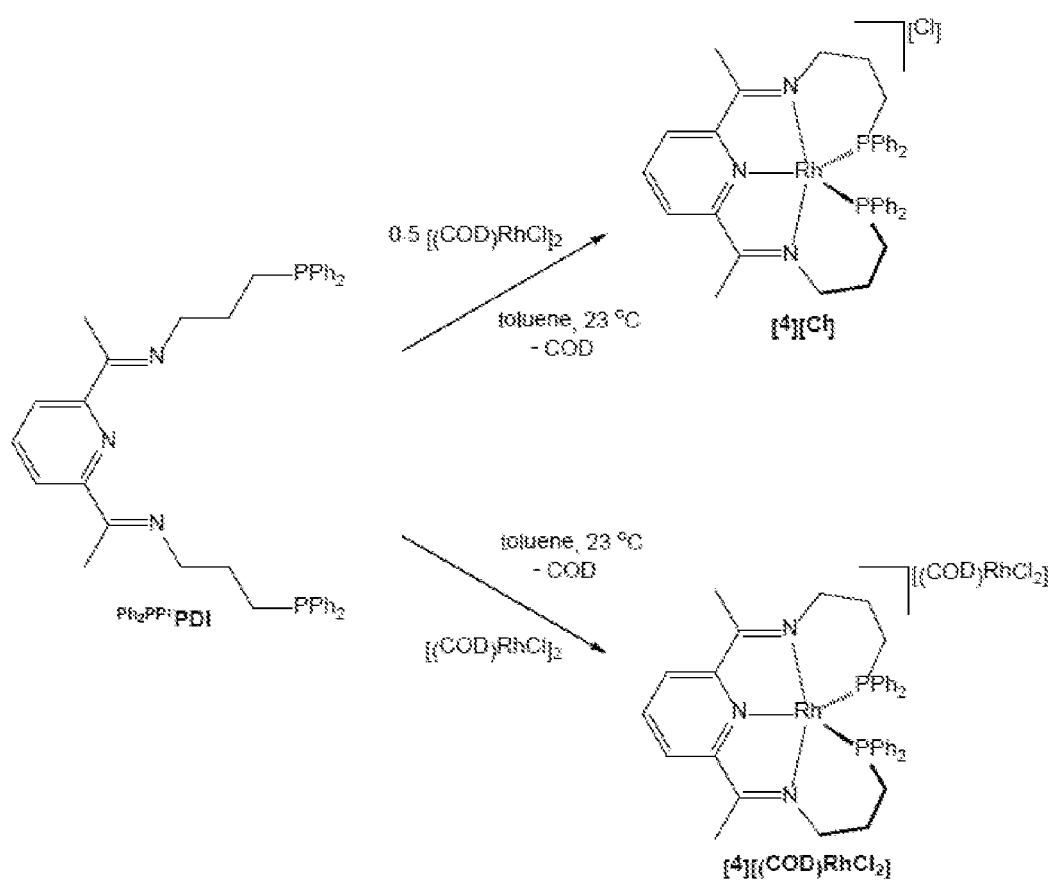
FIG. 5 illustrates an exemplary preparation of cationic rhodium complexes featuring a 5-coordinate $^{Ph}_2{}^{PPr}$PDI chelate, in accordance with various aspects of the present disclosure.

Although the composition of this complex was well understood, its relative lack of solubility in a range of solvents initially suggested that the chloride ligand was no longer an inner-sphere ligand, leading to the assignment of this complex as [($^{Ph}_2{}^{PEt}$PDI)Rh][Cl] ([3][Cl]). Similar to the metallation of $^{Ph}_2{}^{PEt}$PDI, the addition of $^{Ph}_2{}^{PPr}$PDI to 0.5 equivalents of [(COD)RhCl]$_2$ afforded a purple solid identified as [($^{Ph}_2{}^{PPr}$PDI)Rh][Cl] ([4][Cl]) (FIG. 5, top), as judged by multinuclear NMR spectroscopy. The UV-visible spectrum of [4][Cl] in DMSO solution was largely different than the one collected for 1-Cl, with charge transfer bands observed at 317 nm (ε=12400 M$^{-1}$ cm$^{-1}$), 362 nm (ε=8000 M$^{-1}$ cm$^{-1}$), 530 nm (ε=8800 M$^{-1}$ cm$^{-1}$), and 671 nm (ε=2900 M$^{-1}$ cm$^{-1}$) (FIG. 7), providing additional evidence of phosphine ligand arm coordination. Because neither [3][Cl] nor [4][Cl] were readily soluble in common crystallization solvents such as toluene, tetrahydrofuran, or acetone, related compounds featuring better solubility were desired so that the presence of an outer-sphere anion could be confirmed by single crystal X-ray diffraction.

Since it was observed that [4][Cl] appeared soluble in toluene at early reaction times and later precipitated from solution, the metallation reaction was adjusted such that a stoichiometric amount of $^{Ph}_2{}^{PPr}$PDI was added to [(COD) RhCl]$_2$ (i.e., one molecule of ligand per two rhodium equivalents). While this reaction (FIG. 5, bottom) also resulted in the formation of a purple precipitate, complete consumption of the [(COD)RhCl]$_2$ starting material had been achieved. Realizing that the stoichiometric addition of a chelating ligand to [(COD)RhCl]$_2$ is well-known to result in the formation of ionic complexes featuring a [(COD)RhCl$_2$] anion, the resulting purple precipitate was presumed to be [($^{Ph}_2{}^{PPr}$PDI)Rh][(COD)RhCl$_2$] ([4][(COD)RhCl$_2$]). This formulation was further supported by elemental analysis and multinuclear NMR spectroscopy.

Figure 6:
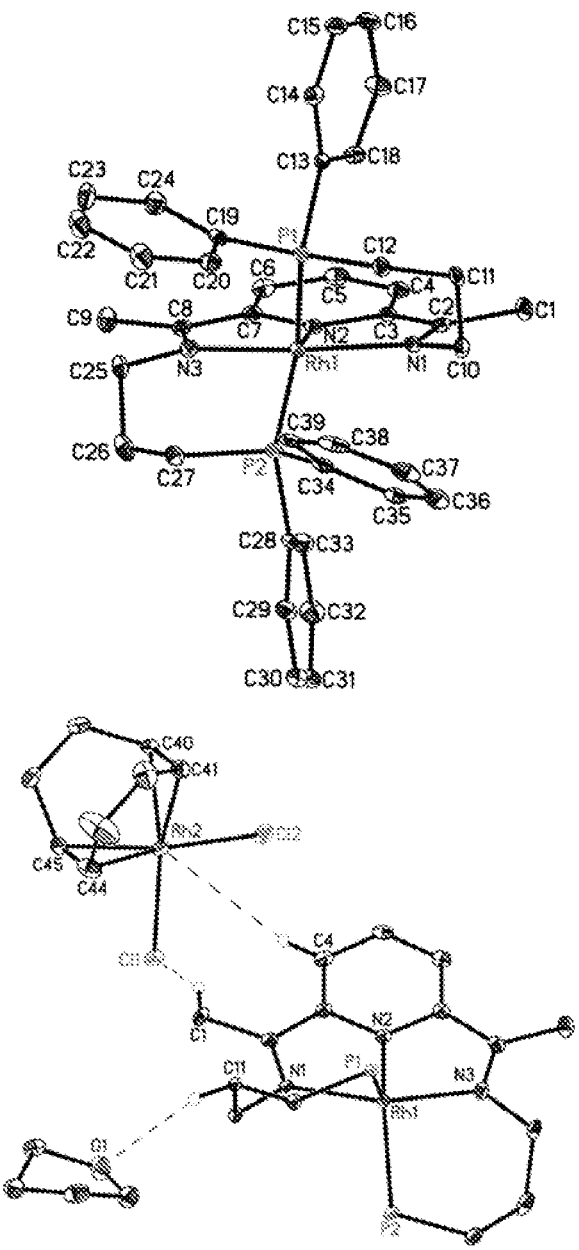
FIG. 6 illustrates the solid state structure of [4][(COD)RhCl$_2$] with 30% probability ellipsoids; the [($\kappa^5$-N,N,N,P,P-$^{Ph}_2{}^{PPr}$PDI)Rh] cation is illustrated without hydrogen atoms, co-crystallized tetrahydrofuran molecule, and (COD)RhCl$_2$ anion for clarity (top); and the spatial relationship of all three structure components shown with close contacts between PDI chelate hydrogen atoms, the cation, and co-crystallized THF molecule (bottom); illustrations prepared using symmetry operators (1-x, 1-y, 1-z) for the cation and THF molecule, and (2-x, 1-y, 1-z) for (COD)RhCl$_2$, in accordance with various aspects of the present disclosure.

Fortunately, [4][(COD)RhCl$_2$] exhibited slightly better solubility than [4][Cl] and single crystals suitable for X-ray diffraction were obtained from the slow evaporation of a THF solution at ambient temperature. Solving the molecular structure of [4][(COD)RhCl$_2$] (FIG. 6) confirmed that this complex features κ$^5$-N,N,N,P,P-PDI ligand coordination in addition to an outer-sphere (COD)RhCl$_2$ anion. The overall coordination geometry about the PDI-supported rhodium center is best described as pseudo trigonal bipyramidal, and the relevant metrical parameters for [4][(COD)RhCl$_2$] are displayed in Table 3. Although the anticipated deviation from linearity between the rhodium center and imine nitrogen donors is observed with an N(1)-Rh(1)-N(3) angle of 157.10(12)°, there are also deviations from trigonal bipyramidal geometry in the equatorial plane with P(1)-Rh(1)-P(2) and N(2)-Rh(1)-P(2) angles of 99.06(3)° and 141.15(8)°, respectively. Relative to the solid state structures of 1-Cl, 2-Cl, and [2][BF$_4$], evidence for increased backbonding into the redox-active core of the PDI is observed with C(2)-C(3) and C(7)-C(8) bond distances of 1.427(5) Å and 1.435(5) Å, respectively, consistent with an increase in electron density upon coordination of two strongly-donating phosphine arms. This feature is less pronounced when considering the N(1)-C(2) and N(3)-C(8) distances of 1.335(5) Å and 1.322(5) Å; however, this observation is not overly surprising since the symmetric π* orbital on PDI is heavily localized at the $C_{imine}$-$C_{pyridine}$ bonds. Even though these metrical parameters are more consistent with a PDI dianion than those determined for the other structures discussed in this manuscript, it remains unlikely that [4][(COD)RhCl$_2$] possesses a true Rh(III) center. The metrical parameters of the (COD)RhCl$_2$ anion (Table 3) are unremarkable in the sense that the overall geometry about rhodium is near square planar and backbonding into the COD ligand is responsible for lengthening of the C(40)-C(41) and C(44)-C(45) bonds to 1.417(6) Å and 1.402(6) Å, respectively.

TABLE 3

Selected bond lengths (Å) and angles (°) for [4][(COD)]RhCl$_2$]

| Rh(1)—N(1) | 2.029(3) | N(1)—Rh(1)—N(2) | 78.95(12) |
|---|---|---|---|
| Rh(1)—N(2) | 1.926(3) | N(1)—Rh(1)—N(3) | 157.10(12) |
| Rh(1)—N(3) | 2.046(3) | N(1)—Rh(1)—P(1) | 88.01(8) |
| Rh(1)—P(1) | 2.2926(9) | N(1)—Rh(1)—P(2) | 103.62(9) |
| Rh(1)—P(2) | 2.3101(10) | N(2)—Rh(1)—P(1) | 119.79(8) |
| N(1)—C(2) | 1.335(5) | N(2)—Rh(1)—P(2) | 141.15(8) |
| N(3)—C(8) | 1.322(5) | P(1)—Rh(1)—P(2) | 99.06(3) |
| C(2)—C(3) | 1.427(5) | | |
| C(7)—C(8) | 1.435(5) | | |
| Rh(2)—Cl(1) | 2.3847(9) | Cl(1)—Rh(2)—Cl(2) | 90.56(3) |
| Rh(2)—Cl(2) | 2.3773(10) | C(40)—Rh(2)—C(45) | 82.43(16) |
| Rh(2)—C(40) | 2.104(4) | C(41)—Rh(2)—C(44) | 81.91(16) |
| Rh(2)—C(41) | 2.100(4) | | |
| Rh(2)—C(44) | 2.099(4) | | |
| Rh(2)—C(45) | 2.102(4) | | |
| C(40)—C(41) | 1.417(6) | | |
| C(44)—C(45) | 1.402(6) | | |

Finally, κ$^5$-N,N,N,P,P-PDI complexes featuring a tetrafluoroborate counter ion were prepared in a similar fashion to [1][BF$_4$] and [2][BF$_4$]. After filtering the reaction between AgBF$_4$ and 0.5 equivalents of [(COD)RhCl]$_2$, the addition of either $^{Ph_2PEt}$PDI or $^{Ph_2PPr}$PDI (Eq. 7) allowed the preparation of purple [($^{Ph_2PEt}$PDI)Rh][BF$_4$] ([3][BF$_4$]) or [($^{Ph_2PPr}$PDI)Rh][BF$_4$] ([4][BF$_4$]), respectively. Although they feature bands with slightly different $\lambda_{max}$ values and extinction coefficients, the UV-vis spectra of [4][Cl] and [4][BF$_4$] were found to be relatively indistinguishable (Table 4).

TABLE 4

Wavelengths of maximum absorption ($\lambda_{max}$) and extinction coefficients (ε) for each complex analyzed by UV-vis spectroscopy.

| Complex | $\lambda_{max}$ (nm) | ε (M$^{-1}$ cm$^{-1}$) |
|---|---|---|
| 1-Cl | 302 | 7200 |
| | 452 | 4800 |
| | 581 | 1400 |
| | 647 | 1000 |
| | 764 | 580 |
| [4][Cl] | 317 | 12400 |
| | 362 | 8000 |
| | 530 | 8800 |
| | 671 | 2900 |
| [4][BF$_4$] | 317 | 8900 |
| | 368 | 6600 |
| | 530 | 6600 |
| | 671 | 3400 |

Figure 10:
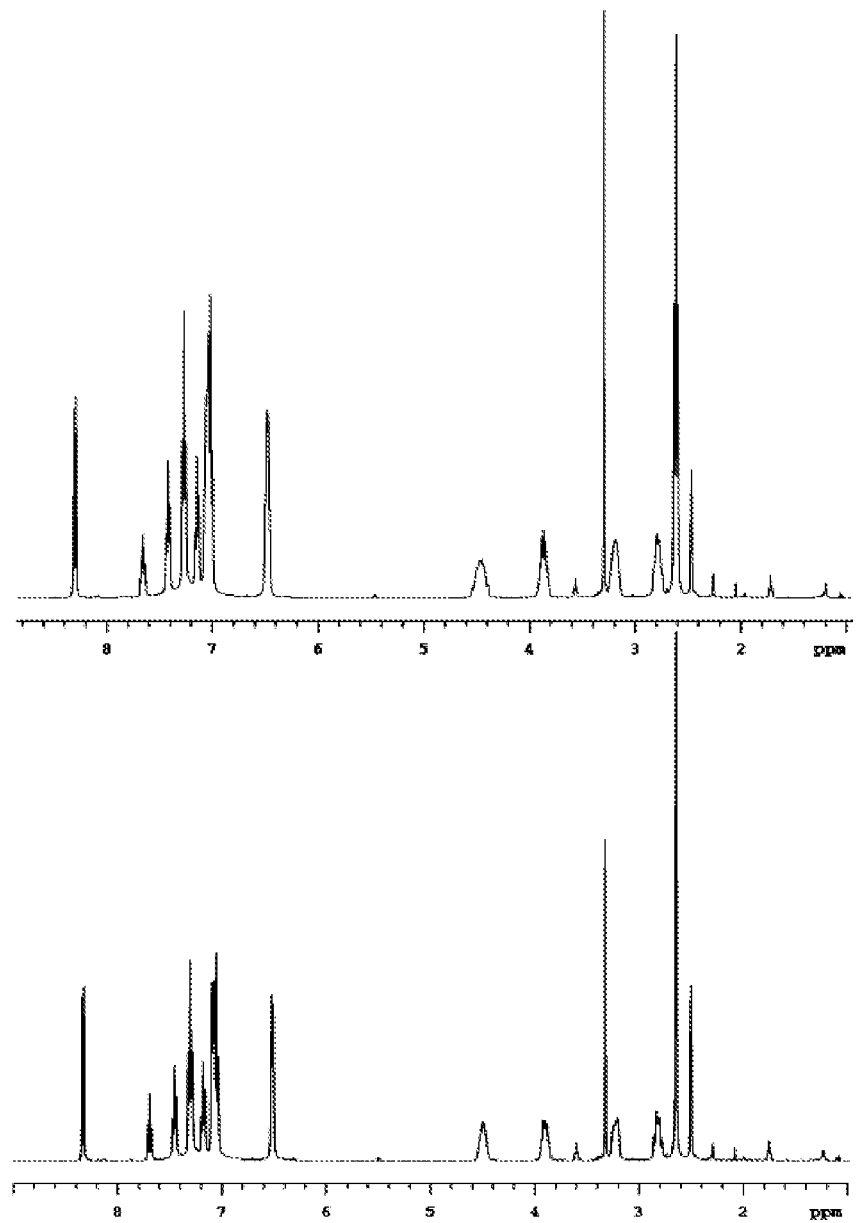
FIG. 10 illustrates the $^1$H NMR (top) and $^1$H{$^{31}$P} NMR (bottom) spectra of [3][Cl] in DMSO-$d_6$, in accordance with various aspects of the present disclosure.

The $^1$H, $^{13}$C, and $^{31}$P NMR spectra of [3][BF$_4$] and [4][BF$_4$] were directly comparable to those obtained for [3][Cl] and [4][Cl], respectively, and the $^1$H{$^{31}$P} NMR spectrum of both tetrafluoroborate complexes revealed resolved PDI p-pyridine (t, 1H) and backbone methyl (s, 6H) resonances, confirming the observation of phosphine-derived J coupling (for representative spectra, see FIG. 10). Importantly, the synthesis of these complexes directly from [(COD)RhCl]$_2$ further emphasizes the propensity of both $^{Ph_2PEt}$PDI and $^{Ph_2PPr}$PDI to form pentadentate coordination complexes.

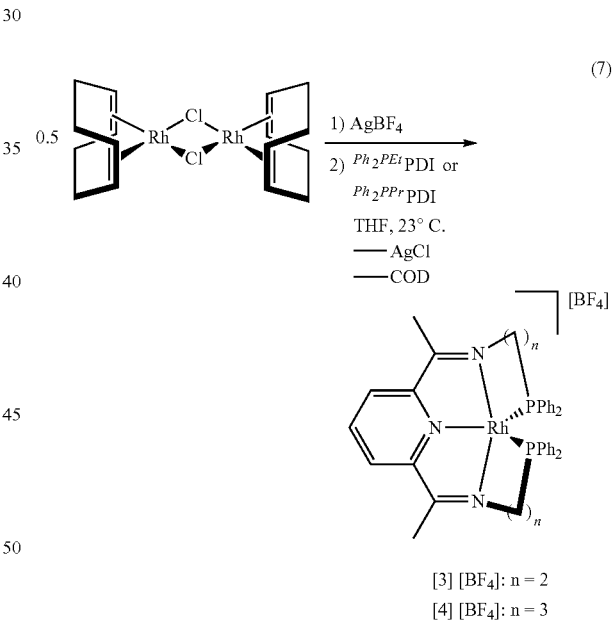

Since ethyl- and propyl-bridged PDI donor arms were found to coordinate to rhodium, and allow for the isolation of complexes featuring either κ$^4$-N,N,N,N- or κ$^5$-N,N,N,P,P-PDI chelation, it is worth discussing the impact this investigation can have when considering ligands of this nature for homogeneous catalytic applications. As evidence for chelate arm exchange was observed for each amine-bound κ$^4$-N,N,N,N-PDI complex, it is implied that weakly coordinating donor substituents of this type might readily dissociate to allow for a catalytic transformation while offering the potential to stabilize coordinatively unsaturated, high energy intermediates. On the other hand, while phosphine-substituted PDI ligands such as $^{Ph_2PEt}$PDI and $^{Ph}_2{}^{PPr}$PDI might be capable of stabilizing reactive precatalysts or intermediates, it is possible that the inclusion of strong field phosphine donors can completely prevent a targeted transformation from taking place. Fortunately, if pendent chelate arms are desired to improve the characteristics of a given PDI-supported catalyst, the imine substituents described in this manuscript can be modified to contain stronger or weaker donor atoms, longer or shorter bridges to those atoms, in addition to more or less bulky donor substituents with a range of electronic properties.

The first rhodium complexes featuring either a tetradentate or pentadentate redox-active bis(imino)pyridine ligand have been prepared and characterized using single crystal X-ray diffraction and a range of supporting techniques. Although not observed for neutral monochloride complexes, the coordination of tertiary amine functionalities allowed $\kappa^4$-N,N,N-PDI chelation when rhodium complexes featuring an outer-sphere tetrafluoroborate anion were prepared. In contrast, the metallation of $^P$PDI ligands onto [(COD)RhCl]$_2$ forced the chloride ligand to leave the rhodium coordination sphere, forming complexes featuring a pentadentate PDI ligand and either a [Cl]$^-$ or [(COD)RhCl$_2$]$^-$ counter ion. Knowing that the range of second generation PDI ligands described in this study are capable of $\kappa^4$- and $\kappa^5$-coordination to a metal center, it is believed that this approach to expanding redox-active ligand complexity can prove worthwhile for the optimization of current transition metal catalysts and inspire the development of new ones.

In certain other embodiments, the disclosed metal complexes are hydride-containing and hydride-derived kappa4- and kappa5-ligand metal complexes. As described in more detail in the Examples below, the efficient hydrosilylation of ketones using such metal complexes have been observed. In the presence of an equimolar amount of PhSiH$_3$ and 0.1 mol % of kappa5-N,N,N,P,P-$^{Ph}_2{}^{PPr}$PDIMnH, 87% conversion of acetophenone to PhSiH(OCH(Me)Ph))$_2$ was observed after 4 minutes at ambient temperature. Similarly, using this catalyst, 80% conversion of cyclohexanone to PhSiH(OCy)$_2$ was observed after 4 minutes at ambient temperature. In the presence of an equimolar amount of PhSiH$_3$ and 1 mol % of [kappa5-N,N,N,P,P-$^{Ph}_2{}^{PPr}$PDIFeH][BF$_4$], 75% percent conversion of cyclohexanone to a mixture of silane products was observed after 24 hours at ambient temperature. In the presence of an equimolar amount of PhSiH$_3$ and 5 mol % of kappa4-N,N,N,N-$^{PyEt}$PDIHCo, 23% percent conversion of cyclohexanone to a mixture of silane products was observed after 15 hours at ambient temperature.

The efficient hydrosilylation of ethyl acetate using such metal complexes has also been observed. In the presence of an equimolar amount of PhSiH$_3$ and 1 mol % of kappa5-N,N,N,P,P-$^{Ph}_2{}^{PPr}$PDIMnH, 99% conversion of ethyl acetate to PhSi(OCH$_2$CH$_3$)$_3$ was observed after 7 hours at ambient temperature.

The hydrosilylation of 1-hexene using such metal complexes has also been observed. In the presence of an equimolar amount of PhSiH$_3$ and 5 mol % of kappa4-N,N,N,N-$^{PyEt}$PDIHCo, 20% conversion of 1-hexene to PhSiH$_2$(Hexyl) was observed after 7 days at ambient temperature.

The hydrosilylation of acetylenes using such metal complexes has also been observed. In the presence of an equimolar amount of PhSiH$_3$ and 5 mol % of kappa4-N,N,P,P-$^{Ph}_2{}^{PPr}$DICoH, 99% conversion of phenylacetylene to olefin containing products was observed after 3 hours at ambient temperature. In the presence of an equimolar amount of PhSiH$_3$ and 1 mol % of kappa4-N,N,P,P-$^{Ph}_2{}^{PPr}$DICoH, 60% conversion of cyclohexylacetylene to olefin containing products was observed after 72 hours at ambient temperature. In the presence of an equimolar amount of PhSiH$_3$ and 1 mol % of kappa4-N,N,P,P-$^{Ph}_2{}^{PPr}$DICoH, 99% conversion of 4-fluorophenylacetylene to olefin containing products was observed after 6 hours at ambient temperature. In the presence of an equimolar amount of PhSiH$_3$ and 1 mol % of kappa4-N,N,P,P-$^{Ph}_2{}^{PPr}$DICoH, 99% conversion of 1-hexyne to trans-(PhSiH$_2$)HC=CH(hexyl) was observed after 1 hour at ambient temperature. In the presence of an equimolar amount of PhSiH$_3$ and 5 mol % of kappa4-N,N,N,N-$^{PyEt}$P-DIHCo, 99% percent conversion of phenylacetylene to a mixture of olefin containing products was observed after 40 minutes at ambient temperature. In the presence of an equimolar amount of PhSiH$_3$ and 5 mol % of kappa4-N,N,N,N-$^{PyEt}$PDIHCo, 60% percent conversion of trimethylsilylacetylene to a mixture of olefin containing products was observed after 40 minutes at ambient temperature.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Unless otherwise indicated, all synthetic reactions were performed in an MBraun glovebox under an atmosphere of purified nitrogen. Aldrich or Acros anhydrous solvents were purged with nitrogen and stored in the glovebox over activated 4 Å molecular sieves and sodium before use. Benzene-d$_6$, acetone-d$_6$, and dimethylsulfoxide-d$_6$ were purchased from Cambridge Isotope Laboratories and dried over 4 Å molecular sieves prior to use. [(COD)RhCl]$_2$ was purchased from Acros and used as received, while AgBF$_4$, 2-(diphenylphosphino)-1-ethylamine and 3-(diphenylphosphino)-1-propylamine were used as received from Strem. 2,6-Diacetylpyridine, p-toluenesulfonic acid, N,N-diisopropyl-1,2-ethanediamine, and N,N-dimethyl-1,3-propanediamine were purchased from TCI America and used as received. All of the gases used in this study were obtained from Praxair.

Solution $^1$H nuclear magnetic resonance (NMR) spectra were recorded at room temperature on either a Varian 400-MR or Bruker Advance III 400 MHz NMR spectrometer. All $^1$H and $^{13}$C NMR chemical shifts (ppm) are reported relative to SiMe$_4$ using $^1$H (residual) and $^{13}$C chemical shifts of the solvent as secondary standards. $^{31}$P NMR data (ppm) is reported relative to H$_3$PO$_4$. Elemental analyses were performed at either Robertson Microlit Laboratories Inc. (Ledgewood, N.J.) or on a PerkinElmer 2400 Series elemental analyzer at the Goldwater Environmental Laboratory (Arizona State University). All UV-Vis spectra were collected on a PerkinElmer Lambda 18 Spectrometer with a two-beam liquid cell. The spectrometer utilized both deuterium and halogen lamps with a change-over occurring at 300 nm.

Single crystals suitable for X-ray diffraction were coated with polyisobutylene oil in a drybox and transferred to a glass fiber or mitogen mount with either Apiezon N grease or paratone oil. They were then mounted on the goniometer head of a Bruker APEX (Arizona State University) or APEX II diffractometer (University of Arizona) equipped with Mo Kα radiation. Either a full sphere (1-Cl, 2-Cl, and [2][BF$_4$]) or hemisphere ([4][(COD)RhCl$_2$]) routine was used for data collection and determination of the lattice constants. The space group was identified and the data were processed using the Bruker SAINT+ program and corrected for absorption using SADABS.

The structures were solved using direct methods (SHELXS), completed by subsequent Fourier synthesis, and refined by full-matrix, least-squares procedures on 192 (SHELXL). The solid state structure of 2-Cl was found to contain two complexes in the asymmetric unit that have stacked PDI chelates approximately 3.6 Å apart; however, they are significantly offset and rotated from one another. The molecular structure of [4][(COD)RhCl$_2$] was found to have disorder at two COD methylene positions that could not be further refined. The crystallographic parameters for 1-Cl, 2-Cl, [2][BF$_4$], and [4][(COD)RhCl$_2$] are provided in Table 5.

the residual p-toluenesulfonic acid and the solvent was removed in vacuo to yield 1.884 g (74%) of a yellowish-orange oil identified as $^{iPr_2NEt}$PDI.

Analysis for C$_{25}$H$_{45}$N$_5$: Calc. C, 72.24; H, 10.91; N, 16.85. Found: C, 72.24; H, 10.98; N, 16.58. $^1$H NMR (benzene-d$_6$): δ 8.41 (d, 7.8 Hz, 2H, m-pyr), 7.30 (t, 7.8 Hz, 1H, p-pyr), 3.63 (t, 7.1 Hz, 4H, NCH$_2$), 2.99 (m, 8H, NCH$_2$ and NCH(CH$_3$)$_2$), 2.37 (s, 6H, N=CCH$_3$), 1.03 (d, 6.7 Hz, 24H, NCH(CH$_3$)$_2$). $^{13}$C{$^1$H} NMR (benzene-d$_6$): δ 165.42 (N=C), 156.25 (o-pyr), 135.88 (p-pyr), 120.85 (m-pyr), 55.18 (NCH$_2$), 48.84 (NCH$_2$), 46.15 (NCH(CH$_3$)$_2$), 20.82 (NCH(CH$_3$)$_2$), 13.16 (N=CCH$_3$).

Preparation of 2,6-((CH$_3$)$_2$NCH$_2$CH$_2$CH$_2$N=C(CH$_3$))$_2$C$_5$H$_3$N ($^{Me_2NPr}$PDI): A 250-mL round-bottomed flask was charged with 0.500 g (3.07 mmol) 2,6-diacetylpyridine, 0.642 g (6.28 mmol) N,N-dimethyl-1,3-propanediamine, 0.006 g (0.034 mmol) p-toluenesulfonic acid and approximately 100 mL toluene. The solution was initially pale yellow in color and the reaction was set to reflux for 34 hours with a Dean-Stark trap. Over this time, the color deepened to a yellowish-orange. The reaction was cooled to room temperature, at which time 50 mL of pentane was added and the flask was placed at 12° C. for 25 hr. The solution was then filtered through Celite and the solvent was removed in vacuo to yield 0.452 g (44%) of a brown oil identified as $^{Me_2iPr}$PDI.

TABLE 5

Crystallographic Data for 1-Cl, 2-Cl, [2][BF$_4$], and [4][(COD)RhCl$_2$]•THF.

|  | 1-Cl | 2-Cl | [2][BF$_4$] | [4][(COD)RhCl$_2$]•THF |
|---|---|---|---|---|
| chemical formula | C$_{25}$K$_{45}$N$_5$ClRh | C$_{19}$H$_{33}$N$_5$ClRh | C$_{19}$H$_{33}$N$_5$BF$_4$Rh | C$_{51}$H$_{61}$N$_3$Cl$_2$OP$_2$Rh |
| formula weight | 554.02 | 469.86 | 521.21 | 1070.69 |
| crystal dimensions | 0.25 × 0.12 × 0.02 | 0.20 × 0.20 × 0.15 | 0.16 × 0.09 × 0.06 | 0.38 × 0.36 × 0.09 |
| crystal system | triclinic | orthorhombic | triclinic | triclinic |
| space group | P 1$^-$ | P 2$_1$2$_1$2$_1$ | P 1$^-$ | P 1$^-$ |
| a (Å) | 9.9107(19) | 9.4308(12) | 9.4394(4) | 12.2988(4) |
| b (Å) | 10.610(2) | 19.024(2) | 10.2794(5) | 12.8848(4) |
| c (Å) | 13.768(3) | 24.424(3) | 13.3439(7) | 16.5002(6) |
| α (deg) | 71.772(3) | 90 | 111.211(3) | 101.120(2) |
| β (deg) | 78.123(3) | 90 | 90.836(3) | 107.100(2) |
| γ (deg) | 82.101(3) | 90 | 112.967(3) | 103.344(2) |
| V (Å$^3$) | 1341.5(4) | 4381.9(10) | 1092.92(9) | 2334.16(13) |
| Z | 2 | 8 | 2 | 2 |
| T (° C.) | 123(2) | 123(2) | 100(2) | 100(2) |
| ρ$_{calcd}$ (g cm$^{-3}$) | 1.372 | 1.424 | 1.584 | 1.523 |
| μ (mm$^{-1}$) | 0.758 | 0.914 | 0.831 | 0.932 |
| reflections collected | 11582 | 35481 | 20419 | 35275 |
| data/restraints/parameters | 5235/0/299 | 7760/0/482 | 4038/0/277 | 8570/0/552 |
| R$_1$ [I > 2σ(I)] | 0.0386 | 0.0306 | 0.0286 | 0.0340 |
| wR$_2$ (all data) | 0.0986 | 0.0629 | 0.0615 | 0.0931 |
| Goodness-of-fit | 1.016 | 1.036 | 1.036 | 1.070 |
| Largest peak, hole (eÅ$^{-3}$) | 0.960, −0.617 | 0.422, −0.308 | 0.504, −0.083 | 0.992, −0.493 |

Preparation of 2,6-(((CH$_3$)$_2$CH)$_2$NCH$_2$CH$_2$N=C(CH$_3$))$_2$C$_5$H$_3$N ($^{iPr_2NEt}$PDI): A 250 mL round-bottomed flask was charged with 1.001 g (6.134 mmol) 2,6-diacetylpyridine, 1.764 g (12.23 mmol) N,N-diisopropyl-1,2-ethanediamine, 0.010 g (0.058 mmol) p-toluenesulfonic acid and approximately 100 mL of toluene. The initial pale yellow solution was fitted with a Dean-Stark trap and reflux condenser and was set to reflux for 18 hours. Over this time, the solution became deep yellow in color and a small amount of water was observed in the trap. Upon cooling to ambient temperature, the toluene was removed in vacuo to yield a yellowish-orange oil. Approximately 50 mL of pentane was then added and the resulting solution was placed at 12° C. for 24 hr. The solution was filtered through Celite to remove Analysis for C$_{19}$H$_{33}$N$_5$: Calcd C, 68.84; H, 10.03; N, 21.13. Found: C, 68.89; H, 9.85; N, 21.10. $^1$H NMR (benzene-d$_6$): δ 8.37 (d, 7.8 Hz, 2H, m-pyr), 7.27 (t, 7.8 Hz, 1H, p-pyr), 3.50 (t, 7 Hz, 4H, NCH$_2$), 2.41 (t, 7 Hz, 4H, NCH$_2$), 2.32 (s, 6H, N=CCH$_3$), 2.16 (s, 12H, N(CH$_3$)$_2$), 2.00 (pseudo quint, 7 Hz, 6H, CH$_2$CH$_2$). $^{13}$C{$^1$H} NMR (benzene-d$_6$): δ 165.92 (N=C), 156.59 (o-pyr), 136.32 (p-pyr), 121.32 (m-pyr), 58.06 (NCH$_2$), 50.55 (NCH$_2$), 45.74 (CH$_2$CH$_2$), 29.69 (N(CH$_3$)$_2$), 13.41 (N=CCH$_3$).

Preparation of ($^{iPr_2NEt}$PDI)RhCl (1-Cl): Under N$_2$ atmosphere, a 20 mL scintillation vial was charged with 0.050 g (0.101 mmol) [(COD)RhCl]$_2$, 0.101 g (0.243 mmol) $^{iPr_2NEt}$PDI, and approximately 10 mL toluene. The solution immediately adopted a green color and became dark-green after approximately 15 minutes. The solution was set to stir for 36 hours at which time the toluene was removed under vacuum. The resulting product was washed with 1-2 mL of pentane several times to remove any excess free ligand and dried in vacuo to yield 0.197 g (98%) of a dark-green microcrystalline solid identified as 1-Cl. Further purification of the complex was achieved following recrystallization from a toluene/pentane solution.

Analysis for $C_{25}H_{45}N_5ClRh$: Calcd C, 54.20; H, 8.19; N, 12.64. Found: C, 54.42; H, 8.33; N, 12.25. $^1H$ NMR (benzene-$d_6$): δ 7.75 (t, 8 Hz, 1H, p-pyr), 6.69 (d, 8 Hz, 2H, m-pyr), 4.38 (t, 6 Hz, 4H, $NCH_2$), 3.38 (t, 6 Hz, 4H, $NCH_2$), 2.96 (sept, 6.7 Hz, 4H, $NCH(CH_3)_2$), 1.45 (s, 6H, N=$CCH_3$), 0.94 (d, 6.7 Hz, 24H, $NCH(CH_3)_2$). $^{13}C\{^1H\}$ NMR (benzene-$d_6$): δ 165.15 (N=C), 157.02 (o-pyr), 123.38 (m-pyr), 122.38 (p-pyr), 57.93 ($NCH_2$), 49.28 ($NCH(CH_3)_2$), 46.68 ($NCH_2$), 21.60 ($NCH(CH_3)_2$), 15.68 (N=$CCH_3$). UV-vis (toluene): $\lambda_{max}$ (nm)=302 (ε=7200 $M^{-1}$ $cm^{-1}$), 452 (ε=4800 $M^{-1}$ $cm^{-1}$), 581 (ε=1400 $M^{-1}$ $cm^{-1}$), 647 (ε=1000 $M^{-1}$ $cm^{-1}$), 764 (ε=580 $M^{-1}$ $cm^{-1}$).

Figure 11:
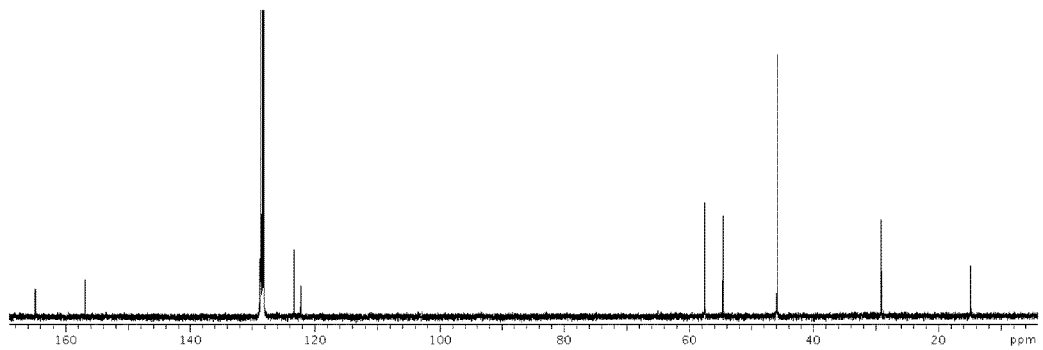
FIG. 11 illustrates the $^{13}$C NMR spectrum of 2-Cl in benzene-$d_6$, in accordance with various aspects of the present disclosure.

Preparation of ($^{Me_2NPr}$PDI)RhCl (2-Cl): Under $N_2$ atmosphere, a 20 mL scintillation vial was charged with 0.052 g (0.105 mmol) [(COD)RhCl]$_2$, 0.075 g (0.225 mmol)$^{Me_2NPr}$PDI, and approximately 10 mL toluene. The solution began turning green instantly, and was dark-green in color after approximately 30 minutes. After stirring for 72 hours, the solvent was removed in vacuo and the resulting solid was washed with a small amount of pentane to remove free ligand. After drying, 0.082 g (84%) of a dark-green microcrystalline solid identified as 2-Cl was obtained. Elemental analysis of 2-Cl was unsatisfactory and the $^{13}C$ spectrum of this complex is provided as FIG. 11 as a measure of purity.

$^1H$ NMR (benzene-$d_6$): δ 7.80 (t, 7.8 Hz, 1H, p-pyr), 6.63 (d, 7.8 Hz, 2H, m-pyr), 4.46 (t, 7 Hz, 4H, $NCH_2$), 2.42 (pseudo quint, 6.5 Hz, 4H, $CH_2CH_2$), 2.31 (t, 6.5 Hz, 4H, $NCH_2$), 2.08 (s, 12H, $NCH_3$), 1.30 (s, 6H, N=$CCH_3$). $^{13}C\{^1H\}$ NMR (benzene-$d_6$): δ 164.82 (N=C), 156.83 (o-pyr), 122.45 (m-pyr), 121.26 (p-pyr), 56.66 ($NCH_2$), 53.89 ($NCH_2$), 45.10 ($NCH_3$), 28.34 ($NCH_2CH_2$), 13.89 (N=$CCH_3$).

Preparation of [($^{iPr_2NEt}$PDI)Rh][BF$_4$] ([1][BF$_4$]): Under $N_2$ atmosphere, a 20 mL scintillation vial was charged with 0.050 g (0.102 mmol) [(COD)RhCl]$_2$, and 0.045 g (0.230 mmol) of AgBF$_4$ suspended in 5 mL of THF. The suspension was stirred in the dark for 1 hour, resulting in the precipitation of a light beige solid (AgCl), which was removed by filtration leaving a pale yellow solution. A 3 mL THF solution of 0.099 g (0.238 mmol) $^{iPr_2NEt}$PDI was then added without delay. The solution instantly darkened in color. The reaction was allowed to stir for 48 hours, at which point the solvent was removed in vacuo. The product was washed with 5 mL of pentane, yielding 0.111 g (90%) of a dark brown microcrystalline solid identified as [1][BF$_4$] upon drying. Alternatively, this complex was prepared following the stoichiometric addition of AgBF$_4$ to 1-Cl.

Analysis for $C_{25}H_{45}N_5BF_4Rh$: Calcd C, 49.60; H, 7.49; N, 11.57. Found: C, 49.82; H, 7.18; N, 10.88. $^1H$ NMR (acetone-$d_6$, 25° C.): δ 8.32 (t, 8 Hz, 1H, p-pyr), 7.99 (broad m, 1H, m-pyr), 7.57 (broad m, 1H, m-pyr), 4.38 (broad m, 2H, $NCH_2$), 4.10 (broad m, 2H, $NCH_2$), 3.69 (broad m, 2H, $NCH_2$), 3.58 (broad m, 2H, $NCH(CH_3)_2$), 3.15 (broad m, 2H, $NCH(CH_3)_2$), 3.01 (broad m, 2H, $NCH_2$), 2.63 (broad s, 3H, N=$CCH_3$), 1.77 (broad s, 3H, N=$CCH_3$), 1.40 (broad m, 6.7 Hz, 12H, $NCH(CH_3)_2$), 1.02 (broad m, 6.7 Hz, 12H, $NCH(CH_3)_2$). $^1H$ NMR (acetone-$d_6$, −20° C.): δ 8.35 (t, 7.9 Hz, 1H, p-pyr), 8.04 (d, 7.9 Hz, 1H, m-pyr), 7.61 (d, 7.9 Hz, 1H, m-pyr), 4.40 (broad t, 5.9 Hz, 2H, $NCH_2$), 4.09 (broad t, 5.9 Hz, 2H, $NCH_2$), 3.71 (t, 6.6 Hz, 2H, $NCH_2$), 3.57 (sept, 6.5 Hz, 2H, $NCH(CH_3)_2$), 3.15 (sept, 6.5 Hz, 2H, $NCH(CH_3)_2$), 2.98 (t, 5.8 Hz, 2H, $NCH_2$), 2.66 (s, 3H, N=$CCH_3$), 1.79 (s, 3H, N=$CCH_3$), 1.42 (d, 6.5 Hz, 6H, $NCH(CH_3)_2$), 1.39 (d, 6.5 Hz, 6H, $NCH(CH_3)_2$), 1.00 (d, 6.5 Hz, 12H, $NCH(CH_3)_2$). $^{13}C\{^1H\}$ NMR (acetone-$d_6$, −20° C.): δ 173.52 (N=C), 161.82 (N=C), 157.53 (o-pyr), 156.68 (o-pyr), 130.46 (p-pyr), 124.56 (m-pyr), 122.47 (m-pyr), 57.33 ($NCH_2$), 55.97 ($NCH_2$), 52.99 ($NCH_2$), 47.72 ($NCH_2$), 44.72 ($NCH_2$), 23.62 ($NCH(CH_3)_2$), 20.31 ($NCH(CH_3)_2$), 18.80 ($NCH(CH_3)_2$), 15.95 (N=$CCH_3$), 14.87 (N=$CCH_3$).

Figure 12:
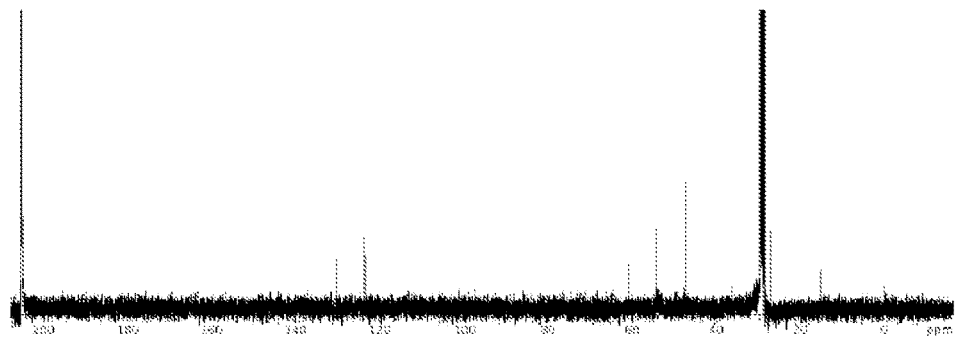
FIG. 12 illustrates the $^{13}$C NMR spectrum of [2][$BF_4$] in acetone-$d_6$ at 25° C., in accordance with various aspects of the present disclosure.

Preparation of [($^{Me_2NPr}$PDI)Rh][BF$_4$] ([2][BF$_4$]): Under $N_2$ atmosphere, a 20 mL scintillation vial was charged with 0.100 g (0.203 mmol) [(COD)RhCl]$_2$, 0.087 g (0.446 mmol) of AgBF$_4$, and 5 mL of THF. The suspension was stirred in the dark for 1 hour, resulting in the precipitation of a light beige solid (AgCl) which was removed by filtration. To the resulting pale yellow solution, a 3 mL THF solution containing 0.135 g (0.407 mmol) of $^{Me_2NPr}$PDI was added. The solution instantly darkened in color. The reaction was stirred for 24 hours, at which point the solvent was removed in vacuo. The product was washed with 5 mL pentane, then dried to yield 0.174 g (82%) of a dark brown microcrystalline solid identified as [2][BF$_4$]. Elemental analysis of [2][BF$_4$] was unsatisfactory and the $^{13}C$ spectrum of this complex is provided as FIG. 12 as a measure of purity.

$^1H$ NMR (acetone-$d_6$, 25° C.): δ 8.35 (t, 8 Hz, 1H, p-pyr), 7.86 (d, 8 Hz, 2H, m-pyr), 4.05 (t, 7 Hz, 4H, $NCH_2$), 2.78 (t, 5.7 Hz, 4H, $NCH_2$), 2.60 (s, 12H, $N(CH_3)_2$), 2.34 (s, 6H, N=$CCH_3$), 2.21 (pseudo quint, 6.3 Hz, 4H, $CH_2CH_2$). $^{13}C\{^1H\}$ NMR (acetone-$d_6$): δ 169.63 (N=C), 130.29 (m-pyr), 123.56 (p-pyr), 60.78 ($NCH_2$), 54.19 ($NCH_2$), 47.42 ($NCH_3$), 23.13 ($NCH_2CH_2$), 15.02 (N=$CCH_3$), one resonance not located.

Preparation of 2,6-(($C_6H_5$)$_2PCH_2CH_2$N=C(CH$_3$))$_2C_5H_3N$ ($^{Ph_2PEt}$PDI): A 250-mL thick-walled glass bomb was charged with 0.407 g (2.49 mmol) of 2,6-diacetylpyridine, 1.120 g (4.89 mmol) of 2-(diphenylphosphino)-1-ethylamine, 0.010 g (0.060 mmol) of p-toluenesulfonic acid, 10 mL toluene, and approximately 10 $cm^3$ of 4 Å molecular sieves. The initial pale yellow solution was set to stir at 80° C. for 24 hours. After cooling to ambient temperature, the bomb was transferred to a glovebox where the resulting solution was filtered through Celite® with excess diethylether. The solvent was then removed in vacuo to yield a yellow oil. The oil was dissolved in approximately 2 mL of diethylether and the resulting solution was placed in the glovebox freezer at −35° C. After 24 h, a light yellow crystalline solid had precipitated. Decanting the mother liquor and subsequent drying allowed the isolation of 1.098 g (72%) of a crystalline yellow solid identified as $^{Ph_2PEt}$PDI.

Analysis for $C_{39}H_{41}N_3P_2$: Calcd C, 75.88; H, 6.73; N, 6.85. Found C, 75.85; H, 6.92; N, 6.74. $^1H$ NMR (CDCl$_3$): δ 7.93 (d, 7.8 Hz, 2H, m-pyr), 7.62 (t, 7.8 Hz, 1H, p-pyr), 7.49 (t, 6 Hz, 8H, o-phenyl), 7.33 (m, 12H, m-phenyl, p-phenyl), 3.68 (pseudo quart, 7.4 Hz, 4H, $CH_2$), 2.56 (t, 8 Hz, 4H, $CH_2$), 2.29 (s, 6H, N=$CCH_3$). $^1H$ NMR (benzene-$d_6$): δ 8.27 (d, 7.8 Hz, 2H, m-pyr), 7.52 (t, 7.6 Hz, 8H, o-phenyl), 7.25 (t, 7.8 Hz, 1H, p-pyr), 7.08 (m, 12H, m-phenyl, p-phenyl), 3.65 (pseudo quart, 7.2 Hz, 4H, $CH_2$), 2.58 (t, 7.6 Hz, 4H, $CH_2$), 2.12 (s, 6H, N=$CCH_3$). $^{13}C$ NMR (benzene-$d_6$): δ 165.72 (N=C), 155.87 (o-pyr), 139.49 (d, $J_{CP}$=14.2 Hz, phenyl), 135.85 (p-pyr), 132.85 (d, $J_{CP}$=19.5 Hz, phenyl), 128.32 (d, $J_{CP}$=6.7 Hz, phenyl), 128.23 (phenyl), 121.19 (m-pyr), 49.48 (d, $J_{CP}$=20.2 Hz, $CH_2$), 30.35 (d, $J_{CP}$=12.7 Hz, CH$_2$), 22.31 (N═C), 12.93 (CH$_2$CH$_2$). $^{31}$P NMR (CDCl$_3$): δ −16.50 (PPh$_2$). $^{31}$P NMR (benzene-d$_6$): δ −16.52 (PPh$_2$).

Preparation of 2,6-((C$_6$H$_5$)$_2$PCH$_2$CH$_2$CH$_2$N═C(CH$_3$))$_2$C$_5$H$_3$N ($^{Ph}{}_2{}^{Pr}$PDI): A 250-mL thick-walled glass bomb was charged with 0.400 g (2.451 mmol) of 2,6-diacetylpyridine, 1.195 g (4.912 mmol) of 3-(diphenylphosphino)-1-propylamine, 0.010 g (0.060 mmol) of p-toluenesulfonic acid, 10 mL of toluene, and approximately 10 cm$^3$ of 4 Å molecular sieves. The initial solution was pale yellow in color and was set to stir at 80° C. for 24 hr. After cooling to ambient temperature, the bomb was transferred to a glovebox where the resulting solution was filtered through Celite® with excess diethylether. The solvent was removed in vacuo, resulting in the isolation of a yellow oil. The oil was dissolved in 2 mL diethylether and placed in a −35° C. freezer. Light yellow crystals were collected after decanting the mother liquor. After drying, 0.918 g (61%) of crystalline yellow $^{Ph}{}_2{}^{PPr}$PDI was obtained.

Analysis for C$_{37}$H$_{37}$N$_3$P$_2$: Calcd C, 75.88; H, 6.37; N, 7.18. Found C, 75.80; H, 6.11; N, 7.22. $^1$H NMR (CDCl$_3$): δ 8.08 (d, 7.8 Hz, 2H, m-pyr), 7.71 (t, 7.8 Hz, 1H, p-pyr), 7.46 (m, 8H, o-phenyl), 7.32 (m, 12H, m-phenyl, p-phenyl), 3.61 (pseudo quart, 7 Hz, 4H, CH$_2$), 2.37 (s, 6H, N═CCH$_3$), 2.23 (m, 4H, CH$_2$), 1.93 (pseudo quint, 7 Hz, 4H, CH$_2$CH$_2$). $^1$H NMR (benzene-d$_6$): δ 8.32 (d, 8 Hz, 2H, m-pyr), 7.53 (t, 6.8 Hz, 8H, o-phenyl), 7.24 (t, 8 Hz, 1H, p-pyr), 7.09 (m, 12H, m-phenyl, p-phenyl), 3.38 (pseudo quart, 6.7 Hz, 4H, CH$_2$), 2.26 (m, 10H, CH$_2$, N═CCH$_3$), 2.04 (pseudo quint, 6.8 Hz, 4H, CH$_2$CH$_2$). $^{13}$C NMR (CDCl$_3$): δ 167.08 (N═C), 156.23 (o-pyr), 139.04 (d, $J_{CP}$=12.7 Hz, phenyl), 136.64 (p-pyr), 132.92 (d, $J_{CP}$=18.7 Hz, phenyl), 128.69 (phenyl), 128.55 (phenyl), 121.14 (m-pyr), 53.35 (d, $J_{CP}$=13.5 Hz, CH$_2$), 27.51 (d, $J_{CP}$=15.7 Hz, CH$_2$CH$_2$CH$_2$) 26.17 (d, $J_{CP}$=11.2 Hz, CH$_2$), 14.01 (N═CCH$_3$). $^{31}$P NMR (CDCl$_3$): δ −18.50 (PPh$_2$). $^{31}$P NMR (benzene-d$_6$): δ −18.70 (PPh$_2$).

Preparation of [($^{Ph}{}_2{}^{PEt}$PDI)Rh][Cl] ([3][Cl]): Under N$_2$ atmosphere, a 20 mL scintillation vial was charged with 0.051 g (0.103 mmol) [(COD)RhCl]$_2$, 0.134 g (0.229 mmol)$^{Ph}{}_2{}^{PEt}$PDI, and approximately 10 mL toluene. The solution turned purple almost instantly and continued to darken in color. The reaction was allowed to stir for 48 hours, at which time the toluene was removed under vacuum. The resulting solid was washed with a small amount of pentane to remove any residual free ligand to yield 0.126 g (84%) of a purple microcrystalline solid identified as [3][Cl].

Anal. for C$_{37}$H$_{37}$N$_3$P$_2$RhCl: Calcd C, 61.38; H, 5.15; N, 5.80. Found: C, 61.55; H, 5.52; N, 5.86. $^1$H NMR (DMSO-d$_6$): δ8.34 (d, 7.6 Hz, 2H, m-pyr), 7.69 (broad m, 1H, p-pyr), 7.45 (t, 6.8 Hz, 2H, phenyl), 7.30 (t, 6.8 Hz, 4H, phenyl), 7.18 (t, 7.2 Hz, 2H, phenyl), 7.06 (pseudo quart, 8H, phenyl), 6.51 (m, 4H, phenyl), 4.49 (broad m, 2H, CH$_2$), 3.89 (broad m, 7.6 Hz, 2H, CH$_2$), 2.82 (broad m, 2H, CH$_2$), 2.65 (t, $J_{PH}$=6.8 Hz, 6H, N═CCH$_3$), 1.76 (broad m, 2H, CH$_2$). $^{13}$C NMR (DMSO-d$_6$): δ 160.24 (N═C), 147.12 (o-pyr), 135.42 (i-phenyl), 132.10 (phenyl), 131.08 (phenyl), 130.52 (phenyl), 130.20 (phenyl), 129.22 (phenyl), 128.74 (phenyl), 125.03 (m-pyr), 51.88 (CH$_2$), 25.54 (CH$_2$), 15.82 (N═CCH$_3$), one resonance not located. $^{31}$P NMR (DMSO-d$_6$): δ 43.64 (d, $J_{RhP}$=135.4 Hz, PPh$_2$).

Preparation of [($^{Ph}{}_2{}^{PPr}$PDI)Rh][Cl] ([4][Cl]): Under N$_2$ atmosphere, a 20 mL scintillation vial was charged with 0.201 g (0.408 mmol) [(COD)RhCl]$_2$, 0.498 g (0.812 mmol)$^{Ph2PPr}$PDI, and approximately 10 mL toluene. The resulting solution turned purple almost instantly and continued to darken while stirring at ambient temperature for 48 hours. The toluene was removed in vacuo and the product was washed with a small amount of pentane to remove any residual free ligand. After drying, 0.475 g (78%) of a purple microcrystalline solid identified [4][Cl] was collected.

Analysis for C$_{39}$H$_{41}$N$_3$P$_2$RhCl: Calcd C, 62.28; H, 5.50; N, 5.59. Found C, 62.87; H, 5.69; N, 5.57. $^1$H NMR (DMSO-d$_6$): δ 8.57 (d, 8.0 Hz, 2H, m-pyr), 7.83 (broad m, 1H, p-pyr), 7.60 (m, 6H, phenyl), 7.15 (m, 6H, phenyl), 6.97 (t, 7.6 Hz, 4H, phenyl), 6.27 (broad t, 8.4 Hz, 4H, phenyl), 4.47 (broad m, 2H, CH$_2$), 3.41 (broad t, 11.5 Hz, 2H, CH$_2$), 2.69 (t, $J_{PH}$=5.7 Hz, 6H, N═CCH$_3$), 2.29 (broad m, 6.3 Hz, 2H, CH$_2$), 1.97 (broad m, 2H, CH$_2$CH$_2$), 1.71 (t, 12 Hz, 2H, CH$_2$), 1.17 (broad m, 2H, CH$_2$CH$_2$). $^{13}$C NMR (DMSO-d$_6$): δ 160.73 (N═C), 145.80 (o-pyr), 135.63 (t, $J_{CP}$=18.0 Hz, i-phenyl), 132.73 (phenyl), 131.25 (phenyl), 130.50 (phenyl), 130.23 (phenyl), 129.38 (phenyl), 128.71 (phenyl), 128.60 (phenyl), 125.52 (m-pyr), 120.05 (p-pyr), 55.51 (CH$_2$), 27.47 (CH$_2$CH$_2$), 23.54 (CH$_2$), 15.44 (N═CCH$_3$). $^{31}$P NMR (DMSO-d$_6$): δ 32.88 (d, $J_{RhP}$=138.5 Hz, PPh$_2$). UV-vis (DMSO): λ$_{max}$ (nm)=317 (ε=12400 M$^{-1}$ cm$^{-1}$), 362 (ε=8000 M$^{-1}$ cm$^{-1}$), 530 (ε=8800 M$^{-1}$ cm$^{-1}$), 671 (ε=2900 M$^{-1}$ cm$^{-1}$).

Preparation of [($^{Ph}{}_2{}^{PPr}$PDI)Rh][(COD)RhCl$_2$] ([4][(COD)RhCl$_2$]): Under N$_2$ atmosphere, a 20 mL scintillation vial was charged with 0.060 g (0.122 mmol) [(COD)RhCl]$_2$, 0.075 g (0.122 mmol)$^{Ph}{}_2{}^{PPr}$PDI, and approximately 10 mL acetone. The resulting solution turned purple upon reagent addition and was stirred at ambient temperature for 24 hours. The acetone was removed in vacuo and the product was washed with 10 mL pentane to remove free COD. After drying, 0.068 g (55%) of a dark purple microcrystalline solid identified ([4][(COD)RhCl$_2$]) was collected.

Analysis for C$_{47}$H$_{53}$N$_3$P$_2$Rh$_2$Cl$_2$: Calcd C, 56.53; H, 5.35; N, 4.21. Found: C, 56.59; H, 5.63; N, 4.26. $^1$H NMR (DMSO-d$_6$): δ8.57 (d, 7.6 Hz, 2H, m-pyr), 7.82 (broad m, 1H, p-pyr), 7.60 (m, 7.0 Hz, 6H, phenyl), 7.15 (m, 6H, phenyl), 6.97 (t, 7.8 Hz, 4H, phenyl), 6.27 (broad t, 4H, phenyl), 4.46 (broad m, 2H, CH$_2$), 4.33 (broad m, 4H, COD), 3.41 (t, 11.2 Hz, 2H, CH$_2$), 2.69 (t, $J_{PH}$=6.0 Hz, 6H, N═CCH$_3$), 2.37 (broad m, 6H, COD), 2.29 (broad m, 2H, CH$_2$), 2.08 (broad m, 2H, CH$_2$CH$_2$), 1.70 (m, 2H, CH$_2$), 1.16 (broad m, 2H, CH$_2$CH$_2$). $^{13}$C NMR (DMSO-d$_6$): δ 160.71 (N═C), 145.77 (o-pyr), 135.71 (i-phenyl), 132.73 (phenyl), 131.25 (phenyl), 130.51 (phenyl), 130.23 (phenyl), 129.39 (phenyl), 128.66 (phenyl), 125.53 (m-pyr), 120.05 (p-pyr), 84.99 (COD), 55.50 (CH$_2$), 30.75 (COD), 27.46 (CH$_2$CH$_2$), 23.54 (CH$_2$), 15.45 (N═CCH$_3$), one resonance not located. $^{31}$P NMR (DMSO-d$_6$): δ 31.63 (d, $J_{RhP}$=138.5 Hz, PPh$_2$).

Preparation of [($^{Ph}{}_2{}^{PEt}$PDI)Rh][BF$_4$] ([3][BF$_4$]): Under N$_2$ atmosphere, a 20 mL scintillation vial was charged with 0.023 g (0.046 mmol) [(COD)RhCl]$_2$, and 0.020 g (0.105 mmol) of AgBF$_4$ suspended in 4 mL of THF. The suspension was stirred in the dark for 1 hour, resulting in the precipitation of a light beige solid (AgCl) which was removed by filtration. To the resulting pale yellow solution, a 3 mL THF solution containing 0.054 g (0.092 mmol) of $^{Ph2PEt}$PDI was added. The solution instantly darkened in color. The reaction was stirred for 24 hours, at which point the solvent was removed in vacuo. The product was washed with 5 mL pentane then dried to yield 0.048 g (68%) of a blue/purple microcrystalline solid identified as [3][BF$_4$].

Analysis for C$_{37}$H$_{37}$N$_3$P$_2$BF$_4$Rh: Calcd C, 57.31; H, 4.81; N, 5.42. Found: C, 57.54; H, 5.20; N, 5.27. $^1$H NMR (DMSO-d$_6$): δ8.54 (d, 7.8 Hz, 2H, m-pyr), 7.90 (pseudo sept, 4.0 Hz, 1H, p-pyr), 7.66 (t, 6.3 Hz, 2H, phenyl), 7.51 (t, 7.0 Hz, 4H, phenyl), 7.39 (t, 7.2 Hz, 2H, phenyl), 7.26

(pseudo quart, 8H, phenyl), 6.72 (pseudo quart, 3.7 Hz, 4H, phenyl), 4.70 (broad m, 2H, CH$_2$), 4.10 (broad m, 2H, CH$_2$), 3.43 (broad m, 2H, CH$_2$), 3.01 (broad m, 2H, CH$_2$), 2.85 (t, JPH=7.2 Hz, 6H, N=CCH$_3$). $^1$H{$^{31}$P} NMR (DMSO-d$_6$): δ8.54 (d, 8.0 Hz, 2H, m-pyr), 7.90 (t, 8.0 Hz, 1H, p-pyr), 7.66 (t, 7.5 Hz, 2H, phenyl), 7.51 (t, 7.5 Hz, 4H, phenyl), 7.38 (t, 7.5 Hz, 2H, phenyl), 7.27 (m, 8H, phenyl), 6.72 (d, 7.5 Hz, 4H, phenyl), 4.70 (broad m, 2H, CH$_2$), 4.10 (broad m, 2H, CH$_2$), 3.43 (broad m, 2H, CH$_2$), 3.01 (broad m, 2H, CH$_2$), 2.85 (s, 6H, N=CCH$_3$). $^{13}$C NMR (DMSO-d$_6$): δ 160.24 (N=C), 147.13 (o-pyr), 135.42 (t, J$_{CP}$=17.2 Hz, i-phenyl), 132.11 (phenyl), 131.09 (phenyl), 130.52 (phenyl), 130.22 (phenyl), 129.27 (phenyl), 128.76 (phenyl), 125.08 (m-pyr), 125.15 (p-pyr), 51.87 (CH$_2$), 35.51 (t, J$_{CP}$=16.4 Hz, CH$_2$), 15.82 (N=CCH$_3$). $^{31}$P NMR (DMSO-d$_6$): δ 42.42 (d, J$_{RhP}$=135.4 Hz, PPh$_2$).

Preparation of [($^{Ph}$$_2$$^{PPrPDI}$)Rh][BF$_4$] ([4][BF$_4$]): Under N$_2$ atmosphere, a 20 mL scintillation vial was charged with 0.040 g (0.081 mmol) [(COD)RhCl]$_2$, and 0.035 g (0.178 mmol) of AgBF$_4$ suspended in 5 mL of THF. The suspension was stirred in the dark for 1 hour, resulting in the precipitation of a light beige solid (AgCl) which was removed by filtration. To the resulting pale yellow solution, a 3 mL THF solution containing 0.100 g (0.162 mmol) of $^{Ph}$$_2$$^{PPr}$PDI was added. The solution instantly darkened in color. The reaction was stirred for 24 hours, at which point the solvent was removed in vacuo. The product was washed with 5 mL pentane then dried to yield 0.103 g (79%) of a purple microcrystalline solid identified as [4][BF$_4$].

Analysis for C$_{39}$H$_{41}$N$_3$P$_2$BF$_4$Rh: Calcd C, 58.30; H, 5.14; N, 5.23. Found: C, 58.04; H, 5.25; N, 5.07. $^1$H NMR (DMSO-d$_6$): δ8.57 (d, 7.6 Hz, 2H, m-pyr), 7.83 (broad m, 1H, p-pyr), 7.60 (pseudo quart, 7.0 Hz, 6H, phenyl), 7.15 (broad m, 6H, phenyl), 6.97 (t, 7.2 Hz, 4H, phenyl), 6.28 (broad t, 4H, phenyl), 4.47 (pseudo d, 10 Hz, 2H, CH$_2$), 3.42 (t, 10.8 Hz, 2H, CH$_2$), 2.69 (t, J$_{PH}$=5.5 Hz, 6H, N=CCH$_3$), 2.29 (broad m, 2H, CH$_2$), 1.99 (broad m, 2H, CH$_2$CH$_2$), 1.71 (m, 2H, CH$_2$), 1.17 (broad m, 2H, CH$_2$CH$_2$). $^{13}$C NMR (DMSO-d$_6$): δ 160.73 (N=C), 145.79 (o-pyr), 135.71 (t, J$_{CP}$=18.0 Hz, i-phenyl), 132.73 (t, J$_{CP}$=6.0 Hz, phenyl), 131.25 (phenyl), 130.51 (phenyl), 130.23 (phenyl), 129.39 (phenyl), 128.66 (t, J$_{CP}$=4.5 Hz, phenyl), 125.53 (m-pyr), 120.05 (p-pyr), 55.51 (CH$_2$), 27.48 (CH$_2$CH$_2$), 23.55 (t, J$_{CP}$=11.2 Hz, CH$_2$), 15.43 (N=CCH$_3$). $^{31}$P NMR (DMSO-d$_6$): δ 31.64 (d, J$_{RhP}$=138.1 Hz, PPh$_2$). UV-vis (DMSO): λ$_{max}$(nm)=317 (ε=8900 M$^{-1}$ cm$^{-1}$), 362 (ε=6600 M$^{-1}$ cm$^{-1}$), 530 (ε=6600 M$^{-1}$ cm$^{-1}$), 671 (ε=3400 M$^{-1}$ cm$^{-1}$).

Examples 1-8

Exemplary Preparation Methods for First-Row Metal Complexes

Example 1

Preparation of [N,N'-(2,6-pyridinediyldiethylidyne) bis[3-(diphenylphosphino)-1-propanamine]]MnCl$_2$ [hereafter ($^{Ph}$$_2$$^{PPr}$PDI)MnCl$_2$]

In the glove box, a thick-walled glass bomb was charged with 0.199 g (0.737 mmol) of MnCl$_2$(THF)$_2$, 0.452 g (0.737 mmol) of $^{Ph2Pr}$PDI ligand, and approximately 30 mL of toluene. The bomb was then sealed under N$_2$ and brought out of the glove box and the mixture was heated at 90° C. in an oil bath for 48 hours. The resulting light orange suspension was vacuum filtered to obtain 0.509 g (0.689 mmol, 93%) of ($^{Ph}$$_2$$^{PPr}$PDI)MnCl$_2$ as a light orange solid. $^1$H NMR (CDCl$_3$, 25° C.), δ (ppm): 66.76, 8.03, 7.38.

Example 2

Preparation of [N,N'-(2,6-pyridinediyldiethylidyne) bis[3-(diphenylphosphino)-1-propanamine]]Mn [hereafter (κ$^5$-N,N,N,P,P-$^{Ph}$$_2$$^{PPr}$PDI)Mn]

Under an inert atmosphere, a 20 mL scintillation vial was charged with 4.33 g (21.66 mmol) of mercury, 0.025 g (1.083 mmol) of sodium, and approximately 4 mL of THF. The mixture was stirred at room temperature for 20 minutes. After 0.011 g (0.108 mmol) of cyclooctatetraene was added (as a reduction catalyst), the solution turned yellow in color. A slurry of ($^{Ph}$$_2$$^{PPr}$PDI)MnCl$_2$ (0.160 g, 0.216 mmol) in another 10 mL of THF was then added to the vial. The solution turned deep brown in color and was allowed to stir at room temperature. After 15 hr, the resulting solution was filtered through Celite® and the solvent was evacuated to obtain a brown solid. It was scraped from the filter flask in the presence of n-pentane (2×10 mL) and dried to remove any remaining solvent. The solid was then dissolved in 15 mL toluene and filtered through a Celite® column to get rid of the salt produced during the reaction. After evacuating the toluene, the brown material was crystallized from toluene/ diethyl ether and identified as (κ$^5$-N,N,N,P,P-$^{Ph}$$_2$$^{PPr}$PDI)Mn.

Figure 13:
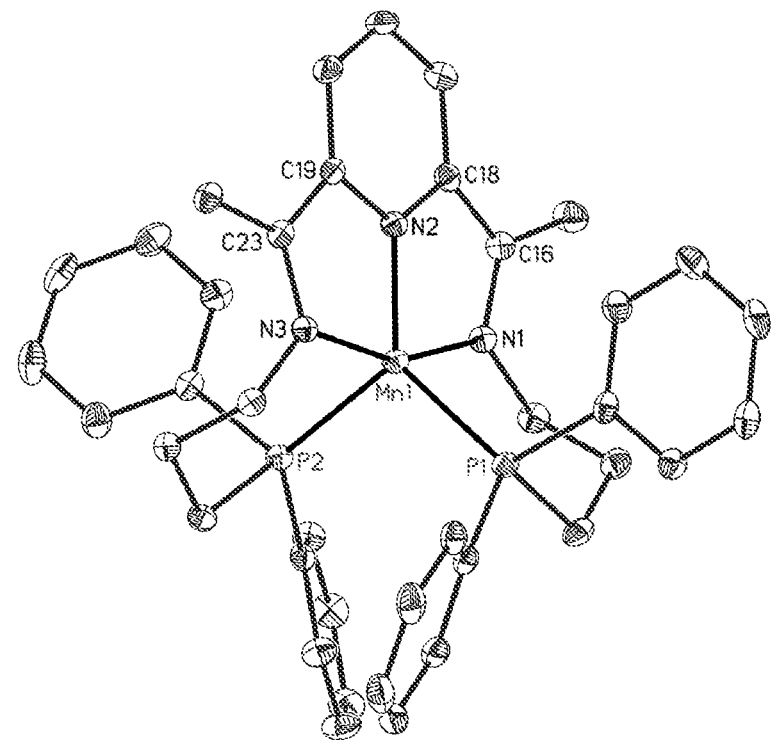
FIG. 13 illustrates the solid state structure of ($\kappa^5$-N,N,N,P,P-$^{Ph}_2{}^{PPr}$PDI)Mn, in accordance with various aspects of the present disclosure.

$^1$H NMR (benzene-d$_6$), δ (ppm)=94.49, 66.59, 26.80, 24.78, 16.98, 8.15, 6.89, 6.68, 4.58, −9.58, −97.39. This product has also been characterized by single crystal X-ray diffraction (see FIG. 13).

(κ$^5$-N,N,N,P,P-$^{Ph2PPr}$PDI)Mn

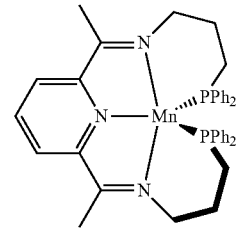

Example 3

Preparation of [N,N'-(2,6-pyridinediyldiethylidyne) bis(2-pyridineethanamine)]FeBr$_2$ [hereafter ($^{PyEt}$PDI)FeBr$_2$]

In a nitrogen filled glove box, a 20 mL reaction vial was charged with 0.105 g of FeBr$_2$ (0.487 mmol) and 5 mL of dried THF. To it, 0.185 g (0.499 mmol) of $^{PyEt}$PDI dissolved in 10 mL of THF was added slowly while stirring. A dark blue solid formed immediately after ligand addition. After stirring for 15 hr, the deep blue solid was collected on the top of a filtering frit. After washing with toluene and ether followed by drying under vacuum for 1 hr, 0.220 g (77%) of a blue solid identified as ($^{PyEt}$PDI)FeBr$_2$ was obtained.

$^1$H NMR (chloroform-d, 25° C.): 132.03, 66.86, 36.86, 31.23, 18.10, 7.99, −12.05.

Example 4

Preparation of [N,N'-(2,6-pyridinediyldiethylidyne)bis(2-pyridineethanamine)]Fe [hereafter (κ$^5$-N,N,N,N,N-$^{PyEt}$PDI)Fe]

In a nitrogen filled glove box, a 20 mL reaction vial was charged with 0.118 g (0.201 mmol) of ($^{PyEt}$PDI)FeBr$_2$ and 10 mL of THF and kept at −35° C. for 30 min. Another vial was charged with 3.92 g of Hg (19.60 mmol) and 2 mL of THF. To it, 0.023 g (1.00 mmol) of freshly cut Na metal was added and the resulting amalgam was allowed to stir for 20 min. To this mixture, the cold slurry of ($^{PyEt}$PDI)FeBr$_2$ in THF was transferred slowly while stirring. A color change from blue to green was observed after one day of stirring. The solution turned bluish-green after 3 days. After 7 days of stirring, the resulting greenish-blue solution was filtered through Celite® and the solvent was removed under vacuum. After washing with pentane and ether, 75 mg (86%) of a deep blue solid identified as (κ$^5$-N,N,N,N,N-$^{PyEt}$PDI)Fe was collected.

Figure 14:
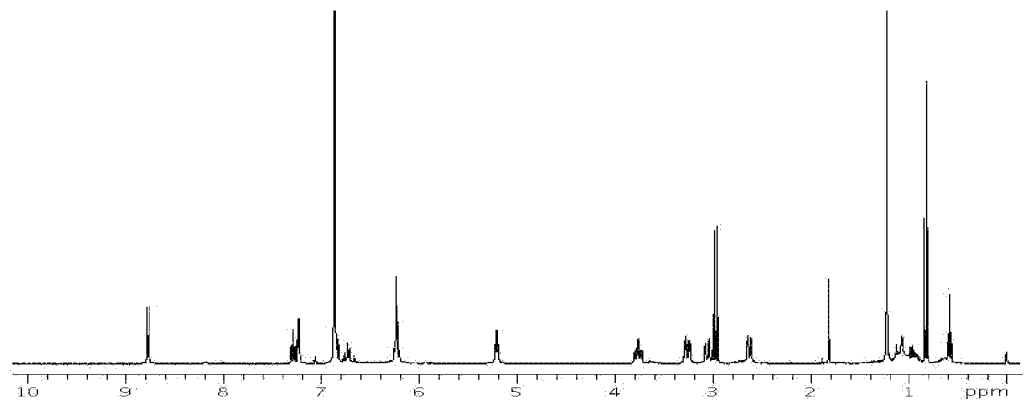
FIG. 14 illustrates the $^1$H NMR spectrum of ($\kappa^5$-N,N,N,N,N-$^{PyEt}$PDI)Fe, in accordance with various aspects of the present disclosure.
Figure 15:
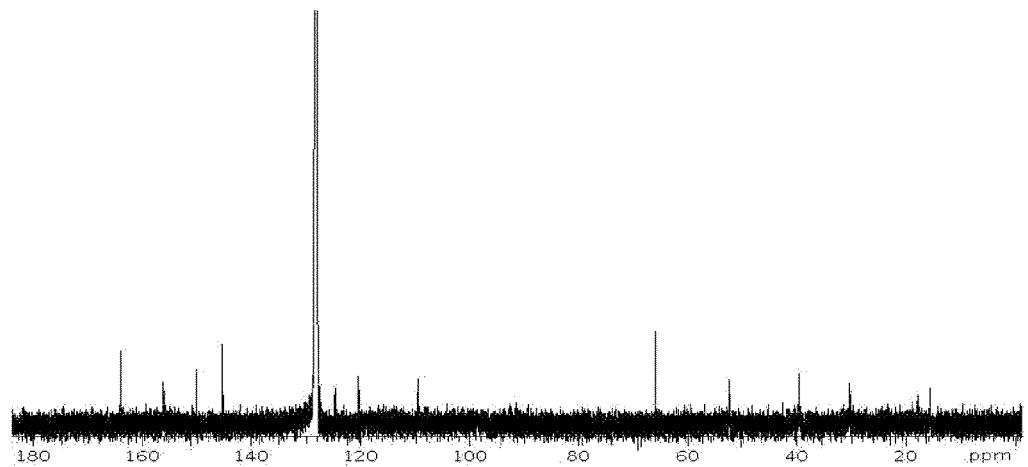
FIG. 15 illustrates the $^{13}$C NMR spectrum of ($\kappa^5$-N,N,N,N,N-$^{PyEt}$PDI)Fe, in accordance with various aspects of the present disclosure.

$^1$H NMR (benzene-d$_6$, 25° C.): δ 9.07 (d, 7.2 Hz, 2H, m-$^c$Py), 7.58 (t, 7.6 Hz, 1H, p-$^c$Py), 7.53 (d, 5.2 Hz, 2H, o-$^a$Py), 6.53 (m, 4H, m-$^a$Py), 5.50 (m, 2H, p-$^a$Py), 4.05 (m, 2H), 3.55 (m, 2H), 3.36 (t, 3.2 Hz, 2H), 2.92 (d, 12.8 Hz, 2H), 1.52 (s, 6H). This spectrum is included as FIG. 14. $^{13}$C NMR (benzene-d$_6$): δ 30.24 (CH$_3$), 39.48 (CH$_2$CH$_2$N), 52.41 (CH$_2$CH$_2$N), 109.47 (m-$^c$Py), 120.35 (m-$^a$Py), 124.62 (m-$^a$Py), 127.18 (p-$^a$Py), 145.13 (p-$^c$Py), 150.07 (o-$^a$Py), 156.11 (o-$^c$Py), 156.25 (o-$^a$Py), 163.97 (C=N). This spectrum is included as FIG. 15.

κ$^5$-N,N,N,N,N-$^{PyEt}$PDIFe:

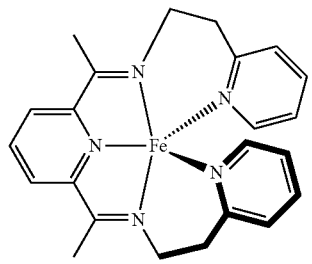

Example 5

Preparation of [N,N'-(2,6-pyridinediyldiethylidyne)bis[3-(diphenylphosphino)-1-propanamine]]CoCl$_2$ [hereafter ($^{Ph_2PPr}$PDI)CoCl$_2$]

Under an inert atmosphere a 20 mL scintillation vial was charged with 0.052 g (0.397 mmol) of CoCl$_2$, 0.238 g (0.387 mmol) of $^{Ph_2PPr}$PDI ligand and approximately 10 mL of THF. The reaction darkened instantly upon addition and was stirred for 24 hours. THF was removed under reduced pressure. The product was washed with 2-3 mL aliquots of pentane until clean. This material was then dried and collected, yielding 0.154 g (0.212 mmol, 53%) of a dark brown microcrystalline solid identified as ($^{Ph_2PPr}$PDI)CoCl$_2$.

Example 6

Preparation of [[N,N'-(2,6-pyridinediyldiethylidyne)bis[3-(diphenylphosphino)-1-propanamine]]Co][Cl] (hereafter [(κ$^5$-N,N,N,P,P-$^{Ph_2PPr}$PDI)Co][Cl])

Under an inert atmosphere, a 20 mL scintillation vial was charged with 0.490 g (0.659 mmol) of ($^{Ph_2PPr}$PDI)CoCl$_2$ and 15 mL toluene. One equivalent of NaEt$_3$BH (0.65 mL, 0.65 mmol) was added as a 1 M solution in toluene via 1 mL syringe and the reaction was stirred for 24 hours. The reaction was filtered through Celite® and dried under reduced pressure. A dark brown microcrystalline solid identified as [(κ$^5$-N,N,N,P,P-$^{Ph_2PPr}$PDI)Co][Cl] was collected (0.177 g, 0.250 mmol, 37%).

$^1$H NMR (acetone-d$_6$, 25° C.), δ (ppm): 8.55 (d, 7 Hz, 2H), 8.15 (t, 7 Hz, 1H), 7.62 (pseudo t, 7 Hz, 4H), 7.56 (pseudo t, 7 Hz, 2H), 7.46 (t, 8 Hz, 4H), 7.20 (m, 4H), 6.98 (t, 7 Hz, 4H), 4.07 (broad d, 13 Hz, 2H), 2.72 (pseudo t, 13 Hz, 2H), 2.56 (m, 4H), 2.43 (m, 8H), 2.1 (quint., 2 Hz, 2H).

[(κ$^5$-N,N,N,P,P-$^{Ph_2PPr}$PDI)Co][Cl]:

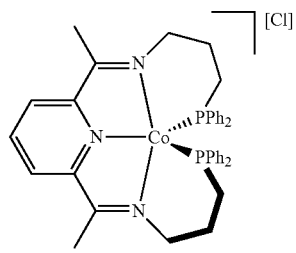

Example 7

Preparation of [N,N'-(1,2-dimethyl-1,2-ethanediylidene)bis[3-(diphenylphosphino)-1-propanamine]]Ni [hereafter (κ$^4$-N,N,P,P-$^{Ph_2PPr}$DI)Ni]. Under a nitrogen atmosphere, a 20 mL scintillation vial was charged with 0.087 g (0.162 mmol) of $^{Ph_2PPr}$DI, 0.041 g (0.148 mmol) of nickel bis(cyclooctadiene), and approximately 7 mL of toluene. The resulting solution instantly turned deep red in color and persisted while stirring at 32° C. for 24 hours. The solution was then filtered through Celite® and the toluene was removed in vacuo to yield 0.043 g (49%) of a red crystalline solid identified as (κ$^4$-N,N,P,P-$^{Ph_2PPr}$DI)Ni.

Figure 16:
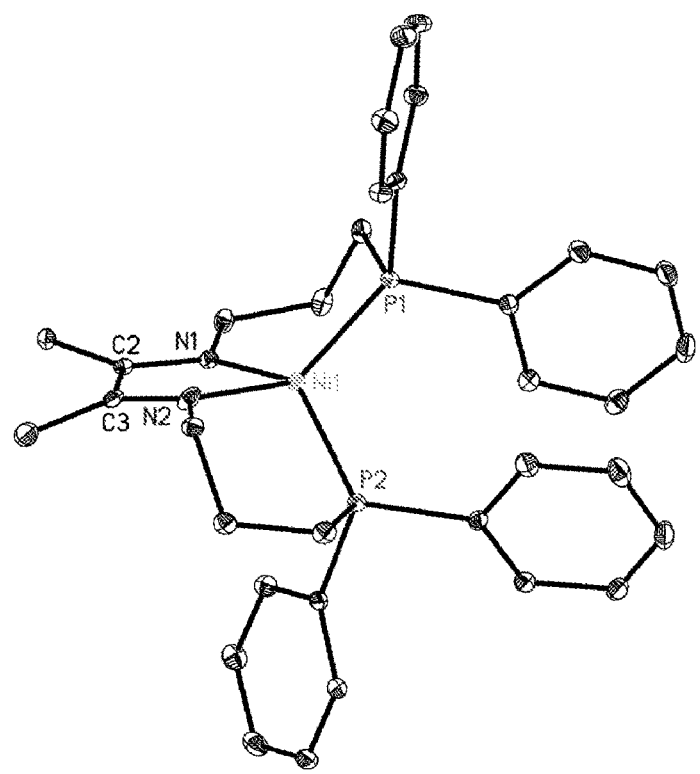
FIG. 16 illustrates the solid state structure of ($\kappa^4$-N,N,P,P-$^{Ph}_2{}^{PPr}$DI)Ni, in accordance with various aspects of the present disclosure.

$^1$H NMR (benzene-d$_6$): δ (ppm) 7.66 (t, 7.8 Hz), 7.03 (m), 6.77 (t, 7.0 Hz), 6.66 (t, 7.0 Hz), 3.52 (m, 2H), 3.05 (m, 2H), 2.90 (m, 2H), 2.37 (m, 2H), 2.01 (m, 2H), 1.49 (m, 2H), 1.44 (t, 7.0 Hz, 6H, N=C(CH$_3$)). {$^{31}$P}$^1$H NMR (benzene-d$_6$): δ (ppm) 7.66 (d, 7.4 Hz, 4H, phenyl), 7.44 (d, 7.0 Hz, 4H, phenyl), 7.06 (m, 4H, phenyl), 6.77 (t, 7.4 Hz, 4H, phenyl), 6.66 (t, 7.0 Hz, 4H, phenyl), 3.52 (dd, 5.5 Hz, 8.6 Hz, 2H), 3.05 (t, 13.3 Hz, 2H), 2.91 (m, 2H), 2.36 (m, 2H), 2.02 (m, 2H) 1.49 (m, 2H) 1.44 (s, 6H, N=C(CH$_3$)). $^{31}$P NMR (benzene-d$_6$): δ (ppm) 39.03 (s, PPh$_2$). This product has also been characterized by single crystal X-ray diffraction (see FIG. 16).

(κ$^4$-N,N,P,P-$^{Ph_2PPr}$DI)Ni

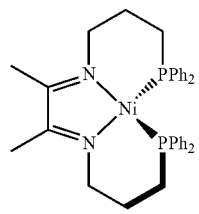

Example 8

Preparation of [N,N'-(2,6-pyridinediyldiethylidyne)bis[3-(diphenylphosphino)-1-propanamine]]Ni [hereafter ($\kappa^4$-N,N,N,P-$^{Ph}_2{}^{PPr}$PDI)Ni]

Figure 17:
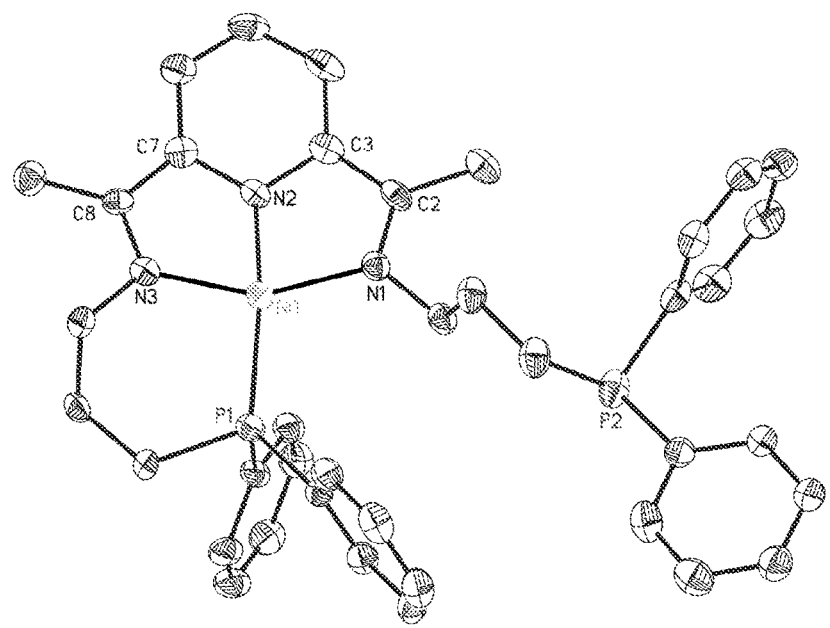
FIG. 17 illustrates the solid state structure of ($\kappa^4$-N,N,N,P-$^{Ph}_2{}^{PPr}$PDI)Ni, in accordance with various aspects of the present disclosure.

Under a nitrogen atmosphere, a 20 mL scintillation vial was charged with 0.045 g (0.075 mmol) of $^{Ph}_2{}^{PPr}$PDI and approximately 5 mL of toluene. A separate scintillation vial was also charged with 0.021 g (0.076 mmol) of nickel bis(cyclooctadiene) and approximately 5 mL of toluene. The $^{Ph}_2{}^{PPr}$PDI solution was then added drop-wise into the vial containing Ni(COD)$_2$, which transitioned from a light yellow to a deep olive green solution instantaneously. The resulting reaction mixture was then allowed to stir at 32° C. for 24 hours. After 24 hours the deep green color had persisted and the toluene was removed in vacuo to yield 0.031 g (61%) of a dark green solid identified as ($\kappa^4$-N,N,N,P-$^{Ph}_2{}^{PPr}$PDI)Ni. The product was then recrystallized from a diethyl ether, pentane mixture at −35° C. and the resulting green crystals were harvested and sealed under a nitrogen atmosphere at −35° C. for future use. $^1$H NMR (benzene-d$_6$, 25° C.): δ (ppm) 23.87, 12.83, 7.60, 7.38, 6.49, 5.13, 1.38, −4.80. This product has also been characterized by single crystal X-ray diffraction (see FIG. 17).

($\kappa^4$-N,N,N,P-$^{Ph}_2{}^{PPr}$PDI)Ni

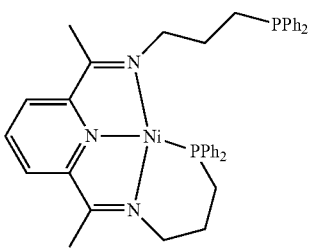

Examples 9-20

Ketone Hydrosilylation Reactions Employing the Disclosed Metal Complexes

Example 9

Hydrosilylation of Acetophenone with Phenylsilane Using 0.1 Mol % of ($\kappa^5$-N,N,N,P,P-$^{Ph}_2{}^{PPr}$PDI)Mn In the glove box, a mixture of 922 μL (7.48 mmol) of PhSiH$_3$ and 874 μL (7.48 mmol) of acetophenone was added to a 20 mL scintillation vial containing 0.005 g (0.00748 mmol) of ($\kappa^5$-N,N,N,P,P-$^{Ph}_2{}^{PPr}$PDI)Mn. The resulting brown solution was allowed to stir for four minutes in the dry box before being exposed to air. The resulting colorless solution was immediately filtered through a Celite® column to remove any residual manganese containing impurities. Formation of the hydrosilylated products PhSiH$_2$(OCH(Me)(Ph)) and PhSiH(OCH(Me)(Ph))$_2$ with greater than 99% conversion (TOF≈15,000 hr$^{-1}$ with respect to acetophenone) was confirmed by $^1$H NMR spectroscopy H NMR (benzene-d$_6$), δ (ppm)=7.82, 7.75, 7.30, 7.24, 5.32, 5.15, 1.39. Unreacted PhSiH$_3$ was also observed at 7.38, 7.09 and 4.24 ppm.

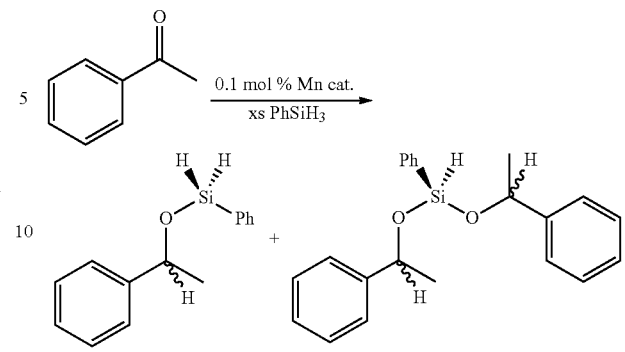

Example 10

Hydrosilylation of Three Acetophenone Equivalents Per Equivalent of Phenylsilane Using 1.0 Mol % of ($\kappa^5$-N,N,N,P,P-$^{Ph}_2{}^{PPr}$PDI)Mn In the glove box, a solution of 33.2 μL (0.269 mmol) of PhSiH$_3$ and 94.4 μL (0.808 mmol) of acetophenone in approximately 1 mL of benzene-d$_6$ was added to a 20 mL scintillation vial containing 0.0018 g (0.00269 mmol) of ($\kappa^5$-N,N,N,P,P-$^{Ph}_2{}^{PPr}$PDI)Mn. The resulting brown solution was transferred into a J. Young NMR tube and a $^1$H NMR spectrum was recorded after 6 hours. Formation of the desired product PhSi(OCH(Me)(Ph))$_3$ with greater than 99% conversion was confirmed (TOF≈50 hr$^{-1}$ with respect to acetophenone).

$^1$H NMR (benzene-d$_6$), δ (ppm)=7.82, 7.75, 7.39, 7.30, 7.24, 7.08, 5.32, 5.15, 2.11, 1.39.

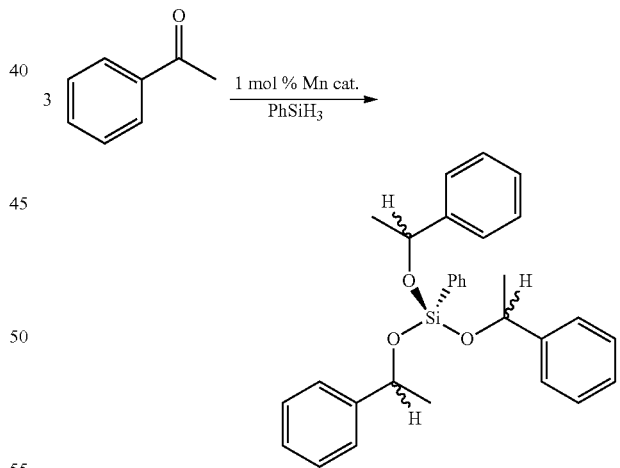

Example 11

Hydrosilylation of Cyclohexanone with Phenylsilane Using 0.1 Mol % of ($\kappa^5$-N,N,N,P,P-$^{Ph}_2{}^{PPr}$PDI)Mn Under an inert atmosphere, a mixture of 440 μL (3.58 mmol) of PhSiH$_3$ and 362 μL (3.58 mmol) of cyclohexanone was added to a 20 mL scintillation vial containing 0.0024 g (0.00358 mmol) of ($\kappa^5$-N,N,N,P,P-$^{Ph}_2{}^{PPr}$PDI)Mn. The resulting brown solution was stirred for four minutes in the dry box before being exposed to air. The resulting colorless solution was filtered through a Celite® column. The $^1$H NMR spectrum of the product mixture was recorded and the hydrosilylated products PhSiH$_2$(O$^c$Hex) and PhSiH (O$^c$Hex)$_2$ were observed with greater than 99% conversion (TOF≈15,000 hr$^{-1}$ with respect to cyclohexanone).

$^1$H NMR (benzene-d$_6$), δ (ppm)=7.87, 7.23, 5.39, 3.99, 1.89, 1.64, 1.56, 1.33, 1.12. The new multiplet at 3.99 ppm and the peaks between 1.89-1.12 ppm confirmed the formation of the desired hydrosilylated product. The singlet at 5.39 ppm is attributed to the new Si—H resonances of the hydrosilylated product while unreacted PhSiH$_3$ was observed at 7.38, 7.09 and 4.24 ppm.

Example 12

Hydrosilylation of Three Cyclohexanone Equivalents Per Equivalent of Phenylsilane Using 1.0 Mol % of (κ$^5$-N,N,N,P,P-$^{Ph}_2$$^{PPr}$PDI)Mn In the glove box, a solution of 35.1 μL (0.284 mmol) of PhSiH$_3$ and 85.9 μL (0.853 mmol) of cyclohexanone in approximately 1 mL of benzene-d$_6$ was added to a 20 mL scintillation vial containing 0.0019 g (0.00284 mmol) of (κ$^5$-N,N,N,P,P-$^{Ph}_2$$^{PPr}$PDI)Mn. The resulting brown solution was transferred into a J. Young NMR tube and a $^1$H NMR spectrum was recorded after 10 minutes. At this point, the desired product PhSi(O$^c$Hex)$_3$ was observed and full conversion (>99%) to this product had occurred after 4 hours (TOF≈75 hr$^{-1}$ with respect to cyclohexanone).

$^1$H NMR (benzene-d$_6$), δ (ppm)=7.94 (d, 2H), 7.25 (m, 3H), 4.13 (m, 1H), 1.88 (m, 2H), 1.64 (m, 2H), 1.54 (m, 2H), 1.33 (m, 2H), 1.12 (m, 2H).

Example 13

Hydrosilylation of 2,4-Dimethyl-3-Pentanone with Phenylsilane Using 1.0 Mol % of (κ$^5$-N,N,N,P,P-$^{Ph}_2$$^{PPr}$PDI)Mn In the glove box, a solution of 44.3 μL (0.358 mmol) of PhSiH$_3$ and 101.7 μL (0.718 mmol) of 2,4-dimethyl-3-pentanone in approximately 1 mL of benzene-d$_6$ was added to a 20 mL scintillation vial containing 0.0024 g (0.00358 mmol) of (κ$^5$-N,N,N,P,P-$^{Ph}_2$$^{PPr}$PDI)Mn. The resulting brown solution was transferred into a J. Young NMR tube and the formation of PhSiH(OCH($^i$Pr)$_2$)$_2$ (>99% conversion) was confirmed by $^1$H NMR spectroscopy after 30 min (TOF≈200 hr$^{-1}$ with respect to ketone).

$^1$H NMR (benzene-d$_6$), δ (ppm)=7.76 (d, 2H, phenyl), 7.20 (m, 3H, phenyl), 5.36 (s, 1H, SiH), 3.37 (t, 2H), 1.76 (m, 4H), 0.94 (m, 24H). The Si—H singlet at 5.36 ppm confirmed the preferential formation of the dihydrosilylated product, PhSiH(OCH($^i$Pr)$_2$)$_2$.

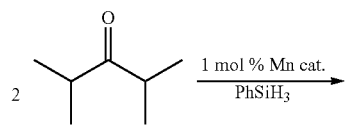

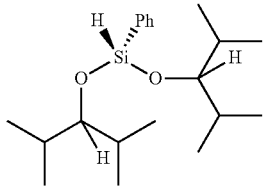

Example 14

Hydrosilylation of 2-Hexanone with Phenylsilane Using 1.0 Mol % of (κ$^5$-N,N,N,P,P-$^{Ph}_2$$^{PPr}$PDI)Mn In the glove box, a solution of 60.9 μL (0.494 mmol) of PhSiH$_3$ and 60.8 μL (0.494 mmol) of 2-hexanone in approximately 1 mL of benzene-d$_6$ was added to a 20 mL scintillation vial containing 0.0033 g (0.00494 mmol) of (κ$^5$-N,N,N,P,P-$^{Ph}_2$$^{PPr}$PDI)Mn. The resulting brown solution was transferred into a J. Young NMR tube. Greater than 99% conversion to the desired organic products, PhSiH$_2$(OCH (Me)($^n$Bu)) and PhSiH(OCH(Me)($^n$Bu))$_2$, was confirmed by $^1$H NMR spectroscopy after 10 min (TOF≈600 hr$^{-1}$ with respect to 2-hexanone).

$^1$H NMR (benzene-d$_6$), δ (ppm)=7.81, 7.22, 5.33, 4.09, 1.60, 1.41, 1.27, 0.88. Unreacted PhSiH$_3$ resonances were also observed.

Example 15

Hydrosilylation of Benzophenone with Phenylsilane Using 10 Mol % of (κ$^5$-N,N,N,P,P-$^{Ph}_2$$^{PPr}$PDI)Mn In the glove box, a solution of 16.7 μL (0.135 mmol) of PhSiH$_3$ and 0.024 g (0.135 mmol) of benzophenone in approximately 1 mL of benzene-d$_6$ was added to a 20 mL scintillation vial containing 0.009 g (0.0135 mmol) of (κ$^5$-N,N,N,P,P-$^{Ph}_2$$^{PPr}$PDI)Mn. The resulting brown solution was transferred into a J. Young NMR tube. Greater than 90% conversion to the desired hydrosilylated products was detected by $^1$H NMR spectroscopy after 24 hours along with excess phenylsilane.

Example 16

Hydrosilylation of Acetophenone with Phenylsilane Using 10 Mol % of (κ$^5$-N,N,N,N,N-$^{PyEt}$PDI)Fe In a nitrogen filled glove box, a 20 mL reaction vial was charged with 0.006 g (0.014 mmol) of (0-N,N,N,N,N-$^{PyEt}$PDI)Fe and 0.5 mL of benzene-d$_6$. Another vial was charged with 17.3 μL (0.140 mmol) of PhSiH$_3$, 16.4 μL (0.140 mmol) of acetophenone, and 0.5 ml of benzene-d$_6$. The latter solution was added to the former and the entire reaction mixture was then transferred into a J. Young NMR tube. A $^1$H NMR spectrum was recorded after 1 hr at which time a mixture of the hydrosilylated products PhSiH$_2$(OCH (Me)(Ph)) and PhSiH(OCH(Me)(Ph))$_2$ (>99% conversion, TOF≈10 hr$^{-1}$) were observed along with unreacted PhSiH$_3$. Addition of an extra 10 equivalents of acetophenone in the same NMR tube resulted in formation of the same hydrosilylated products within 15 minutes (99% conversion, TOF=40 h$^{-1}$) while all unreacted PhSiH$_3$ was consumed.

$^1$H NMR (benzene-d$_6$): δ (ppm)=7.75, 7.30, 7.08, 5.31, 5.01, 1.44, 1.36.

Example 17

Figure 18:
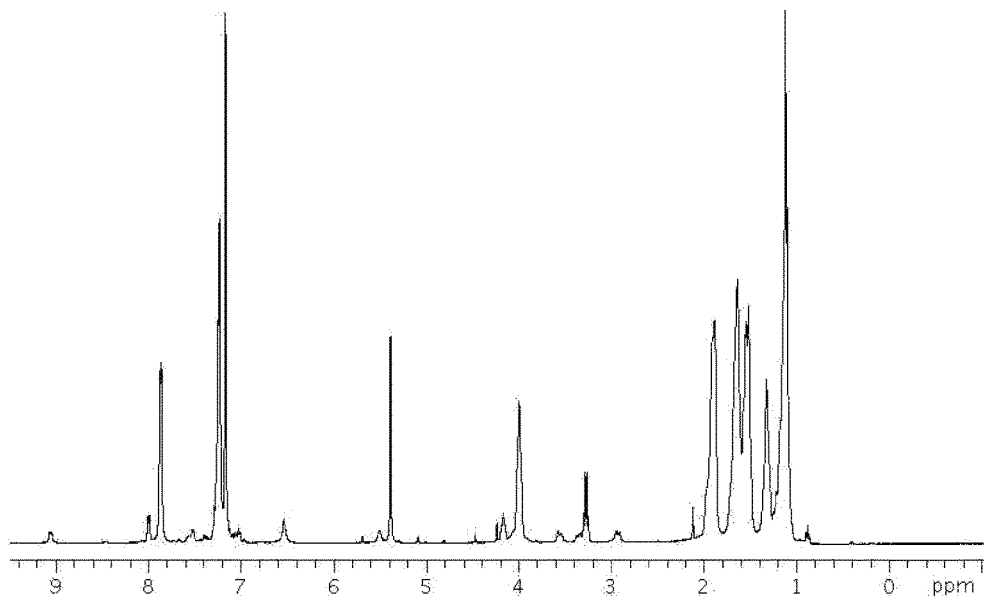
FIG. 18 illustrates the $^1$H NMR spectrum recorded following the hydrosilylation of cyclohexanone with phenylsilane using 10 mol % of $\kappa^5$-N,N,N,N,N-$^{PyEt}$PDIFe.

Hydrosilylation of Cyclohexanone with Phenylsilane Using 10 Mol % of κ⁵-N,N,N,N,N-$^{PyEt}$PDIFe In a nitrogen filled glove box, a 20 mL reaction vial was charged with 0.005 g (0.012 mmol) of κ⁵-N,N,N,N,N-$^{PyEt}$PDIFe and 0.5 mL of benzene-$d_6$. A second vial was charged with 14.5 µL of PhSiH₃ (0.118 mmol), 12.1 µL of cyclohexanone (0.117 mmol), and 0.5 mL of benzene-$d_6$. The latter mixture was added to the former and the resulting solution was transferred to a J. Young NMR tube. After one hour, the solution was analyzed by ¹H NMR spectroscopy and formation of the hydrosilylated product PhSiH₂(O$^c$Hex) was observed (>99% conversion, TOF≈10 hr⁻¹) along with a minimal amount of unreacted PhSiH₃. ¹H NMR (benzene-$d_6$): δ (ppm)=7.83, 7.24, 5.39, 3.99, 1.91, 1.64, 1.53, 1.33, 1.11. This spectrum is provided as FIG. 18.

Example 18

Hydrosilylation of 2,4-Dimethyl-3-Pentanone with Phenylsilane Using 10 Mol % of (κ⁵-N,N,N,N,N-$^{PyEt}$PDI)Fe In a nitrogen filled glove box, a 20 mL reaction vial was charged with 0.005 g (0.012 mmol) of (κ⁵-N,N,N,N,N-$^{PyEt}$PDI)Fe and 0.5 mL of benzene-$d_6$. Another vial was charged with 14.4 µL of PhSiH₃ (0.117 mmol), 16.6 µL of diisopropylketone (0.117 mmol), and 0.5 mL of benzene-$d_6$. The latter solution was added to the former and the reaction was transferred into a J. Young NMR tube. The sealed tube was heated at 80° C. in oil bath for 13 hr, after which time, 45% conversion to the hydrosilylated product was observed by ¹H NMR spectroscopy.

¹H NMR (benzene-$d_6$): δ (ppm)=7.68, 7.08, 5.34, 3.14, 1.73, 0.83.

Example 19

Hydrosilylation of Acetophenone with Phenylsilane Using 10 Mol % of (0-N,N,P,P-$^{Ph_2PPr}$DI)Ni Under a nitrogen atmosphere a 20 mL scintillation vial was charged with 0.002 g (0.019 mmol) of acetophenone, 0.002 g (0.019 mmol) of phenylsilane, and approximately 0.5 mL of benzene-$d_6$. The resulting colorless solution was then added to a separate 20 mL scintillation vial containing 0.001 mg (0.0019 mmol) of (κ⁴-N,N,P,P-$^{Ph2PPr}$DI)Ni. The resulting deep red solution was then transferred to a J. Young NMR tube and sealed under a nitrogen atmosphere. After approximately 17 hr, greater than 99% conversion to the hydrosilylated product was observed.

¹H NMR (benzene-$d_6$) δ (ppm)=7.80 (m), 7.18-7.06 (m), 6.77 (t, 7.0 Hz), 6.66 (t, 7.4 Hz), 5.38 (s), 5.31 (s), 5.01 (m, 13.0 Hz, 6.0 Hz), 1.44 (d, 6.0 Hz), 1.40 (s), 1.37 (d, 6.2 Hz).

Example 20

Hydrosilylation of Acetophenone with Phenylsilane Using 5 Mol % of (κ⁴-N,N,N,P-$^{Ph_2PPr}$PDI)Ni Under a nitrogen atmosphere a 20 mL scintillation vial was charged with 20.1 µL (0.173 mmol) of acetophenone, 21.3 µL (0.173 mmol) of phenylsilane and approximately 0.5 mL of benzene-$d_6$. The resulting colorless solution was then added drop-wise into a separate 20 mL scintillation vial that had been previously charged with 5.8 mg (0.009 mmol) of (κ⁴-N,N,N,P-$^{Ph_2PPr}$PDI)Ni. The resulting olive green solution was then transferred into a J. Young NMR tube and sealed under a nitrogen atmosphere. Product formation (<10%) was initially observed via ¹H NMR spectroscopy after 1 hr and 42 min and 65% conversion was observed after 24 hr. After 120 hr, 89% of the acetophenone had been hydrosilylated.

¹H NMR (400 MHz, benzene-$d_6$) δ (ppm)=7.88 (m), 7.82 (m), 7.63 (d, 7.4 Hz), 7.51 (d, 7.4 Hz), 7.46 (d, 6.7 Hz), 7.25 (m), 5.22 (s), 5.08 (m), 4.57 (s), 4.44 (s), 4.41 (s), 4.29 (s), 4.24 (s), 1.45 (d, 6.7 Hz), 1.41 (d, 6.3 Hz), 1.34 (d, 6.7 Hz), 1.30 (d, 6.3 Hz).

Example 21

Ester Cleavage and Hydrosilylation Employing (κ⁵-N,N,N,P,P-$^{Ph_2PPr}$PDIMn) as a Catalyst In the glove box, a solution of 16.6 µL (0.135 mmol) of PhSiH₃ and 13.2 µL (0.135 mmol) of ethyl acetate in approximately 1 mL of benzene-$d_6$ was added to a 20 mL scintillation vial containing 0.0045 g (0.0067 mmol) of (κ⁵-N,N,N,P,P-$^{Ph_2PPr}$PDI)Mn. The resulting brown solution was transferred to a J. Young tube. After 5.5 hr, greater than 99% conversion was detected by ¹H NMR spectroscopy and the only organic product observed was PhSi(OEt)₃, suggesting that C—O bond cleavage takes place during the course of the reaction. A quartet at 3.85 ppm and a triplet at 1.17 ppm confirmed PhSi(OEt)₃ formation, which was observed along with residual PhSiH₃.

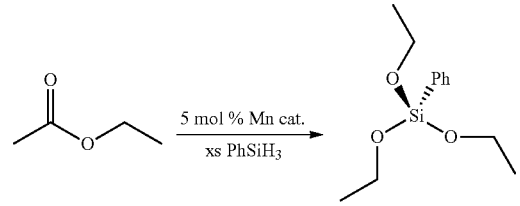

Examples 22-26

Alkyne Hydrosilylation Reactions Employing the Disclosed Metal Complexes

Example 22

Hydrosilylation of Phenylacetylene with Phenylsilane Using 0.5 Mol % of [(κ⁵-N,N,N,P,P-$^{Ph_2PPr}$PDI)Co][Cl]

Under an inert atmosphere a 4 mL vial was charged with 0.0047 g (0.00664 mmol) of [(κ⁵-N,N,N,P,P-$^{Ph_2PPr}$PDI)Co][Cl], 160 µL (1.323 mmol) phenylsilane and 0.150 µL (1.363 mmol) phenylacetylene. The [(κ⁵-N,N,N,P,P-$^{Ph2PPr}$PDI)Co][Cl] dissolved readily in the substrate mixture to create a brown solution. Reaction was stirred at ambient temperature for 24 hours, at which time it was exposed to air. An aliquot of the organic phase was added to 0.75 mL C₆D₆ and filtered through Celite® into an NMR tube. Greater than 99% conversion of phenylacetylene to alkene containing products was observed by ¹H NMR spectroscopy (TOF≈8.3 hr⁻¹ with respect to phenylacetylene) as a mixture of isomers. A doublet of triplets centered at 6.2 ppm and a doublet at 4.72 ppm were found representing the trans-olefin product, doublets were found for the cis-olefin product, and a series of small peaks representing a third product were located at 6.08, 5.74, and 4.98 ppm.

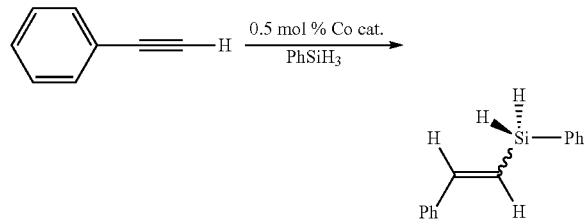

Example 23

Figure 19:
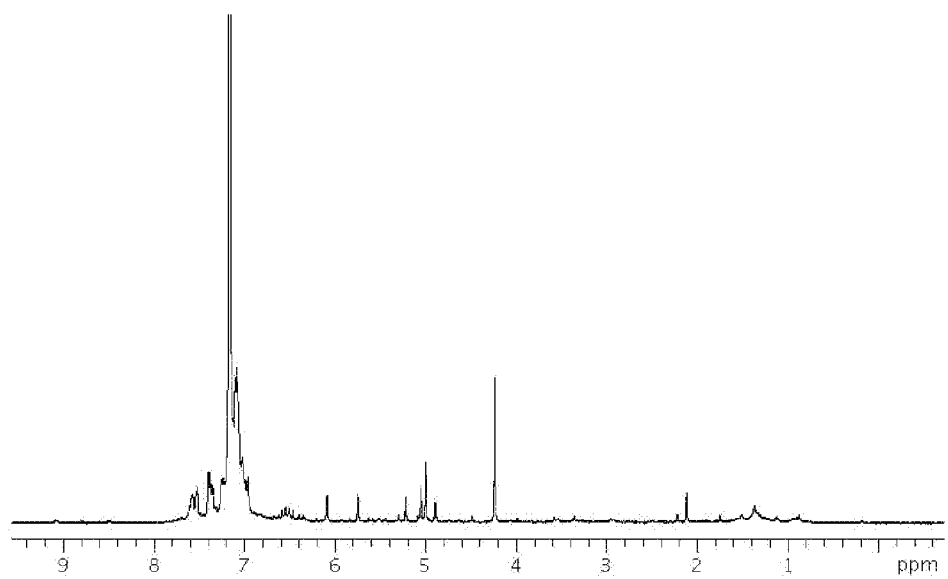
FIG. 19 illustrates the $^1$H NMR spectrum recorded following the hydrosilylation of phenylacetylene with phenylsilane using 10 mol % of ($\kappa^5$-N,N,N,N,N-$^{PyEt}$PDI)Fe.

Hydrosilylation of Phenylacetylene with Phenylsilane Using 10 Mol % of ($\kappa^5$-N,N,N,N,N-$^{PyEt}$PDI) Fe In a nitrogen filled glove box, a 20 mL reaction vial was charged with 0.001 g (0.002 mmol) of ($\kappa^5$-N,N,N,N, N-$^{PyEt}$PDI)Fe and 0.5 mL of benzene-$d_6$. A second vial was charged with 2.9 µL of PhSiH$_3$ (0.024 mmol), 2.6 µL of phenylacetylene (0.024 mmol), and 0.5 mL of benzene-$d_6$. The substrate mixture was added to the iron catalyst and the resulting solution was transferred into a J. Young tube. The tube was heated at 65° C. and ~90% conversion to a mixture of alkene containing products was observed within 25 min by $^1$H NMR spectroscopy. This spectrum is provided as FIG. 19.

Example 24

Hydrosilylation of Trimethylsilylacetylene with Phenylsilane Using 10 Mol % of ($\kappa^5$-N,N,N,N, N-$^{PyEt}$PDI)Fe In a nitrogen filled glove box, a 20 mL reaction vial was charged with 0.001 g (0.002 mmol) of ($\kappa^5$-N,N,N,N, N-$^{PyEt}$PDI)Fe and 0.5 mL of benzene-$d_6$. A second vial was charged with 3.2 µL (0.026 mmol) of PhSiH$_3$, 3.7 µL (0.026 mmol) of trimethylsilylacetylene, and 0.5 mL of benzene-$d_6$. The latter solution was added to the former and the reaction was transferred into a J. Young NMR tube. The tube was heated at 65° C. in oil bath and 91% conversion to an alkene containing product with $^1$H NMR resonances at 6.48 ppm and 6.38 ppm was observed by $^1$H NMR spectroscopy after 10 hr.

Example 25

Hydrosilylation of 3-Hexyne with Phenylsilane Using 10 Mol % of (0-N,N,N,N,N-$^{PyEt}$PDI)Fe In a nitrogen filled glove box, a 20 mL reaction vial was charged with 0.001 g (0.002 mmol) of ($\kappa^5$-N,N,N,N, N-$^{PyEt}$PDI)Fe and 0.5 mL of benzene-$d_6$. Another vial was charged with 2.9 µL (0.024 mmol) of PhSiH$_3$, 2.6 µL (0.023 mmol) of 3-hexyne, and 0.5 mL of benzene-$d_6$. The later solution was added to the former the reaction was transferred into a J. Young tube. The tube was heated at 85° C. for 5 hr, after which time a $^1$H NMR spectrum was recorded.

Analysis revealed 44% conversion (TOF≈1 hr$^{-1}$) into the desired hydrosilylated product.

$^1$H NMR (benzene-$d_6$): δ (ppm)=7.60, 6.06, 4.84, 2.18, 1.60, 0.93, 0.84.

Example 26

Hydrosilylation of Phenylacetylene with Phenylsilane Using 5 Mol % of ($\kappa^4$-N,N,N,P-$^{Ph}_2$$^{PPr}$PDI)Ni Under a nitrogen atmosphere a 20 mL scintillation vial was charged with 24.2 µL (0.22 mmol) of phenylacetylene, 27.1 µL (0.22 mmol) of phenylsilane and approximately 0.5 mL of benzene-$d_6$. The resulting light yellow solution was then added drop-wise into a separate 20 mL scintillation vial that had been previously charged with 7.4 mg (0.011 mmol) of ($\kappa^4$-N,N,N,P-$^{Ph}_2$$^{PPr}$PDI)Ni. The resulting olive green solution was then transferred into a J. Young NMR tube and sealed under a nitrogen atmosphere. Initial product formation (10%) was observed via $^1$H NMR spectroscopy 1 hr and 15 min after initiating the reaction. After 26 hr, approximately 83% conversion to predominantly trans-(Ph)(H)C=C(H)(SiH$_2$Ph) was observed by $^1$H NMR spectroscopy (a doublet of triplets centered at 6.20 ppm and a doublet at 4.72 ppm were found for one of the alkene hydrogen atoms and the remaining Si—H atoms, respectively).

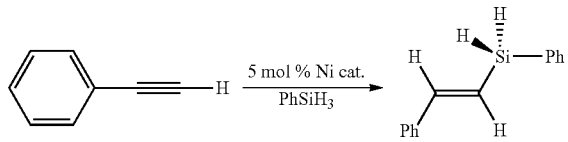

Examples 27-34

Additional Exemplary Preparation Methods for First-Row Metal Complexes

Example 27

Preparation of [N,N'-(2,6-pyridinediyldiethylidyne) bis[3-(diphenylphosphino)-1-propanamine]]MnH (hereafter $\kappa^5$-N,N,N,P,P-$^{Ph}_2$$^{PPr}$PDIMnH)

In an inert atmosphere glove box, a 250 mL round-bottomed flask was charged with 0.344 g (0.466 mmol) of $^{Ph}_2$$^{PPr}$PDIMnCl$_2$ in approximately 120 mL of toluene. The slurry was placed in a liquid nitrogen cooled cold well for an hour. A 20 mL scintillation vial was charged with 0.114 g (0.932 mmol) of NaEt$_3$BH in approximately 10 mL of toluene and it was also cooled for an hour. After being cooled, the NaEt$_3$BH solution was added to the $^{Ph}_2$$^{PPr}$PDIMnCl$_2$ slurry slowly while being stirred. The flask was then allowed to stir while warming to room temperature. A deep green color was observed after 20 minutes, which continued to darken over time.

After 12 h the resulting brownish-green solution was filtered through Celite® and the toluene was evacuated to obtain a dark solid. The solid was washed with pentane (4 aliquots of 5 mL) and quickly with 10 mL of ether (2 aliquots of 5 mL) to remove any free ligand generated in the reaction. The solid was then recrystallized from a concentrated toluene/pentane solution that was stored at −35° C.

overnight. Dark green crystals (125 mg, 0.187 mmol) were collected after drying and identified as κ⁵-N,N,N,P,P-$^{Ph}_2{}^{PPr}$PDIMnH.

Figure 20:
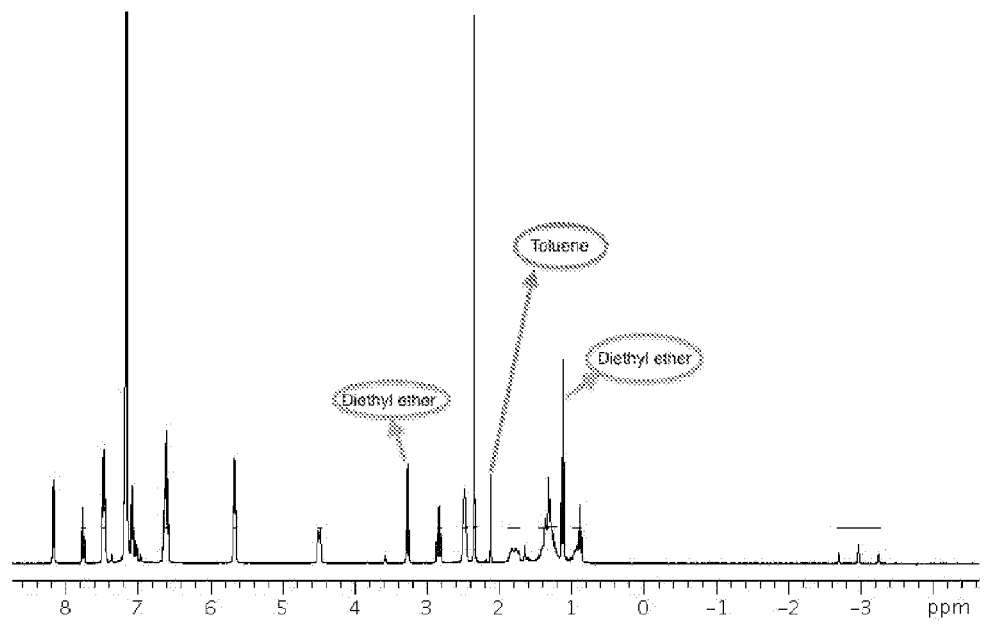
FIG. 20 illustrates the $^1$H NMR spectrum of $\kappa^5$-N,N,N, P,P-$^{Ph}_2{}^{PPr}$PDIMnH.
Figure 21:
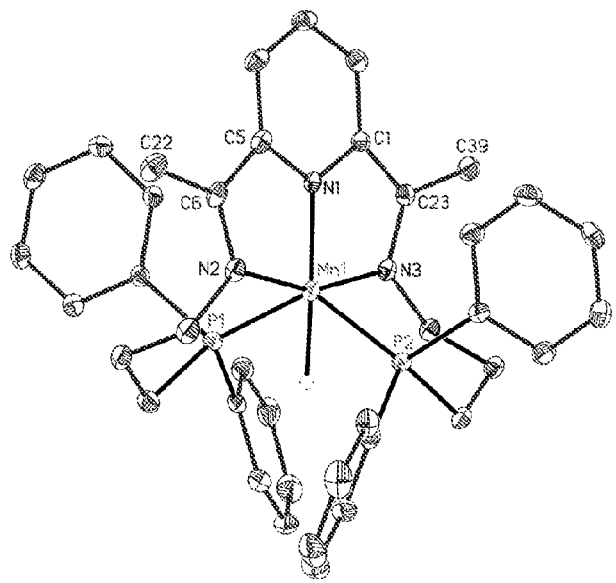
FIG. 21 illustrates the structure of $\kappa^5$-N,N,N,P, P-$^{Ph}_2{}^{PPr}$PDIMnH, as characterized by single crystal X-Ray diffraction.

¹H NMR 500 MHz (benzene-d₆): 8.17 (d, $J_{H-H}$=8.1 Hz, 2H, pyridine), 7.76 (t, $J_{H-H}$=8.1 Hz, 1H, pyridine), 7.47 (t, $J_{H-H}$=8.1 Hz, 4H, phenyl), 7.09 (m, 4H, phenyl), 6.61 (m, 6H, phenyl), 5.66 (t, $J_{H-H}$=8.1 Hz, 4H, phenyl), 4.50 (d, $J_{H-H}$=11.4 Hz, 2H, CH₂), 2.83 (t, $J_{H-H}$=11.2 Hz, 2H, CH₂), 2.48 (broad m, 4H, CH₂), 2.34 (s, 6H, CH₃), 1.78 (broad m, 2H, —CH₂), 1.36 (broad m, 2H, —CH₂), -2.98 (t, $J_{P-H}$=112.4 Hz, 1H, Mn—H). This spectrum is included as FIG. 20. ¹³C NMR 500 MHz (benzene-d₆): 231.5, 189.9, 170.8, 154.6, 151.5, 133.6, 133.5, 133.3, 129.9, 129.7, 128.0, 120.9, 115.5, 110.4, 75.2, 74.9, 57.5, 29.9, 14.6. This complex has also been characterized by single crystal X-ray diffraction (FIG. 21).

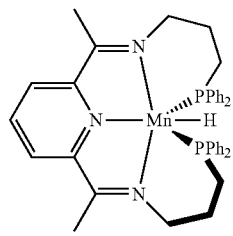

κ⁵-N,N,N,P,P-$^{Ph}_2{}^{PPr}$PDIMnH

Example 28

Preparation of [(N,N'-(2,6-pyridinediyldiethylidyne) bis(3-(diphenylphosphino)-1-propanamine))FeBr][Br] (hereafter [κ⁵-N,N,N,P,P-$^{Ph2PPr}$PDIFeBr][Br])

In a nitrogen-filled glove box, a 20 mL scintillation vial was charged with 0.109 g (0.506 mmol) of FeBr₂ in 5 mL THF and stirred for about 5 min. Another vial was charged with 0.310 g (0.506 mmol) of $^{Ph}_2{}^{PPr}$PDI in 10 mL THF. This solution was then added to the solution of FeBr₂ in THF and immediately turned purple in color. After stirring for 18 h, the reaction mixture was filtered through Celite®, the solvent was removed, and the resulting purple solid was washed with ether and dried to yield 0.343 g (82%) of [κ⁵-N,N,N,P,P-$^{Ph}_2{}^{PPr}$PDIFeBr][Br].

Figure 22:
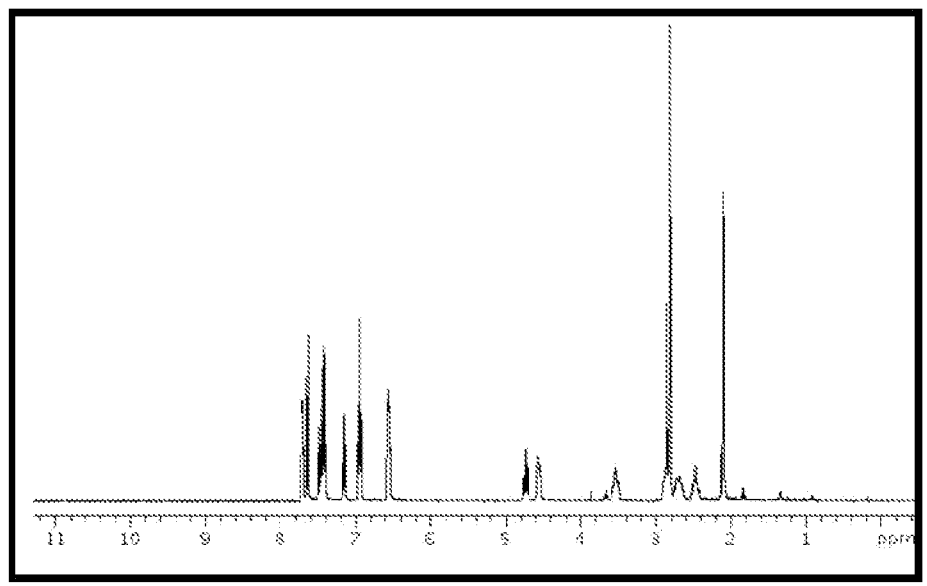
FIG. 22 illustrates the $^1H$ NMR spectrum of [$\kappa^5$-N,N,N, P,P-$^{Ph}_2{}^{PPr}$PDIFeBr][Br].

¹H NMR (acetone-d₆, 25° C.): 7.70 (m, 4H, phenyl), 7.62 (d, $J_{H-H}$=7.7 Hz, 2H, m-pyridine), 7.50-7.39 (m, 8H, phenyl), 7.15 (t, $J_{H-H}$=7.7 Hz, 1H, p-pyridine), 6.95 (t, $J_{H-H}$=7.5 Hz, 4H, phenyl), 6.55 (m, 4H, phenyl), 4.73 (m, 2H, CH₂), 4.56 (m, 2H, CH₂), 3.53 (m, 2H, CH₂), 2.87 (m, 2H, CH₂), 2.80 (s, 6H, CH₃), 2.70 (m, 2H, CH₂), 2.48 (m, 2H, CH₂). This spectrum is included as FIG. 22.

Figure 23:
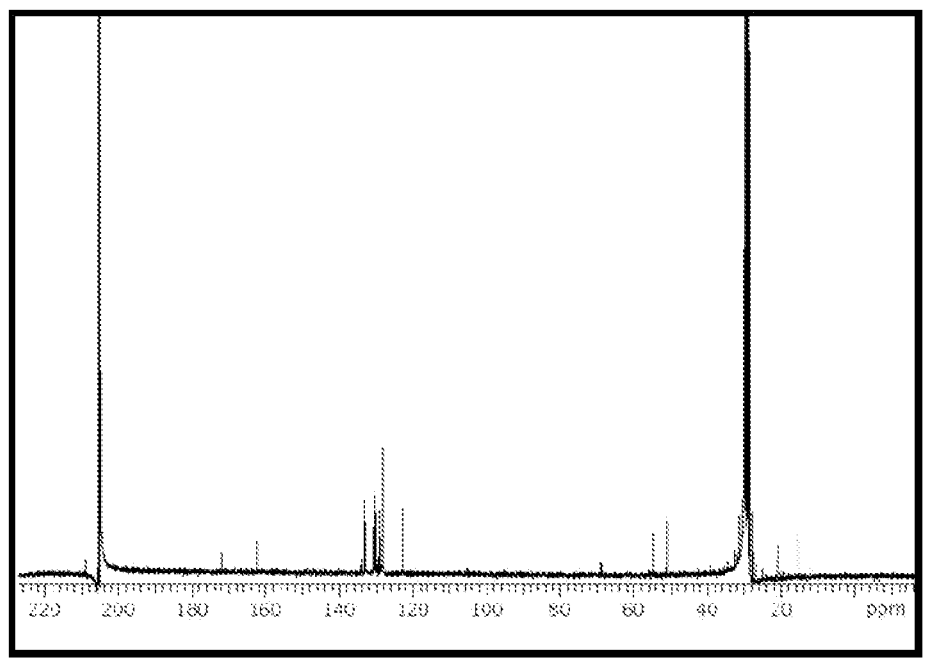
FIG. 23 illustrates the $^{13}$C NMR spectrum of [$\kappa^5$-N,N,N, P,P-$^{Ph}_2{}^{PPr}$PDIFeBr][Br].

¹³C NMR (acetone-d₆, 25° C.): 171.72 (d, phenyl), 162.39 (s, C=N), 135.03 (t, phenyl), 133.86 (t, phenyl), 131.42 (t, phenyl), 131.11 (s), 129.19 (m, phenyl), 129.78 (s, phenyl), 123.75 (s, phenyl), 69.65 (t, CH₂), 55.66 (d, CH₂), 51.98 (s, CH₂), 28.72 (s). This spectrum is included as FIG. 23.

Figure 24:
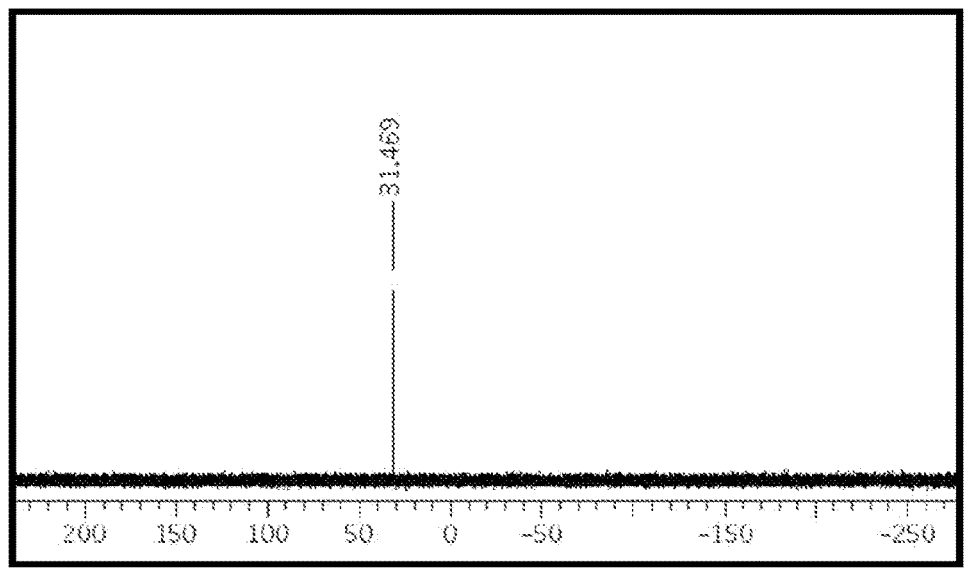
FIG. 24 Illustrates the $^{31}$P NMR spectrum of [$\kappa^5$-N,N,N, P,P-$^{Ph}_2{}^{PPr}$PDIFeBr][Br].

³¹P NMR (acetone-d₆, 25° C.): 31.46 (s, PPh₂). This spectrum is included as FIG. 24.

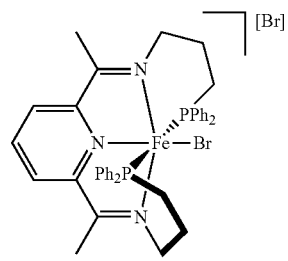

[κ⁵-N,N,N,P,P-$^{Ph}_2{}^{PPr}$PDIFeBr][Br]

Example 29

Preparation of [N,N'-(2,6-pyridinediyldiethylidyne) bis[3-(diphenylphosphino)-1-propanamine]]Fe (hereafter κ⁵-N,N,N,P,P-$^{Ph}_2{}^{PPr}$PDIFe)

In a nitrogen-filled glove box, a 20 mL scintillation vial was charged with 0.158 g (0.191 mmol) of [κ⁵-N,N,N,P,P-$^{Ph}_2{}^{PPr}$PDIFeBr][Br] and 10 mL of THF. Another vial was charged with 3.81 g (19.05 mmol) of Hg and 5 mL of THF. To this, 0.219 g (0.953 mmol) of freshly cut Na metal was added and resulting amalgam was allowed to stir for 20 min. To this mixture, a slurry of [κ⁵-N,N,N,P,P-$^{Ph}_2{}^{PPr}$PDIFeBr][Br] in THF was transferred slowly while stirring. After stirring for 12 h, the purple colored solution turned brown in color. The solution turned greenish-brown after 24 h.

After stirring for 2 d, the greenish-brown solution was filtered through Celite® and THF was removed under vacuum. After washing with pentane (10 mL), a greenish-brown solid was obtained which was redissolved in toluene (10 mL) and filtered through Celite®. The toluene was removed under vacuum to obtain 0.100 g (78%) of a fine greenish-brown solid product identified as κ⁵-N,N,N,P,P-$^{Ph}_2{}^{PPr}$PDIFe.

Figure 25:
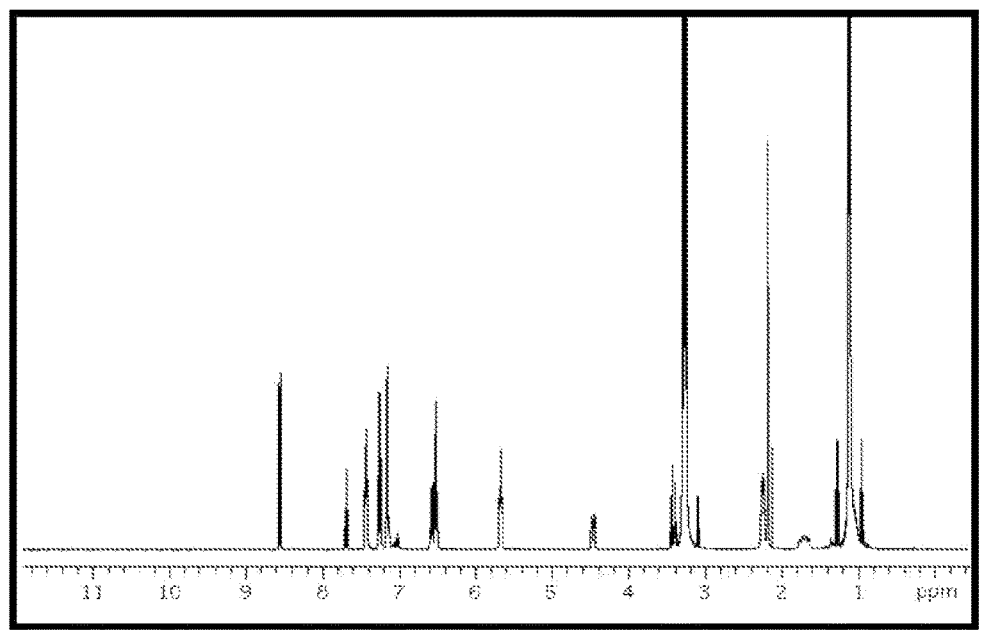
FIG. 25 illustrates the $^1$H NMR spectrum of $\kappa^5$-N,N,N, P,P-$^{Ph}_2{}^{PPr}$PDIFe.

¹H NMR (benzene-d₆, 25° C.): 8.54 (d, $J_{H-H}$=7.7 Hz, 2H, m-pyridine), 7.68 (t, $J_{H-H}$=7.7 Hz, 1H, p-pyridine), 7.43 (t, $J_{H-H}$=7.0 Hz, 4H, phenyl), 7.25 (t, $J_{H-H}$=7.5 Hz, 4H, phenyl), 6.59-6.57 (m, 6H, phenyl), 5.66 (t, $J_{H-H}$=8.5 Hz, 4H, phenyl), 4.48-4.43 (m, 2H, phenyl), 3.42 (m, 4H, CH₂), 2.24 (m, 4H, CH₂), 2.17 (s, 6H, CH₃), 1.72 (m, 2H, CH₂). This spectrum is included as FIG. 25.

Figure 26:
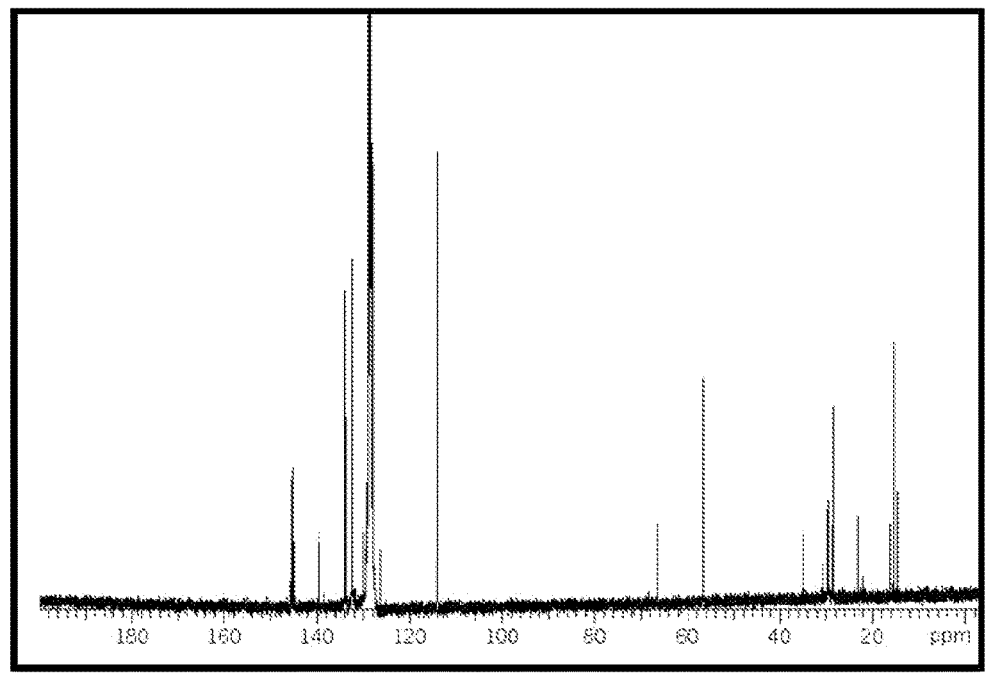
FIG. 26 illustrates the $^{13}$C NMR spectrum of $\kappa^5$-N,N,N, P,P-$^{Ph}_2{}^{PPr}$PDIFe.

¹³C NMR (benzene-d₆, 25° C.): 144.46 (t, phenyl), 145.21 (t, phenyl), 145.05 (t, phenyl), 139.55 (t, phenyl), 133.80 (t, phenyl), 128.01 (t, phenyl), 114.02 (s, pyridine), 113.84 (s, pyridine), 56.69 (s, CH₂), 30.79 (s, CH₂), 29.52 (t, CH₂P), 16.16 (s, CH₃). This spectrum is included as FIG. 26.

Figure 27:
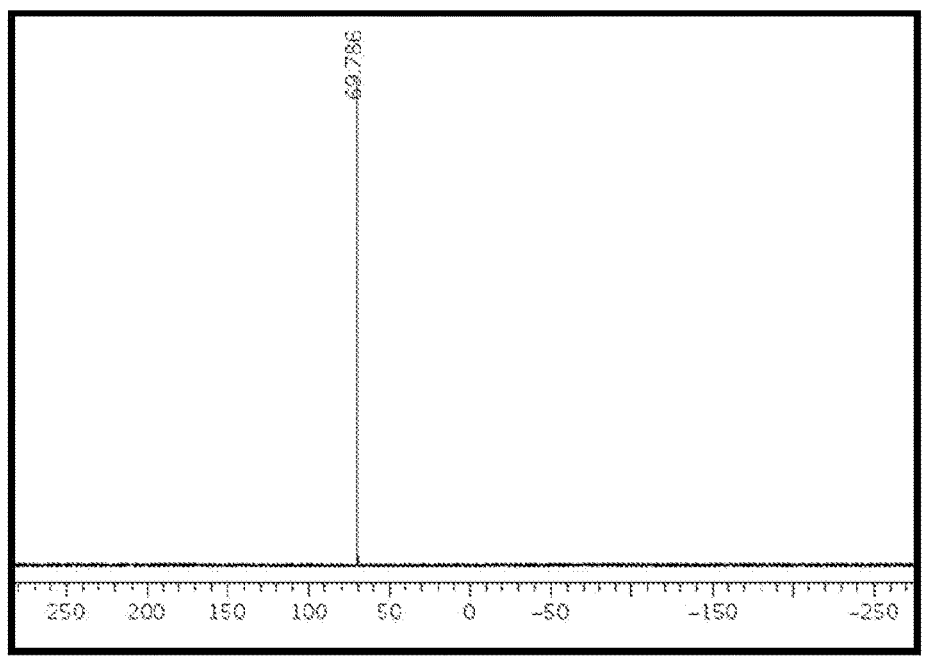
FIG. 27 illustrates the $^{31}$P NMR spectrum of $\kappa^5$-N,N,N, P,P-$^{Ph}_2{}^{PPr}$PDIFe.

³¹P NMR (benzene-d₆, 25° C.): 69.79 (s, PPh₂). This spectrum is included as FIG. 27.

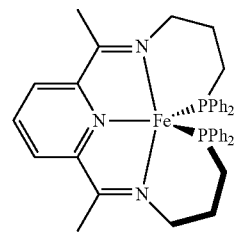

κ$^5$-N,N,N,P,P-$^{Ph}_2{}^{PPr}$PDIFe

Example 30

Preparation of [(N,N'-(2,6-pyridinediyldiethylidyne)bis(3-(diphenylphosphino)-1-propanamine))FeH][BF$_4$] (hereafter [κ$^5$-N,N,N,P,P-$^{Ph}_2{}^{PPr}$PDIFeH][BF$_4$])

In a nitrogen filled glove box, a 100 mL round-bottomed flask was charged with 0.103 g (0.154 mmol) of κ$^5$-N,N,N,P,P-$^{Ph}_2{}^{PPr}$PDIFe and 30 mL diethyl ether. A vial was charged with 21.1 Å (0.154 mmol) of HBF$_4$.OEt$_2$ and 2 mL of diethyl ether. This solution was then added to the stirred solution of κ$^5$-N,N,N,P,P-$^{Ph_2PPr}$PDIFe. Immediately, the reaction color changed from greenish-brown to red and a precipitate formed. After stirring for 10 min, the resulting solution was filtered through Celite®, which left a green solid product on top of the Celite®. The green solid was then dissolved in acetone and filtered through Celite® and the solvent was removed under vacuum. The residue was scraped with pentane (5 mL) to obtain 0.050 g (43%) of a fine green powder identified as [κ$^5$-N,N,N,P,P-$^{Ph}_2{}^{PPr}$PDIFeH][BF$_4$].

Figure 28:
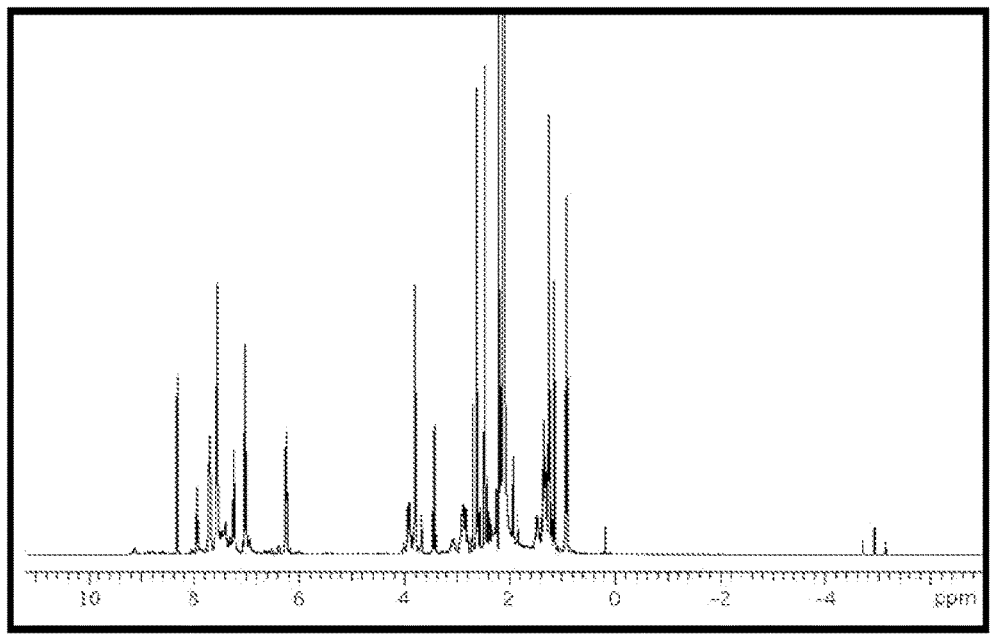
FIG. 28 illustrates the $^1$H NMR spectrum of [$\kappa^5$-N,N,N, P,P-$^{Ph}_2{}^{PPr}$PDIFeH][BF$_4$].

$^1$H NMR (acetone-d$_6$, 25° C.): 8.30 (d, $J_{H-H}$=7.9 Hz, 2H, m-pyridine), 7.91 (t, $J_{H-H}$=7.9 Hz, 1H, p-pyridine), 7.69 (m, 4H, phenyl), 7.53 (m, 6H, phenyl), 7.24 (t, $J_{H-H}$=15 Hz, 2H, phenyl), 7.01 (m, 4H, phenyl), 6.24 (t, $J_{H-H}$=17.3 Hz, 4H, phenyl), 3.91 (m, 2H, CH$_2$), 3.80 (m, 2H, CH$_2$), 2.88 (m, 2H, CH$_2$), 2.46 (t, $J_{P-H}$=5.5 Hz, 6H, CH$_3$), 2.41 (m, 2H, CH$_2$), 1.92 (m, 2H, CH$_2$), 1.33 (m, 2H, CH$_2$), −4.94 (t, $J_{P-H}$=86 Hz, 1H, Fe—H). This spectrum is included as FIG. 28.

Figure 29:
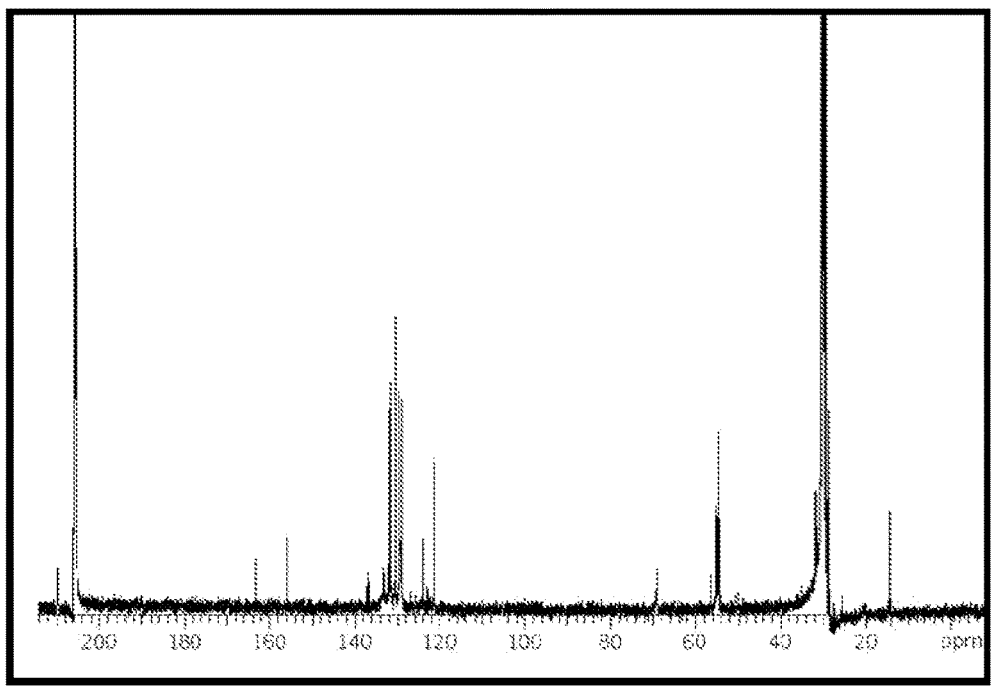
FIG. 29 illustrates the $^{13}$C NMR spectrum of [$\kappa^5$-N,N,N, P,P-$^{Ph}_2{}^{PPr}$PDIFeH][BF$_4$].

$^{13}$C NMR (acetone-d$_6$, 25° C.): 163.30 (t, phenyl), 155.73 (s), 136.75 (t, phenyl), 128.17 (t, phenyl), 120.73 (s, pyridine), 55.73 (s), 54.56-53.97 (m, CH$_2$), 29.33 (m), 29.19 (m, CH$_2$), 28.75 (t, CH$_2$), 13.52 (s, CH$_3$). This spectrum is included as FIG. 29.

Figure 30:
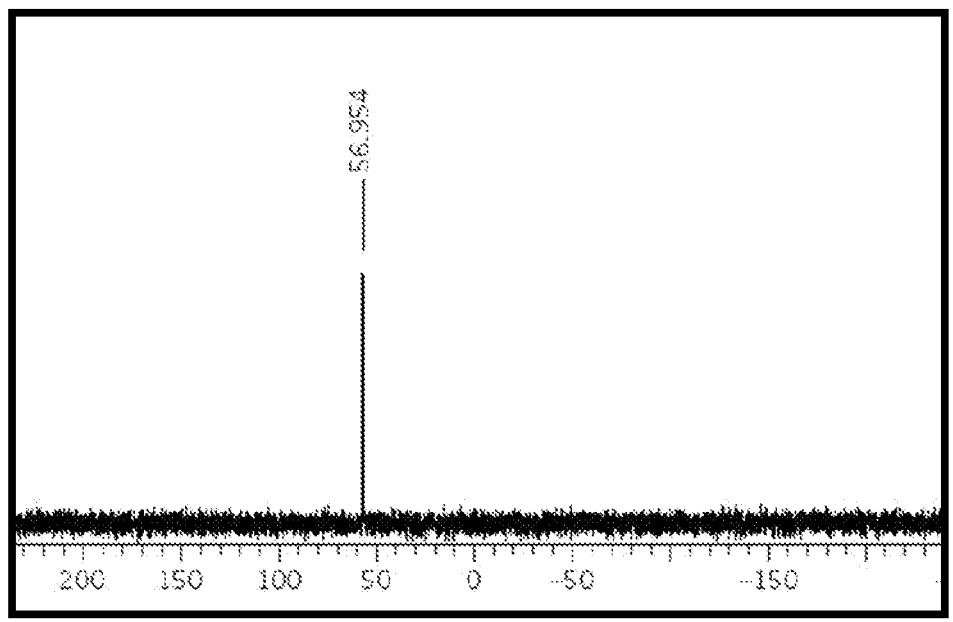
FIG. 30 illustrates the $^{31}$P NMR spectrum of [$\kappa^5$-N,N,N, P,P-$^{Ph}_2{}^{PPr}$PDIFeH][BF$_4$].

$^{31}$P NMR (acetone-d$_6$, 25° C.): 56.95 (s, PPh$_2$). This spectrum is included as FIG. 30.

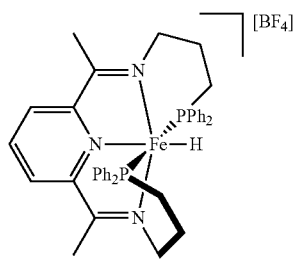

[κ$^5$-N,N,N,P,P-$^{Ph}_2{}^{PPr}$PDIFeH][BF$_4$]

Example 31

Preparation of [N,N'-(1,2-dimethyl-1,2-ethanediylidene)bis[3-(diphenylphosphino)-1-propanamine]]CoCl$_2$ (hereafter $^{Ph_2PPr}$DICoCl$_2$)

Under an inert atmosphere, a 20 mL scintillation vial was charged with 0.122 g (0.94 mmol) of CoCl$_2$ which was partly dissolved in THF and allowed to stir for 5 min forming a cloudy light blue solution. A 10 mL pale yellow THF solution containing 0.253 g (0.471 mmol) of $^{Ph2PPr}$DI was added dropwise, while stirring to the cobalt solution. The color instantly darkened and turned cloudy. The reaction was allowed to stir for 24 h and was then filtered through Celite®. Some insoluble, dark material remained in the reaction vial, which was washed through with 4 mL aliquots of THF. The solvent was removed in vacuo and the solid that remained was washed with diethyl ether to remove residual free ligand. After drying, 0.154 g (0.230 mmol, 49%) of a dark green microcrystalline solid was recovered and identified as $^{Ph}_2{}^{PPr}$DICoCl$_2$.

$^1$H NMR (acetone-d$_6$, 25° C.): 10.31 (77), 2.45 (11), 1.28 (16), 0.00 (1158), −4.36 (797).

Example 32

Preparation of [N,N'-(1,2-dimethyl-1,2-ethanediylidene)bis[3-(diphenylphosphino)-1-propanamine]]CoH (hereafter κ$^4$-N,N,P,P-$^{Ph}_2{}^{PPr}$DICoH)

Under an inert atmosphere, a 20 mL scintillation vial was charged with 0.1845 g (0.277 mmol)$^{Ph2PPr}$DICoCl$_2$ and 10 mL toluene. Another vial was charged with 0.277 mL (0.277 mmol) of a 1.0 M toluene solution of NaEt$_3$BH and 3 mL toluene. The NaEt$_3$BH solution was then added to the solution of $^{Ph}_2{}^{PPr}$DICoCl$_2$ in a dropwise fashion while stirring and the reaction was allowed to stir for 24 h. Following filtration, the solvent was removed in vacuo to yield a dark microcrystalline solid identified as κ$^4$-N,N,P,P-$^{Ph}_2{}^{PPr}$DICoH.

Figure 31:
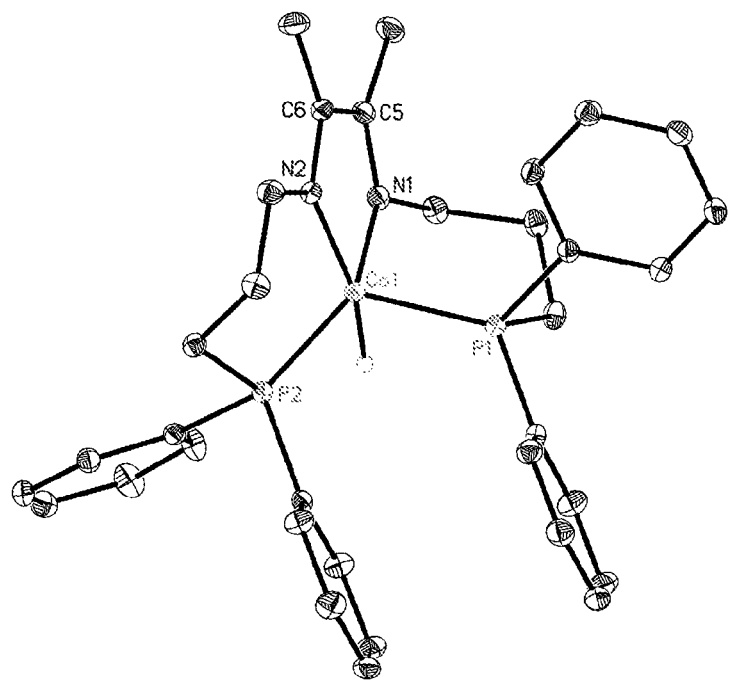
FIG. 31 illustrates the structure of $\kappa^4$-N,N,P, P-$^{Ph}_2{}^{PPr}$DICoH, as characterized by single crystal X-ray diffraction.

$^1$H NMR (C$_6$D$_6$, 25° C.): 7.63 (t, 8 Hz, 2H), 7.12 (t, 8 Hz, 4H), 6.98 (m, 4H), 6.89 (m, 2H), 6.83 (t, 7 Hz, 4H), 6.72 (m, 2H), 4.81 (t, 12 Hz, 1H), 4.52 (m, 1H), 3.09 (m, 1H), 2.5 (m, 2H), 2.11 (m, 4H), 1.51 (dd, 18 Hz, 10 Hz, 6H), 0.87 (t, 7 Hz, 1H), −19.82 (dd, 90 Hz, 39 Hz, 1H). $^{31}$P NMR (C$_6$D$_6$, 25° C.): 76.08 (CoP), 51.33 (CoP). This complex has also been characterized by single crystal X-ray diffraction (FIG. 31).

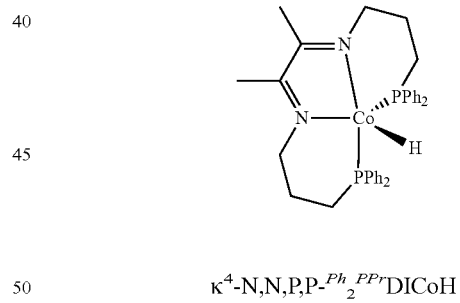

κ$^4$-N,N,P,P-$^{Ph}_2{}^{PPr}$DICoH

Example 33

Preparation of [N,N'-(2,6-pyridinediyldiethylidyne)bis(2-pyridineethanamine)]CoCl$_2$ (hereafter $^{PyEt}$PDICoCl$_2$)

In a nitrogen-filled glove box, a 100 mL round-bottomed flask was charged with 0.105 g of CoCl$_2$ (0.487 mmol) and 10 mL of THF. To this, 0.185 g (0.499 mmol) of $^{PyEt}$PDI dissolved in 10 mL of THF was added slowly while stirring. A light green precipitate began to form following ligand addition. After stirring for 15 h, the light green solid was collected on a borosilicate filtration frit. After washing with toluene and ether followed by drying under vacuum for 1 h, 0.220 g (77%) of a green solid identified as $^{PyEt}$PDICoCl$_2$ was obtained.

$^1$H NMR (chloroform-d, 20° C.): 92.15 (389), 20.92 (20), 16.44 (1498), 14.47 (1461), 1.82 (23), 1.46 (31).

Example 34

Preparation of [2-[(2-NC$_5$H$_4$)CH$_2$CH$_2$NCH(CH$_3$)](NC$_5$H$_4$)-6-[C(CH$_3$)═NCH$_2$CH$_2$(2-NC$_5$H$_4$)]]Co (hereafter κ$^4$-N,N,N,N-$^{PyEt}$PDIHCo)

In a nitrogen-filled glove box, a 100 mL round-bottomed flask was charged with 0.118 g (0.201 mmol) of $^{PyEt}$PDI-CoCl$_2$ and 10 mL of toluene and kept at −35° C. for 30 min. To this, 0.023 g (1.00 mmol) of 1.0 M toluene solution of NaEt$_3$BH was added slowly while stirring. The solution turned bluish-green within 30 min. After 10 h of stirring, the solution was filtered through Celite® and the solvent was removed under vacuum to obtain 0.075 g (86%) of a dark bluish-green solid identified as κ$^4$-N,N,N,N-$^{PyEt}$PDIHCo. Analysis for C$_{25}$H$_{26}$N$_5$Co: Calcd C, 64.03; H, 6.17; N, 16.23. Found: C, 64.05; H, 6.36; N, 15.95.

Figure 32:
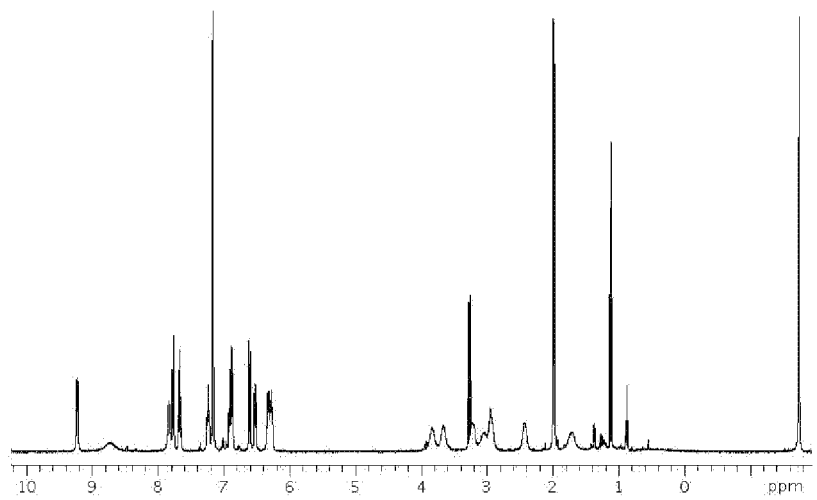
FIG. 32 illustrates the $^1$H NMR spectrum of $\kappa^4$-N,N,N, N-$^{PyEt}$PDIHCo.

$^1$H NMR (benzene-d$_6$, 20° C.): 9.24 (d, 6.8 Hz, 1H), 8.69 (broad, 1H), 7.83 (broad, 1H), 7.77 (d, 8.4 Hz, 1H), 7.67 (t, 7.2 Hz, 1H), 7.24 (t, 7.6 Hz, 1H), 6.88 (m, 9.6 Hz, 2H), 6.60 (d, 7.6 Hz, 1H), 6.30 (m, 2H), 3.83 (broad, 1H), 3.66 (broad, 1H), 3.21 (broad, 2H), 3.04 (broad, 1H), 2.92 (broad, 2H), 2.41 (broad, 1H), 1.98 (d, 6.8 Hz, 3H), 1.71 (broad, 1H), −1.74 (s, 3H). This spectrum is included as FIG. 32.

Figure 33:
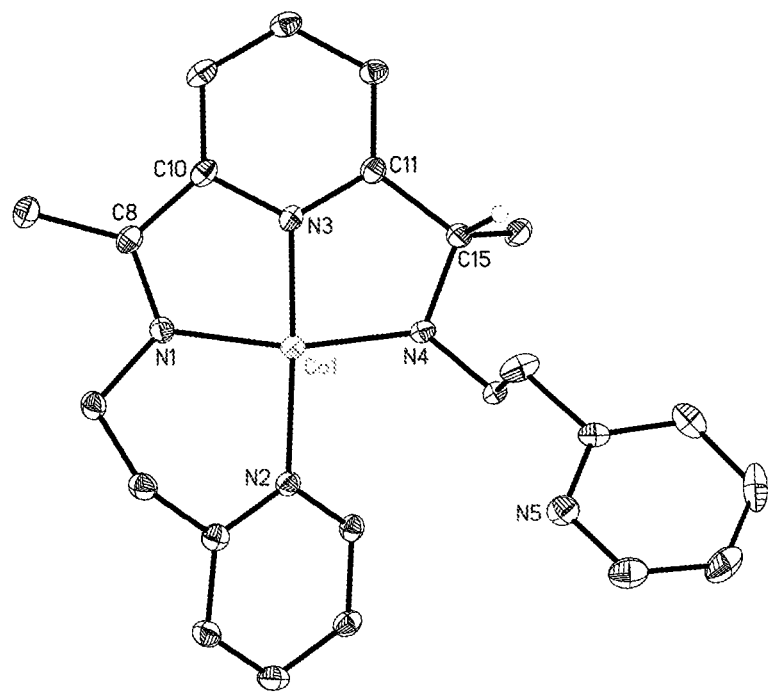
FIG. 33 illustrates the structure of $\kappa^4$-N,N,N,N-$^{PyEt}$PDI-HCo, as characterized by single crystal X-ray diffraction.

$^{13}$C NMR (benzene-d$_6$): 178.99, 162.81, 162.29, 153.67, 152.34, 134.55, 134.40, 132.55, 129.20, 123.22, 123.15, 122.86, 120.59, 114.93, 103.21, 72.84, 50.06, 49.13, 47.32, 38.13, 24.51, 20.68. This complex has also been characterized by single crystal X-ray diffraction (FIG. 33).

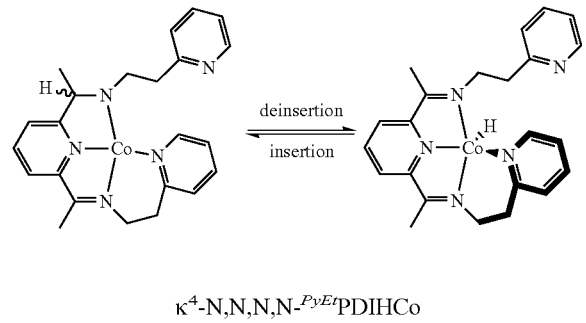

κ$^4$-N,N,N,N-$^{PyEt}$PDIHCo

Examples 35-38

Ketone Hydrosilylation Reactions Employing the Disclosed Metal Complexes

Example 35

Hydrosilylation of Acetophenone with Phenylsilane Using 0.1 Mol % of κ$^5$-N,N,N,P,P-$^{Ph}{}_2{}^{PPr}$PDIMnH In the glove box, a mixture of 0.369 mL (2.99 mmol) of PhSiH$_3$ and 0.349 mL (2.99 mmol) of acetophenone was added to a 20 mL scintillation vial containing 0.002 g (0.00299 mmol) of κ$^5$-N,N,N,P,P-$^{Ph}{}_2{}^{PPr}$PDIMnH. The resulting brownish-green solution was stirred for 4 min and then exposed to air to deactivate the catalyst. The resulting colorless organic solution was then filtered through a Celite® column and then a $^1$H NMR spectrum was recorded in benzene-d$_6$ solution.

Approximately 87% conversion of the acetophenone to PhSiH(OCH(Me)(Ph))$_2$ was confirmed by $^1$H NMR spectroscopy and evidence for an enantiomeric mixture of products was detected. PhSiH(OCHMePh)$_2$: $^1$H NMR 400 MHz (benzene-d$_6$): 7.72 (m, 2H, phenyl), 7.25 (m, 4H phenyl), 7.15 (m, 9H, phenyl), 5.28 (s, 1H, SiH), 5.02 (m, 2H, CH), 1.40 (m, 6H, CH$_3$). The presence of unreacted PhSiH$_3$ was confirmed by the signal at 4.23 ppm.

Example 36

Hydrosilylation of Cyclohexanone with Phenylsilane Using 0.1 Mol % of κ$^5$-N,N,N,P, P-$^{Ph}{}_2{}^{PPr}$PDIMnH In the glove box, a mixture of 0.369 mL (2.99 mmol) of PhSiH$_3$ and 0.301 mL (2.99 mmol) of cyclohexanone was added to a 20 mL scintillation vial containing 0.002 g (0.00299 mmol) of κ$^5$-N,N,N,P,P-$^{Ph}{}_2{}^{PPr}$PDIMnH. The resulting brownish-green solution was stirred for 4 min and then exposed to air to deactivate the catalyst.

Approximately 80% conversion of the cyclohexanone to PhSiH(OCy)$_2$ was confirmed by $^1$H NMR spectroscopy. PhSiH(OCy)$_2$: $^1$H NMR 400 MHz (benzene-d$_6$): 7.79 (m, 2H, phenyl), 7.26 (m, 3H, phenyl), 5.28 (s, 1H, Si—H), 3.96 (m, 2H, CH), 1.88 (m, 6H, CH$_2$), 1.65 (m, 6H, CH$_2$), 1.54 (m, 6H, CH$_2$), 1.31 (m, 2H, CH$_2$). The presence of unreacted PhSiH$_3$ was confirmed by the signal at 4.23 ppm.

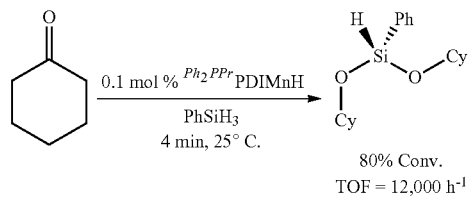

80% Conv.
TOF = 12,000 h$^{-1}$

Example 37

Hydrosilylation of Cyclohexanone with Phenylsilane Using 1 Mol % of [κ$^5$-N,N,N,P, P-$^{Ph}{}_2{}^{PPr}$PDIFeH][BF$_4$]

In a nitrogen filled glove box, a 2 mL reaction vial was charged with 0.0024 g (0.0032 mmol) of [κ$^5$-N,N,N,P, P-$^{Ph}{}_2{}^{PPr}$PDIFeH][BF$_4$]. To this, 39.1 μL (0.317 mmol) of PhSiH$_3$ followed by 32.8 μL (0.317 mmol) of cyclohexanone were added. After 24 h the reaction vial was removed from the glove box and exposed to air. Upon exposure to air, the green solution turned into a colorless solution. To one drop of this colorless solution, 0.5 mL of benzene-d$_6$ was added and the solution was filtered through Celite® and a $^1$H NMR spectrum was recorded.

Figure 34:
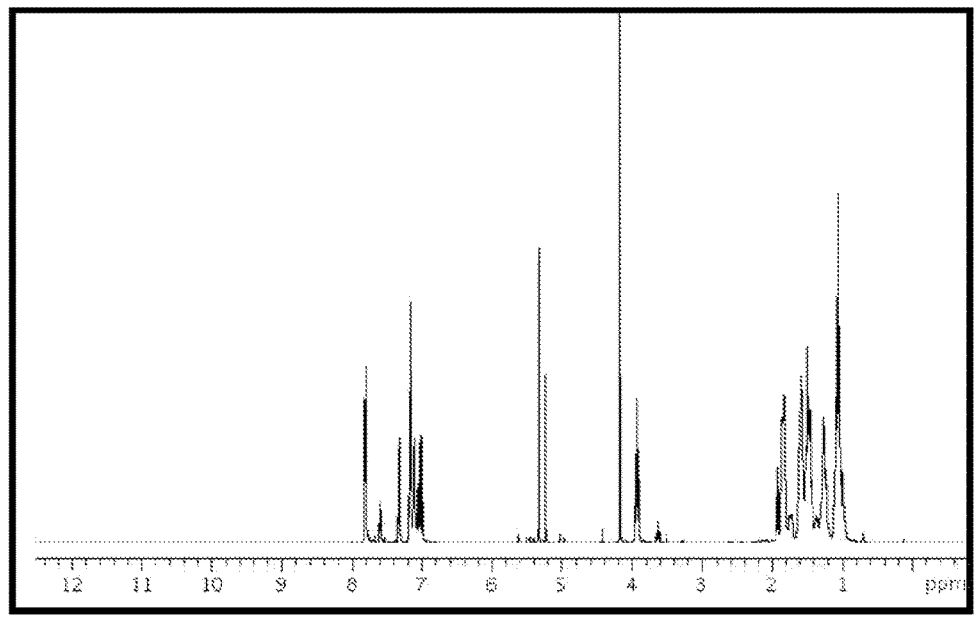
FIG. 34 illustrates the $^1$H NMR spectrum of silane products of the hydrosilylation described in Example 37.

Conversion of cyclohexanone (75%) to the mono- and di-hydrosilylated products were observed by $^1$H NMR spectroscopy (in a 4:1 ratio, respectively). $^1$H NMR (benzene-d$_6$, 25° C.): 5.32 (Si—H for PhSiH(OCy)$_2$), 5.23 (Si—H for PhSiH$_2$(OCy)), 4.16 (PhSiH$_3$), 3.92 (C—H for PhSiH(OCy)$_2$), 3.62 (C—H for PhSiH$_2$(OCy)). This spectrum is included as FIG. 34.

Example 38

Hydrosilylation of Cyclohexanone with Phenylsilane Using 5 Mol % of κ$^4$-N,N,N,N-$^{PyEt}$PDIHCo In a nitrogen filled glove box, a 20 mL reaction vial was charged with 1 mg (0.002 mmol) of 0-N,N,N,N-$^{PyEt}$PDIHCo and 0.5 mL of $C_6D_6$. Another vial was charged with 5.7 μL of $PhSiH_3$, 4.8 μL of cyclohexanone, and 0.5 mL of $C_6D_6$. The solutions were combined and the reaction was transferred to a J. Young NMR tube.

After remaining at ambient temperature for 15 h, 23% of the cyclohexanone had been hydrosilylated, as judged by $^1$H NMR spectroscopy. $^1$H NMR (400 MHz, benzene-$d_6$): 7.86, 7.65, 7.38, 5.32, 5.29, 3.96, 3.68, 1.91, 1.78, 1.64, 1.53, 1.42.

Example 39 Ester Dihydrosilylation Employing the Disclosed Metal Complexes

Example 39

Hydrosilylation of Ethyl Acetate with Phenylsilane Using 1 Mol % of $κ^5$-N,N,N,P,P-$^{Ph}_2$$^{PPr}$PDIMnH In the glove box, a solution of 0.037 mL (0.299 mmol) of $PhSiH_3$ and 0.029 mL (0.299 mmol) of ethyl acetate in approximately 1 mL of benzene-$d_6$ was added to a 20 mL scintillation vial containing 0.002 g (0.00299 mmol) of $κ^5$-N,N,N,P,P-$^{Ph}_2$$^{PPr}$PDIMnH. The resulting brown solution was transferred to a J. Young NMR tube.

More than 99% conversion of the ethyl acetate to $PhSi(OCH_2CH_3)_3$ was detected by $^1$H NMR spectroscopy after 7 h. A quartet at 3.85 ppm and a triplet at 1.17 ppm suggested the formation of ethyl environments through a C—O bond-breaking pathway. $PhSi(OCH_2CH_3)_3$: 7.87 (m, 2H, phenyl), 7.23 (m, 3H, phenyl), 3.85 (q, $J_{H-H}$=7.1 Hz, 6H, $CH_2$), 1.17 (t, $J_{H-H}$=7.0 Hz, 9H, $CH_3$). A small quantity of $PhSiH_3$ was observed at 7.38, 7.07 and 4.23 ppm.

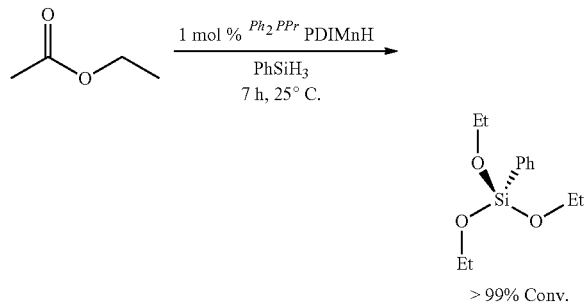

> 99% Conv.

Example 40 Alkene Hydrosilylation Employing the Disclosed Metal Complexes

Example 40

Hydrosilylation of 1-Hexene with Phenylsilane Using 5 Mol % of $κ^4$-N,N,P,P-$^{Ph}_2$$^{PPr}$DICoH Under an inert atmosphere, a J. Young tube was charged with 5.7 mg (0.0095 mmol) of $κ^4$-N,N,P,P-$^{Ph}_2$$^{PPr}$DICoH, 23.5 μL (0.1911 mmol) phenylsilane, 23.9 μL (0.1911 mmol) 1-hexene, and 0.5 mL $C_6D_6$. After 1 week at ambient temperature, 20% of the 1-hexene had been hydrosilylated to form $PhSiH_2$($^n$Hex), as judged by the multiplet observed at 4.34 ppm in the $^1$H NMR spectrum of the reaction mixture.

Examples 41-46

Alkyne Hydrosilylation Employing the Disclosed Metal Complexes

Example 41

Hydrosilylation of Phenylacetylene with Phenylsilane Using 5 Mol % of $κ^4$-N,N,P,P-$^{Ph}_2$$^{PPr}$DICoH Under an inert atmosphere, a J. Young tube was charged with 5.0 mg (0.0084 mmol) of $κ^4$-N,N,P,P-$^{Ph}_2$$^{PPr}$DICoH, 19.5 μL (0.158 mmol) phenylsilane, 18.4 μL (0.1676 mmol) phenylacetylene, and 0.5 mL $C_6D_6$. After 3 h, greater than 99% conversion of the phenylacetylene to a mixture of olefin containing products was observed by NMR spectroscopy (TOF≈6.7 hr$^{-1}$ with respect to phenylacetylene). A doublet of triplets centered at 6.36 ppm and a doublet at 4.88 ppm were found representing the trans-olefin product, a doublet of doublets at 6.64 ppm and a triplet at 5.32 ppm were observed, representing $PhSiH(trans-C(H)=CH(Ph))_2$. Other minor olefin containing products were also observed.

Example 42

Hydrosilylation of Cyclohexylacetylene with Phenylsilane Using 1 Mol % of $κ^4$-N,N,P, P-$^{Ph}_2$$^{PPr}$DICoH Under an inert atmosphere, a J. Young tube was charged with 2.5 mg (0.0042 mmol) of $κ^4$-N,N,P,P-$^{Ph}_2$$^{PPr}$DICoH, 52.0 μL (0.422 mmol) phenylsilane, 55.0 μL (0.421 mmol) cyclohexylacetylene, and 0.5 mL $C_6D_6$. After 72 h, 60% conversion of cyclohexylacetylene to product to a mixture of olefin containing isomers was observed by NMR spectroscopy (TOF≈0.83 hr$^{-1}$ with respect to cyclohexylacetylene). A doublet of triplets centered at 6.33 ppm and a doublet at 4.81 ppm were found representing the trans-olefin product, a doublet of doublets were found at 5.6 ppm were found representing $PhSiH(trans-C(H)=CH(Cy))_2$. Other minor olefin containing products were also observed.

Example 43

Hydrosilylation of 4-Fluorophenylacetylene with Phenylsilane Using 1 Mol % of $κ^4$-N,N,P, P-$^{Ph}_2$$^{PPr}$DICoH Under an inert atmosphere, a J. Young tube was charged with 3.4 mg (0.0059 mmol) of $κ^4$-N,N,P,P-$^{Ph}_2$$^{PPr}$DICoH, 70.0 μL (0.568 mmol) phenylsilane, 65.0 μL (0.567 mmol) 4-fluorophenylacetylene, and 0.5 mL $C_6D_6$. After 6 h, greater than 99% conversion of 4-fluorophenylacetylene to product was observed by $^1$H NMR spectroscopy (TOF≈16.7 hr$^{-1}$ with respect to 4-fluorophenylacetylene) and is thought to form a mixture of product isomers. A doublet of triplets centered at 6.16 ppm and a doublet at 4.85 ppm were found representing the trans-olefin product, a doublet of doublets were found at 6.43 ppm and a triplet at 5.27 ppm were found representing $PhSiH(trans-C(H)=CH(4-F-Ph))_2$. Other minor olefin containing products were observed.

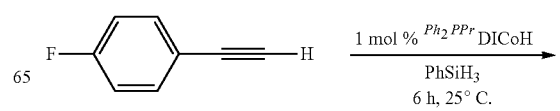

-continued

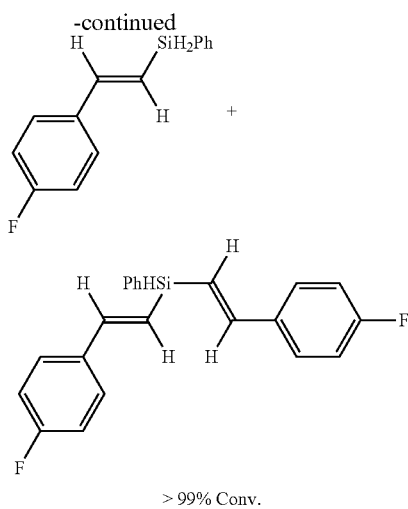

> 99% Conv.

Example 44

Hydrosilylation of 1-Hexyne with Phenylsilane Using 1 Mol % of $\kappa^4$-N,N,P,P-$^{Ph}_2{}^{PPr}$DICoH Under an inert atmosphere, a J. Young tube was charged with 2.6 mg (0.0044 mmol) of $\kappa^4$-N,N,P,P-$^{Ph}_2{}^{PPr}$DICoH, 54.0 μL (0.438 mmol) phenylsilane, 50.0 μL (0.435 mmol) 1-hexyne, and 0.5 mL $C_6D_6$. After 1 h, greater than 99% conversion of 1-hexyne to the trans-product was observed by $^1$H NMR spectroscopy (TOF≈6.7 hr$^{-1}$ with respect to 1-hexyne). A doublet of triplets centered at 6.13 ppm, a doublet of triplets at 5.50 ppm and a broad singlet at 4.62 were observed by $^1$H NMR spectroscopy.

Example 45

Hydrosilylation of Phenylacetylene with Phenylsilane Using 5 Mol % of $\kappa^4$-N,N,N,N-$^{PyEt}$PDIHCo In a nitrogen filled glove box, a 20 mL reaction vial was charged with 1 mg (0.002 mmol) of $\kappa^4$-N,N,N,N-$^{PyEt}$PDIHCo and 0.5 mL of $C_6D_6$. Another vial was charged with 5.7 μL of PhSiH$_3$, 5.1 μL of phenylacetylene, and 0.5 mL of $C_6D_6$. The latter solution was added into the former and the entire reaction was transferred into a J. Young NMR tube.

Figure 35:
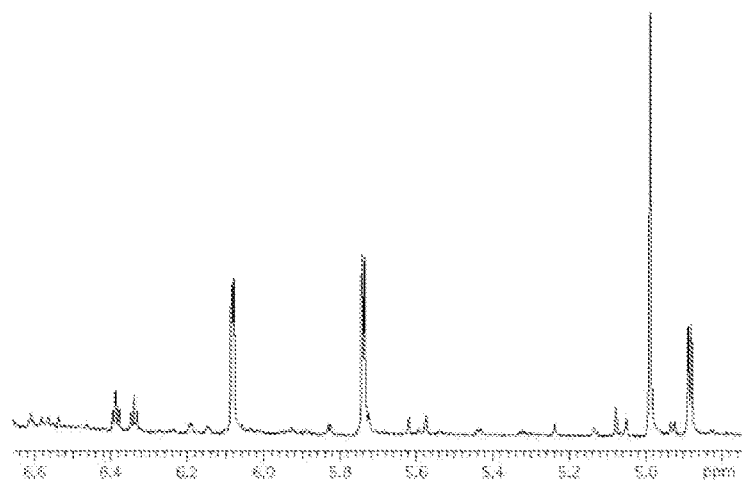
FIG. 35 shows the $^1$H NMR spectrum of silane products of the hydrosilylation described in Example 45.

A $^1$H NMR spectrum taken after 40 min revealed >99% conversion of phenylacetylene (TOF=30 h$^{-1}$) into a mixture of gem- (82%) and cis-alkenes (18%). Additional olefin containing products were observed. $^1$H NMR (400 MHz, benzene-d$_6$): 7.57, 7.51, 7.31, 7.06, 6.38 (t, J=3.2 Hz), 6.38 (t, J=3.2 Hz), 6.09 (d, J=2.4 Hz), 5.75 (d, J=2.4 Hz), 4.99 (s), 4.88 (d). This spectrum is included as FIG. 35.

Example 46

Hydrosilylation of Trimethylsilylacetylene with Phenylsilane Using 5 Mol % of $\kappa^4$-N,N,N,N-$^{PyEt}$PDIHCo In a nitrogen filled glove box, a 20 mL reaction vial was charged with 1.1 mg (0.002 mmol) of $\kappa^4$-N,N,N,N-$^{PyEt}$PDIHCo and 0.5 mL of $C_6D_6$. Another vial was charged with 5.7 μL of PhSiH$_3$, 6.6 μL of trimethylsilylacetylene, and 0.5 mL of $C_6D_6$. The latter solution was added to the former and the reaction was then transferred to a J. Young NMR tube.

A $^1$H NMR spectrum taken after 40 min revealed 60% conversion (TOF=18 h$^{-1}$) into a mixture of gem- (76%) and cis-alkenes (24%). $^1$H NMR (400 MHz, benzene-d$_6$): 7.54, 7.39, 7.08, 6.71 (t, J=2.8 Hz), 6.65 (t, J=2.8 Hz), 6.49 (d, J=4.8 Hz), 6.39 (d, J=4.8 Hz), 4.87 (s), 4.82 (d, J=2.8 Hz).

The present invention is not intended to be limited to the foregoing examples, but encompasses all modifications and variations that are within the scope of the appended claims. Many variations will become apparent to those skilled in the art upon review of this specification and the claims below.

All patents, patent applications, and publications mentioned herein are hereby incorporated by reference in their entirety as if each individual patent, patent application or publication was specifically and individually indicated to be incorporated by reference.

The invention claimed is:

1. A first row transition metal complex having a tetradentate or pentadentate supporting ligand, wherein the metal complex comprises a chemical structure as follows:

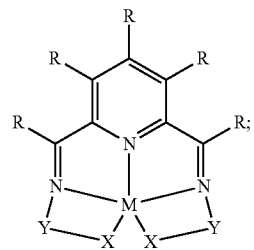

wherein:
M is Mn, Fe, Co, Ni, or a combination thereof;
each X is a donor group independently selected from PR$_n$, NR$_n$, AsR$_n$, SbR$_n$, BiR$_n$, OR$_n$, SR$_n$, SeR$_n$, TeR$_n$, where n=2, 1, or 0, a 3-7 membered saturated or unsaturated heterocycle containing one or more of a donor atom selected from P, N, As, Sb, Bi, O, S, Se, or Te, and any combination thereof;
each R is independently selected from hydrogen, an inert functional group, a substituted, unsubstituted, or cyclic C$_{1-24}$ alkyl group optionally having one or more heteroatoms, an aryl or substituted aryl group that optionally contains one or more heteroatoms, a moiety where two R groups taken together form a ring that is a substituted or unsubstituted, saturated or unsaturated cyclic structure that optionally contains one or more heteroatoms, a halogen, an alkoxide, an amide, a silyl, a boryl, and combinations thereof;
each Y is independently selected from a substituted or unsubstituted C$_{2-3}$ alkylene linking group optionally having one or more heteroatoms but not an aryl functionality directly attached to N;
or a salt thereof.

2. The metal complex of claim 1, wherein:
M is Mn, Fe, Co, or Ni; and
each X is independently selected from PR$_2$, NR$_2$, and any other donor group.

3. A catalytic composition comprising the metal complex of claim 1.

4. A method for reducing one or more organic substrates comprising contacting a composition comprising one or more organic substrates with a catalytic composition comprising a metal complex according to claim 1 in the presence of a reductant, whereby the one or more organic substrates are reduced.

5. The method of claim 4, wherein the reductant is a silane, a substituted silane, an alkoxysilane, hydrogen, a substituted borane, a substituted alane, or a mixture thereof.

6. The method of claim 4, wherein the one or more organic substrates contain a ketone, an ester, or mixtures thereof.

7. The method of claim 6, wherein the one or more organic substrates include an unsaturated organic compound.

8. The method of claim 7, wherein the unsaturated organic compound is an olefin or an alkyne.

9. A method of facilitating a hydrosilylation reaction, comprising reacting a compound comprising an Si—H bond with an unsaturated organic compound in the presence of one or more of the metal complexes of claim 1.

10. The method of claim 9, whereby the Si and H atoms in the Si—H bond are added across an unsaturated bond in the unsaturated organic compound to form an organosilicon compound.

11. A method of facilitating a hydrogenation reaction, comprising reacting $H_2$ with an unsaturated organic compound in the presence of one or more of the metal complexes of claim 1.

12. The method of claim 11, whereby the H atoms in the H2 are added across an unsaturated bond in the unsaturated organic compound to reduce the unsaturated bond.

\* \* \* \* \*